(12) United States Patent
Lo et al.

(10) Patent No.: US 7,645,576 B2
(45) Date of Patent: Jan. 12, 2010

(54) METHOD FOR THE DETECTION OF CHROMOSOMAL ANEUPLOIDIES

(75) Inventors: Yuk-Ming Dennis Lo, Kowloon (HK); Rossa Wai Kwun Chiu, Tai Po (HK); Bo Yin Tsui, Kowloon (HK); Chunming Ding, Shatin (HK); Charles Cantor, Del Mar, CA (US)

(73) Assignee: The Chinese University of Hong Kong, Shantin, N.T. (HK)

( * ) Notice: Subject to any disclaimer, the term of this patent is extended or adjusted under 35 U.S.C. 154(b) by 149 days.

(21) Appl. No.: 11/384,128

(22) Filed: Mar. 17, 2006

(65) Prior Publication Data
US 2006/0252071 A1    Nov. 9, 2006

Related U.S. Application Data

(60) Provisional application No. 60/663,173, filed on Mar. 18, 2005.

(51) Int. Cl.
*C07H 21/04* (2006.01)
*C12Q 1/68* (2006.01)

(52) U.S. Cl. .......................... 435/6; 435/91.1; 435/91.2; 536/23.1; 536/24.3

(58) Field of Classification Search ........................ None
See application file for complete search history.

(56) References Cited

U.S. PATENT DOCUMENTS 5,631,128 A * 5/1997 Kozal et al. ..................... 435/5

| | | |
|---|---|---|
| 5,994,057 A | 11/1999 | Peke et al. |
| 2002/0137088 A1 | 9/2002 | Bianchi |
| 2004/0197930 A1 | 10/2004 | Rosenfeld |
| 2004/0203037 A1 | 10/2004 | Lo |

FOREIGN PATENT DOCUMENTS

| AU | 2004202841 A1 | 1/2005 |
|---|---|---|
| WO | WO 02/068685 A2 | 6/2002 |

OTHER PUBLICATIONS

Findlay et al. (J. of Assisted Reproduction and genetics, vol. 15, No. 5, 1998, pp. 266-275).*
Kingdon et al. (Clinical Chemistry, vol. 49, No. 7, pp. 1087-1094, 2003).*
dBSNP rs8130833 (www.ncbi.nlm.nih.gov/SNP, Jul. 4, 2003).*
Farina, Antonio, et al., "Evaluation of Cell-Free Fetal DNA as a Second-Trimester Maternal Serum Market of Down Syndrome Pregnancy;" 2003; *Clinical Chemistry*; vol. 49; No. 2; pp. 239-242.

(Continued)

*Primary Examiner*—Jeanine A Goldberg
(74) *Attorney, Agent, or Firm*—Townsend and Townsend and Crew LLP

(57) ABSTRACT

The non-invasive detection of fetal chromosomal aneuploidies is demonstrated. Alleles of fetal RNA-SNPs present in a biological sample (e.g. maternal blood) containing fetal RNA are detected and quantified in order to determine the ratio of the alleles. This ratio is compared to a standard control consisting of euploid fetuses. Deviation of allele ratio indicates the presence of chromosomal aneuploidy.

30 Claims, 15 Drawing Sheets

OTHER PUBLICATIONS

Go, Attie, T.J.I., et al., "Detection of Placental Transcription Factor mRNA in Maternal Plasma;" 2004; *Clinical Chemistry*; vol. 50; No. 8; pp. 1413-1414.

Lee, Thomas, MD, "Down Syndrome and Cell-Free Fetal DNA in Archived Maternal Serum;" 2002; Presented at the *22nd Annual Meeting of the Society of Maternal-Fetal Medicine*, New Orleans, LA, Jan. 14-19, 2002, pp. 1217-1221.

Lo, Y.M. Dennis, et al., "Increased Fetal DNA Concentrations in the Plasma of Pregnant Women Carrying Fetuses with Trisomy 21;" 1999; *Clinical Chemistry*; vol. 45; No. 10; pp. 1747-1751.

NG., Enders, K.O., et al., "mRNA of Placental Origin is Readily Detectable in Maternal Plasma;" Apr. 15, 2003; *PNAS*'vol. 100; No. 8; pp. 4748-4753.

NG, Enders, K.O., et al, "The Concentration of Circulating Corticotrophin-Releasing Hormone mRNA in Maternal Plasma is Increased in Preeclampsia;" 2003; *Clinical Chemistry*; vol. 49, No. 5; pp. 727-731.

Oudejans, Cees B.M., et al., "Detection of Chromosome 21-Encoded mRNA of Placental Origin in Maternal Plasma;" 2003; *Clinical Chemistry*; vol. 49; No. 9; pp. 1445-1449.

Spencer, Kevin, et al.; "Increased Total Cell-Free DNA in the Serum of Pregnant Women Carrying a Fetus Affected by Trisomy 21;" 2003; *Prenatal Diagnosis*; vol. 23, pp. 580-583.

Tsui, N.B.Y., et al., "Systematic Micro-Array Based Identification of Placental mRNA in Maternal Plasma: Towards Non-Invasive Prenatal Gene Expression Profiling;" 2004; *J Med Genet*; vol. 41; pp. 461-467; www.jmedgenet.com.

Wataganara, Tuangsit, et al., "Maternal Serum Cell-Free Fetal DNA Levels are Increased in Cases of Trisomy 13 but not Trisomy 18;" 2003; *Human Genetics*, vol. 112; pp. 204-208.

Zhong, Xiao Yan, et al., "Fetal DNA in Maternal Plasma is Elevated in Pregnancies with Aneuploid Fetuses;" 2000; *Prenatal Diagnosis*; vol. 20; pp. 795-798.

Findlay, Ian, et al., "Rapid Trisomy Diagnosis (21, 18 and 13) Using Fluorescent PCR and Short Tandem Repeats: Applications for Prenatal Diagnosis and Preimplantation Genetic Diagnosis;" 1998; *Journal of Assisted Reproduction and Genetics*, vol. 15; No. 5; pp. 266-275.

Pertl, Barbara and Kroisel, Peter, et al., "Rapid Prenatal Diagnosis of Aneuploidy by Quantitative Fluorescent PCR on Fetal Samples from Mothers at High Risk for Chromosome Disorders;" *Molecular Human Reproduction*, 1999, vol. 5; No. 12; pp. 1176-1179.

Toth, T., et al., "Fluorescent Polymerase Chain Reaction for Rapid Detection of Common Chromosomal Aneuploidies;" Jun. 1998; *Clinical Chemistry*; vol. 44, No. 6; Supplement, p. A34.

* cited by examiner (A)

(B)

(C)

(D)

(A)

(B)

(C)

(D)

(A)

(B)

(A)

(B)

(A)

(B)

METHOD FOR THE DETECTION OF CHROMOSOMAL ANEUPLOIDIES

CROSS-REFERENCES TO RELATED APPLICATIONS

This application claims priority to U.S. Provisional Application No. 60/663,173, filed Mar. 18, 2005.

STATEMENT AS TO RIGHTS TO INVENTIONS MADE UNDER FEDERALLY SPONSORED RESEARCH OR DEVELOPMENT

NOT APPLICABLE

BACKGROUND OF THE INVENTION

Chromosomal aneuploidy is an important cause of morbidity during the prenatal and postnatal life. Assessment of chromosomal aneuploidy has traditionally been associated with the investigation of fetal viability and prenatal diagnosis. Methods for the detection and characterization of chromosomal aneuploidy include karyotyping of metaphase chromosomes, fluorescence in-situ hybridization (FISH) (Homer, J. et al., *Prenat Diagn* 23:566-571 (2003)), quantitative fluorescence polymerase chain reaction (PCR) (Mann, K. *Methods Mol Med* 92:141-156 (2004)), gene dosage PCR (Zimmermann, B. et al., *Clin Chem* 48:362-363 (2002), and array-based comparative genomic hybridization (CGH) (Hu, D. G. et al., *Mol Hum Reprod* (2004)).

Fetal chromosomal aneuploidy is known to contribute significantly to fetal loss and accounts for 50% of the first trimester spontaneous abortions (Chitty, L. *Br Med Bull* 54:839-856 (1998)). Viable fetuses are especially associated with certain types of chromosomal aneuploidy. Trisomy 21, or Down syndrome, is the most common autosomal aneuploidy compatible with postnatal survival with an occurrence of 1 in 800 live births (Hook, E. B. *Lancet* 2:169-172 (1981)). Trisomy 21 is the most common reason why couples opt for prenatal diagnosis. At present, definitive diagnosis of a trisomy 21 fetus and other chromosomal aneuploidies rely on the genetic analysis of fetal genetic material obtained by invasive procedures such as amniocentesis and chorionic villus sampling (CVS). By virtue of their invasive nature, these procedures are associated with a finite risk of spontaneous abortion. Hence, other noninvasive approaches have been developed to stratify pregnancies according to the risk of carrying a trisomy 21 fetus. Only pregnancies with a substantive risk, defined as a risk greater than the procedure-related risk of fetal loss, are recommended to undergo the invasive procedures. The risk stratification strategies that have been in current use include the assessment of maternal age, maternal serum biochemical markers and fetal ultrasound features (Nicolaides, K. H. et al., *Prenat Diagn* 22:308-315 (2002)).

To attain better sensitivity and specificity, various combinations of markers and approaches have been evaluated (Wald, N. J. et al., *Prenat Diagn* 17:821-829 (1997)), including the triple test, quadruple test (Wald, N. J. et al., *Lancet* 361:835-836 (2003)), integrated test (Wald, N. J. et al., *N Engl J Med* 341:461-467 (1999)) and first trimester screening (Wapner, R. et al., *N Engl J Med* 349:1405-1413 (2003)). Serum biochemical markers in use include, alpha-fetoprotein, unconjugated estriol, total or free beta-human chorionic gonadotropin, inhibin-A, and pregnancy-associated plasma protein-A (PAPP-A). Pregnancies whose risk is shown to be high by these screening modalities are ultimately referred for amniocentesis or CVS.

Recently, the discovery of circulating cell-free fetal nucleic acids in maternal plasma has provided an alternative source of fetal genetic material which can be sampled noninvasively (Lo, Y. M. D. et al., *Lancet* 350:485-487 (1997); Poon, L. L. M. et al., *Clin Chem* 46:1832-1834 (2000)). Furthermore, the concentrations of circulating fetal DNA in the plasma of women carrying trisomy 21 fetuses have been shown to be significantly higher than those in women carrying euploid fetuses (Lo, Y. M. D. et al., *Clin Chem* 45:1747-1751 (1999); Zhong, X. Y. et al., *Prenat Diagn* 20:795-798 (2000)). Recently, circulating fetal RNA has also been shown to be promising as a class of gender-independent fetal nucleic acid markers in maternal plasma. (Ng, E. K. O. et al., *Clin Chem* 49:727-731 (2003); Ng, E. K. O. et al., *Proc Natl Acad Sci USA* 100:4748-4753 (2003)). Thus, circulating fetal nucleic acid quantification is useful as an additional prenatal screening marker for the risk stratification of pregnancies.

Placenta-expressed mRNA transcripts, such as those coding for human placental lactogen (hPL), human chorionic gonadotropin beta subunit (βhCG) (Ng, E. K. O. et al., *Clin Chem* 49:727-731 (2003)), corticotropin releasing hormone (CRH) (Ng, E. K O. et al., *Proc Natl Acad Sci USA* 100:4748-4753 (2003b)), tissue factor pathway inhibitor 2 (TFPI2), KiSS-1 metastasis-suppressor (KISS1) and placenta-specific 1 (PLAC1) (Tsui, N. B. Y. et al., *J Med Genet* 41:461-7 (2004)), have been shown to be detectable in maternal plasma. These placenta-derived mRNA species are known to be pregnancy-specific (Ng, E. K. O. et al., *Proc Natl Acad Sci USA* 100:4748-4753 (2003); Tsui, N. B. Y. et al., *J Med Genet* 41:461-7 (2004)). In particular, aberrant elevations in CRH mRNA concentrations in maternal plasma have been reported in preeclamptic pregnancies (Ng, E. K. O. et al., *Clin Chem* 49:727-731 (2003)). As these placenta-expressed markers are pregnancy-specific but gender- and polymorphism-independent, they are useful in the noninvasive prenatal assessment of all pregnancies.

Chromosomal aneuploidy alters the dosage of genes located on the aneuploid chromosome. The altered gene dosage can be reflected by a distorted allele ratio of the genes. The distorted allele ratio is in turn reflected by a distorted ratio of alleles of polymorphisms present on the RNA transcript of the genetic loci on the aneuploid chromosome. One example of such polymorphisms is single nucleotide polymorphism (SNP) in which the ratio of the SNP alleles may be distorted in the presence of aneuploidy of the chromosome concerned. Thus, a reference range for the RNA-SNP ratio is established for normal pregnancies and fetal trisomy 21 can be determined when a deviation from the reference ratio is observed. In comparison to conventional cytogenetic methods of analysis, the proposed technique does not require prior culturing of the fetal cells and therefore shortens the analytical time. In addition, maternal blood samples can be obtained non-invasively, thus minimizing potential harm to both the fetus and the mother.

BRIEF SUMMARY OF THE INVENTION

In one embodiment, the present invention provides an improved method for detecting the presence of a chromosomal disorder in the fetus of a pregnant woman using the ratio of alleles of RNA transcript molecules from the pregnant woman's fetus in comparison to the ratio found in pregnant women with a chromosomally normal fetus. The use of the ratio in this manner provides superior sensitivity in detecting fetal chromosomal disorders, especially when compared to merely quantifying the amount of a particular allele or the total concentration of a particular RNA transcript present.

The first step of the method involves determining the ratio of alleles of the RNA transcripts in the fetus of a pregnant woman. This is accomplished by obtaining an RNA-containing biological sample from the pregnant woman, wherein the RNA-containing biological sample contains fetal RNA. The alleles are then discriminated from RNA transcribed from at least one genetic locus from at least one chromosome of concern, followed by determination of the ratio of the alleles of the RNA transcripts. The second step involves comparing the ratio from the pregnant woman to a standard control representing an average ratio of alleles from comparable biological samples obtained from pregnant women each carrying a chromosomally normal fetus, wherein an increase or decrease in the ratio from the standard control indicates an increased risk of having a fetus with a chromosomal disorder.

In some embodiments, the present invention provides a method in which the chromosomal disorder is a member selected from the group consisting of trisomy 21, trisomy 18 and trisomy 13. In other embodiments, the chromosomal disorder is trisomy 21. In another embodiment, the chromosomal disorder is trisomy 13. In a further embodiment, the chromosomal disorder is trisomy 18. In yet another embodiment, the chromosomal disorder involves the X chromosome or the Y chromosome.

In another embodiment, the present invention provides a method in which the biological sample from the step of obtaining an RNA-containing biological sample is a member selected from the group consisting of maternal blood, maternal plasma or serum, amniotic fluid, a chorionic villus sample, biopsy material from a preimplantation embryo, fetal nucleated cells or fetal cellular remnants isolated from maternal blood, maternal urine, maternal saliva, washings of the female reproductive tract and a sample obtained by celocentesis. In still another embodiment, the biological sample is maternal blood. In yet another embodiment, the biological sample is a chorionic villus sample. In a further embodiment, the biological sample contains cellular elements or cellular remnants in maternal blood.

In other embodiments, the present invention provides a method in which the fetal RNA from the step of obtaining an RNA-containing biological sample is derived from the placenta.

In another embodiment, the present invention provides a method where the step of discriminating the alleles of RNA involves reverse transcriptase polymerase chain reaction (RT-PCR).

In a further embodiment, the present invention provides a method where the step of discriminating the alleles of RNA and/or the step of determining the ratio of the different alleles is performed using a member selected from the group consisting of a primer extension reaction, mass spectrometry, hybridization using at least one probe, hybridization using at least one fluorescently labeled probe, direct sequencing, cloning and sequencing, and electrophoresis.

In some embodiments, the present invention provides a method in which the alleles of the steps involving discriminating the alleles of RNA, determining the ratio of the different alleles, and comparing the ratio from the previous step to a standard control are differentiated by sequence variation. In another embodiment, the sequence variation is a single nucleotide polymorphism (SNP). In a further embodiment, the sequence variation is an insertion/deletion polymorphism. In still another embodiment, the sequence variation is a simple tandem repeat polymorphism.

In other embodiments, the present invention provides a method in which the RNA is transcribed from a member selected from the group consisting of chromosome 21, chromosome 18, chromosome 13, chromosome X and chromosome Y. In another embodiment, the RNA is transcribed from chromosome 21. In a further embodiment, the RNA is transcribed from chromosome 18. In still another embodiment, the RNA is transcribed from chromosome 13.

In another embodiment, the present invention provides a method in which the RNA is expressed in the placenta at a level which is two-fold or more than that of maternal blood. In some embodiments, the RNA is expressed in the placenta at a level which is five-fold or more than that of maternal blood. In other embodiments, the RNA is expressed in the placenta at a level which is ten-fold or more than that of maternal blood.

In a further embodiment, the present invention provides a method in which the RNA is mRNA. In another embodiment, the RNA is transcribed from at least one genetic locus selected from the group consisting of collagen VI alpha 1 (COL6A1), superoxide dismutase 1 (SOD1), collagen VI alpha 2 (COL6A2), mitochondrial ATP synthase O subunit (ATP5O), BTG family, member 3 (BTG 3), a disintegrin-like and metalloprotease (reprolysin type) with thrombospondin type 1 motif, 1 (ADAMTS1), beta-site APP-cleaving enzyme 2 (BACE2), intersectin 1 (ITSN1), amyloid beta (A4) precursor protein (APP), ATP synthase, H+ transporting, mitochondrial F0 complex, subunit F6 (ATP5J), Down syndrome critical region gene 5 (DSCR5), placenta-specific 4 (PLAC4), hypotheticalprotein BC005107 (LOC90625), ribosomalprotein L17 (RPL17), serpin peptidase inhibitor lade B (ovalbumin) member 2 (SERPINB2) and collagen type IV alpha 2 (COL4A2). In yet another embodiment, the RNA is transcribed from a genetic locus which contains a single nucleotide polymorphism (SNP). In other embodiments, the RNA is transcribed from at least one genetic locus selected from the group consisting of collagen VI alpha 1 (COL6A1) and collagen VI alpha 2 (COL6A2). In still other embodiments, the SNP in the RNA transcribed from the genetic locus of the COL6A1 is $^{Arg}850_{His}$ or $^{Ser}932_{Ser}$. In yet another embodiment, the SNP in the RNA transcribed from the genetic locus of the COL6A2 is $^{Val}728_{Val}$.

In another embodiment, the present invention provides a method in which the RNA is transcribed from the genetic locus for placenta-specific 4 (PLAC4). In yet another embodiment, the RNA is any variant transcribed from the PLAC4 gene, such as AF269287, AK027868, AK092431, BC093685, BC101615, BC101617, L13197, NM__182832 and LOC191585. In still yet another embodiment, the RNA transcribed from the genetic locus of the PLAC4 gene contains a single nucleotide polymorphism, or an insertion-deletion polymorphism selected from the group consisting of rs3804026, rs4818219, rs9977003, rs7844, rs9015, rs13643, rs9305729, rs9305730, rs5019195, rs5019194, rs5844069, rs1049904, rs16998089, rs12482116, rs1909439, rs7278659, rs12106409, rs12106395, rs12106401, rs12106434, rs2183584, rs3949725, rs8130833, rs10222145 and rs9981478, or other polymorphisms located within the PLAC4 gene locus such as PLAC4-41471145 and PLAC4-41476236.

In some embodiments, the present invention provides a method wherein the woman is during the first trimester of gestation. In other embodiments, the woman is during the second or third trimester of gestation.

In a further embodiment, the present invention provides a method wherein the comparison step shows an increased risk of the fetus having a chromosomal disorder if the ratio of the alleles of the RNA transcripts in the fetus of a pregnant woman is higher or lower by 1 standard deviation from the standard control. In another embodiment, the comparison step shows an increased risk of the fetus having a chromosomal disorder if the ratio of the alleles of the RNA transcripts in the fetus of a pregnant woman is higher or lower by 2 standard deviations from the standard control. In some other embodiments, the comparison step shows an increased risk of the fetus having a chromosomal disorder if the ratio of the alleles of the RNA transcripts in the fetus of a pregnant woman is higher or lower by 3 standard deviations from the standard control.

In another embodiment, the present invention provides a kit for detecting the presence of a fetus with a chromosomal disorder in a pregnant woman. One component of the kit is primers for amplifying the region of interest. Another component of the kit is a standard control representing an average ratio of alleles from comparable biological samples obtained from pregnant women each carrying a chromosomally normal fetus. In yet another embodiment, a third component of the kit comprises hybridization probes for discriminating between the different alleles of each RNA species.

DETAILED DESCRIPTION OF THE INVENTION

I. Definitions

Figure 1:
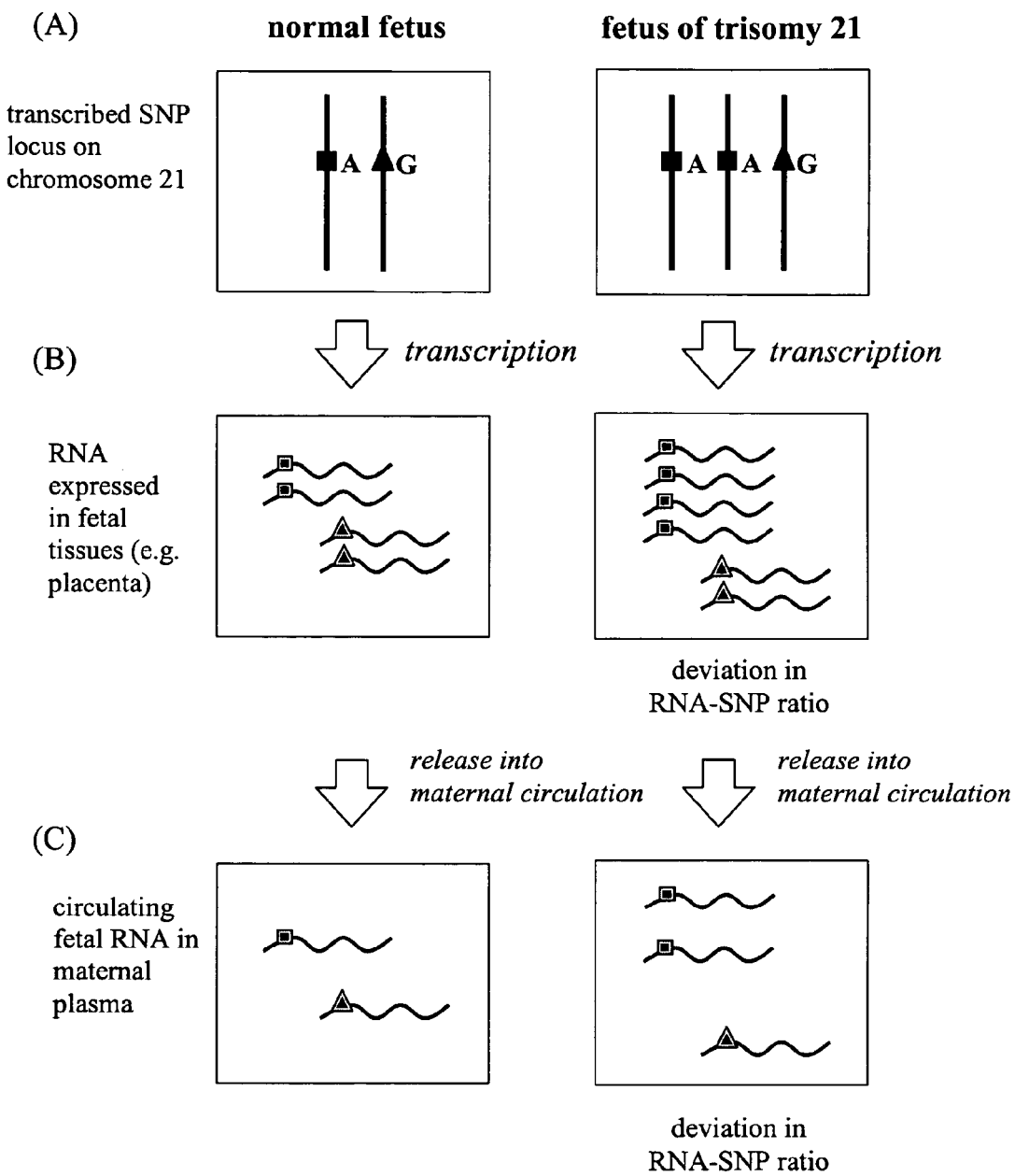
FIG. 1. Schematic illustration of one embodiment of the strategy employed for the noninvasive determination of fetal trisomy 21 through maternal blood, serum or plasma analysis by the relative quantification of alleles of placenta-expressed transcripts located on chromosome 21. (A) Normal and trisomy 21 fetuses heterozygous at a transcribed SNP locus on chromosome 21. The fetus with trisomy 21 has an extra copy of the gene. "A" and "G" denote the respective alleles of the transcribed SNP. (B) The gene is expressed in placental tissues and the resultant transcripts are allelic by exhibiting the coding SNPs. The ratio of the two RNA alleles in trisomy 21 placenta is expected to deviate from that of the normal placenta, due to the expression of an extra copy of the gene. (C) The RNA transcripts are released into maternal blood and their relative abundance is reflective of the placental gene expression profile. Thus, the maternal blood, serum or plasma ratio of the two RNA alleles in a trisomy 21 pregnancy is expected to deviate from that of a normal pregnancy.

As used herein, the term "chromosomal disorder" refers to a state of chromosomal abnormality where the number of chromosomes is not an exact multiple of the usual haploid number: frequently, there is either an additional chromosome or one missing. A common chromosomal disorder is aneuploidy. A common form of chromosomal aneuploidy is a trisomy, where a single additional chromosome is present. For example, trisomy 18 is a chromosomal abnormality where a third chromosome 18 is found in a cell, whereas a third chromosome 21 is present in the cells of a patient suffering from trisomy 21. "Chromosomal disorder" may also refer to a state of chromosomal abnormality where a proportion of one or more chromosomes is not an exact multiple of the usual haploid number, due to, for example, chromosome translocation. Chromosomal translocation (e.g. translocation between chromosome 21 and 14 where some of the 14th chromosome is replaced by extra 21st chromosome) may cause partial trisomy 21.

As used herein, the term "RNA-containing biological sample" refers to a biological sample (such as those discussed below) that contains ribonucleic acid (RNA). RNA refers to a polymer of ribonucleotides that has a sequence corresponding to at least a portion of a pre-selected location in the human genome. RNA as used herein includes, but is not limited to, mRNA, ribosomal RNA and micro RNA. RNA can be protein encoding sequences such as mRNA, or non-coding sequences such as ribosomal RNA, microRNA or other transcribed sequences without well-defined functions. mRNA is an RNA molecule transcribed from the DNA of a gene, and from which a protein is translated by the action of ribosomes. Ribosomal RNA (rRNA) is a non-coding RNA that is not translated into a protein. Micro RNA (mRNA) is a sub-type of "small RNAs" that are distinguished by their origins, not their functions. Micro RNA is less than 30 nucleotides in length, and is transcribed from DNA but not translated into protein. One of skill in the art will appreciate that other types of RNA are useful in the present invention.

As used herein, the terms "fetal", "placental derived" and "placental expressed" refer to the origin of certain RNA species that are detectable in a biological sample from a pregnant woman, e.g., blood. For example, a fetal RNA species is one that has been transcribed from a fetal DNA sequence. Placental-derived or placental expressed RNA is one type of fetal RNA. One of skill in the art will appreciate that other fetal RNA are useful in the present invention. A placental derived or placental expressed RNA species is one that is transcribed in the placenta.

As used herein, the term "discriminating alleles from RNA transcribed from at least one genetic locus from at least one chromosome of concern" refers to the detection and quantification of particular RNA alleles transcribed from a particular genetic locus on a chromosome. The detection and quantification of alleles can be carried out by a variety of methods, including the use of hybridization probes and quantitative real time polymerase chain reaction (QRT-PCR). Other methods include the use of mass spectrometry (MS), electrophoresis, pyrosequencing, primer extension microarrays, chips and sequencing.

As used herein, the term "ratio of the alleles" refers to the ratio of the population of one allele and the population of the other allele in a biological sample. In some cases, it is possible that in trisomies a fetus may be tri-allelic for a particular locus. In such cases, the term "ratio of the alleles" refers to the ratio of the population of any one allele against one of the other alleles, or any one allele against the other two alleles.

As used herein, the term "standard control" refers to a sample suitable for the use of a method of the present invention, in order for determining the ratio of the RNA-SNP alleles transcribed from a particular genetic locus, e.g., COL6A1, SOD1, COL6A2, ATP5O, BTG3, ADAMTS1, BACE2, ITSN1, APP, ATP5J, DSCR5, PLAC4, LOC90625, RPL17, SERPINB2 or COL4A2. Such sample contains a known ratio of the RNA-SNP alleles transcribed from a particular genetic locus that closely reflects the average ratio of such RNA-SNP alleles in pregnant women who each carries a chromosomally normal fetus. The standard control can also represent the mean ratio, the median ratio, or another useful ratio known to one of skill in the art. Determination of the standard control is described in greater detail below.

As used herein, the term "pregnant women" refers to a group of pregnant women who each carries a chromosomally normal fetus, and refers to certain characteristics, such as the ratio of RNA alleles transcribed from the loci of interest, that is representative of a randomly selected group of women who carry chromosomally normal fetuses. This selected group should comprise a sufficient number of women such that the average, mean, median or other mathematical relationship, ratio of RNA alleles transcribed from the loci of interest among these women reflects, with reasonable accuracy, the ratio of RNA alleles in the general population of healthy pregnant women with healthy fetuses. The mother can be screened for the risk of fetal chromosomal aneuploidy during the first trimester of pregnancy, about the first 13 weeks of gestation. The mother can also be screened during the second or third trimester of gestation. The second trimester of gestation is from about 14 to about 27 weeks of gestation. The third trimester of gestation is from about 28 weeks to the end of gestation, about 40 weeks. Moreover, the preferred gestational age for testing may also depend on the RNA marker used in testing.

As used herein, the term "chromosomally normal" refers to the state where the number of chromosomes is an exact multiple of the haploid number, such as twice the number of chromosomes found in a haploid, and each chromosome is present in the same number (except the sex chromosomes in the case of, e.g., male humans, where two different sex chromosomes, X and Y, are present at one copy each).

As used herein, the term "an increase or a decrease in the ratio from the standard control" refers to a positive or negative change in the ratio as compared to the standard control. An increase is preferably at least 10%, more preferably at least 50%, and most preferably at least 100%. Similarly, a decrease is preferably at least 10%, more preferably at least 50%, and most preferably at least 90%. In addition, the increase or decrease in the ratio can be at least 1 standard deviation from the standard control. The increase or decrease can also be at least 2 standard deviations from the standard control. The increase or decrease can also be at least 3 standard deviations from the standard control.

As used herein, the term "single nucleotide polymorphism" (SNP) refers to a nucleic acid sequence variation involving the alteration of a single nucleotide. SNPs useful in the present invention include those present on the corresponding RNA transcripts transcribed from the genetic loci of interest including, but not limited to, collagen VI alpha 1 (COL6A1), superoxide dismutase 1 (SOD1), collagen VI alpha 2 (COL6A2), mitochondrial ATP synthase O subunit (ATP5O), BTG family, member 3 (BTG 3), a disintegrin-like and metalloprotease (reprolysin type) with thrombospondin type 1 motif, 1 (ADAMTS1), beta-site APP-cleaving enzyme 2 (BACE2), intersectin 1 (ITSN1), amyloid beta (A4) precursor protein (APP), ATP synthase, H+ transporting, mitochondrial F0 complex, subunit F6 (ATP5J), Down syndrome critical region gene 5 (DSCR5), placenta-specific 4 (PLAC4), hypothetical protein BC005107 (LOC90625), ribosomalprotein L17 (RPL17), serpin peptidase inhibitor lade B (ovalbumin) member 2 (SERPINB2) and collagen type IV alpha 2 (COL4A2). Such SNPs are termed RNA-SNPs since they involve the alteration of a single nucleotide on RNA. Alleles of the RNA-SNPs are then used in the present invention to determine a ratio of the RNA-SNP alleles in a biological sample obtained from a pregnant woman and to compare that ratio to the ratio obtained from biological samples obtained from a group of pregnant women each with a normal fetus. One of skill in the art will appreciate that other markers and insertion/deletion polymorphisms are also useful in the present invention.

As used herein, the term "maternal blood" refers to a blood sample or preparation from a pregnant woman or a woman being tested for possible pregnancy. The term encompasses whole blood or any fractions of blood. Examples of "maternal blood" include plasma and serum. A maternal blood sample that is essentially free of cells is also referred to as "acellular," where generally no platelets are present.

As used herein, the term "cellular elements or cellular remnants" refers to parts of cells that remain in the biological sample, including, but not limited to, platelets, apoptotic bodies and syncytiotrophoblast microparticles.

II. Methods of the Present Invention

The present invention uses the pregnancy-specificity of fetal-expressed transcripts to develop a method which allows the genetic determination of fetal chromosomal aneuploidy and thus the establishment of its diagnosis noninvasively. In one embodiment, the fetal-expressed transcripts are those expressed in the placenta. Specifically, the present invention detects single nucleotide polymorphisms (SNPs) from RNA transcripts with tissue-specific expression patterns that are encoded by genes on the aneuploid chromosome. Other polymorphisms are also detectable by the methods of the present invention, such as an insertion/deletion polymorphism and a simple tandem repeat polymorphism. The status of the locus is determined through the assessment of the ratio between informative SNPs on the RNA transcribed from the genetic loci of interest. In short, the present invention compares the ratio between alleles of a polymorphic site on locus- and tissue-specific RNA transcripts from an aneuploid fetus to a euploid fetus.

The present invention, therefore, can be applied to the prenatal diagnosis of trisomy 21 which involves the analysis of informative SNPs on RNA transcripts with placental tissue expression that are derived from loci on chromosome 21. Fetal trisomy 21 is then determined by comparing the ratios between the informative SNPs through the detection of the placenta-expressed RNA transcripts in maternal blood. The fetal-specificity of the markers in maternal blood is conferred by their placental tissue expression, while the aneuploid status is determined by the abnormal ratios between the informative SNPs on the RNA transcripts.

The methods of the present invention enable the genetic determination of fetal trisomy 21 and its prenatal diagnosis based on the analysis of placenta-expressed RNA-SNPs encoded by genetic loci on chromosome 21. The RNA-SNP alleles can be discriminated by, for example, real-time QRT-PCR assays and the ratio between them, which is indicative of the gene dosage of the locus, is determined. In another embodiment, the RNA-SNP alleles can be discriminated by primer extension followed by mass spectrometry.

A. Chromosomal Disorders Detectable Using the Methods of the Present Invention The present invention provides methods for the detection of chromosomal aneuploidies such as trisomy 21. The methods also enable detection of other fetal aneuploidies, such as those present on, or that involve, chromosomes 18, 13, X and Y. The methods also enable the noninvasive detection of fetal chromosomal aneuploidy when maternal blood is analyzed. The utility of RNA-SNP detection does extend beyond the detection of chromosomal abnormalities to the detection of other genetic variations of the fetus, e.g. paternally-inherited polymorphisms and mutations.

B. Biological Samples Useful in the Present Invention for Detecting Fetal Chromosomal Disorders The first step of practicing the present invention is to obtain a biological sample from a pregnant woman at a gestational age suitable for testing using a method of the present invention, or from a woman who is being tested for possible pregnancy. The suitable gestational age may vary depending on the disorder tested and sometimes the RNA marker used, as discussed above.

The biological sample can be maternal blood, including maternal plasma or serum. In some circumstances, the biological sample is acellular. In other circumstances, the biological sample does contain cellular elements or cellular remnants in maternal blood. Other biological samples include amniotic fluid, chorionic villus sample, biopsy material from a preimplantation embryo, maternal urine, maternal saliva, a celocentesis sample, fetal nucleated cells or fetal cellular remnants, or the sample obtained from washings of the female reproductive tract.

When the biological sample is blood, collection of blood from a woman is performed in accordance with the standard protocol hospitals or clinics generally follow. An appropriate amount of peripheral blood, e.g., between 3-20 ml, is collected and can be stored according to standard procedure prior to further preparation.

Biological samples useful in the present invention contain fetal RNA. The fetal RNA can be transcribed from chromosomes 21, 18, 13, X and Y. In addition, the level at which RNA is expressed in the placenta can be two times, five times or ten times or more the level expressed in the maternal blood or its various fractions.

The fetal RNA is typically derived from any tissue of fetal origin including, but not limited to, the placenta, and can be mRNA. The RNA can be extracted from the biological sample by a variety of methods. The general methods of RNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain RNA from a blood sample from a woman. Combinations of more than one of these methods may also be used. Careful handling of the samples, thorough treatment with DNase, and proper negative controls in the amplification and quantification steps should be used to eliminate DNA from the RNA preparations.

C. Methods for Discriminating Alleles of RNA Transcripts

Discriminating the alleles of RNA transcripts can be accomplished by a variety of methods, including PCR, mass spectrometry (MS), gel electrophoresis, pyrosequencing, primer extension assays, chips, sequencing and hybridization with one or more fluorescent probes.

1. PCR-Based Discrimination of RNA-SNP Alleles

Once RNA is extracted from the biological sample, the amount of each particular SNP allele of the RNA of interest, e.g., COL6A1, SOD1, COL6A2, ATP5O, BTG3, ADAMTS1, BACE2, ITSN1, APP, ATP5J, DSCR5, PLAC4, LOC90625, RPL17, SERPINB2 or COL4A2, may be assessed.

Variants of the selected gene are also useful in the present invention. For example, useful variants of the PLAC4 gene include variants identified by the GenBank accession numbers: AF269287, AK027868, AK092431, BC093685, BC101615, BC101617, L13197, NM_182832 and LOC191585. The RNA transcribed from the genetic locus of the PLAC4 gene contains one or more single nucleotide polymorphism, or insertion-deletion polymorphism. Exemplary polymorphisms transcribed from the PLAC4 gene include, but are not limited to, polymorphisms identified by the database of SNPs ((dbSNP) www.ncbi.nlm.nih.gov/SNP/) accession numbers (with PLAC4 coordinates based on the Human May 2004 (hg17) assembly at the UCSC Genome Browser (genome.ucsc.edu/)): rs3804026 (PLAC4-41469163), rs4818219 (PLAC4-41469764), rs9977003 (PLAC4-41470591), rs7844 (PLAC4-41470699), rs9015 (PLAC4-41470877), rs13643 (PLAC4-41471296), rs9305729 (PLAC4-41472272), rs9305730 (PLAC4-41472277), rs5019195 (PLAC4-41473295), rs5019194 (PLAC4-41473302), rs5844069 (PLAC4-41473306), rs1049904 (PLAC4-41473392), rs16998089 (PLAC4-41473496), rs12482116 (PLAC4-41475590), rs11909439 (PLAC4-41475912), rs7278659 (PLAC4-41476875), rs12106409 (PLAC4-41477273), rs12106395 (PLAC4-41477340), rs12106401 (PLAC4-41477425), rs12106434 (PLAC4-41477486), rs2183584 (PLAC4-41477956), rs3949725 (PLAC4-41478283), rs8130833 (PLAC4-41478755), rs10222145 (PLAC4-41480512) and rs9981478 (PLAC4-41480564), or other polymorphisms located within the PLAC4 gene locus such as PLAC4-41471145 and PLAC4-41476236, which are located at the nucleotide coordinates of 41471145 and 41476236, respectively, on chromosome 21 based on the Human May 2004 (hg17) assembly at the UCSC Genome Browser (genome.ucsc.edu/). Those of skill in the art will appreciate that other polymorphisms in PLAC4 are also useful in the present invention.

The dbSNP accession numbers refer only to the SNP portion of the genomic sequence on which the SNP is located. The extent of the sequence provided for the SNP can be selected for both the upstream and downstream portions of the transcribed genomic sequence.

Other RNA-SNPs useful in the present invention include $^{Arg}850_{His}$ of COL6A1 (COL6A1-46247817), $^{Ser}932_{Ser}$ of COL6A1 (COL6A1-46248064) and $^{Val}728_{val}$ of COL6A2 (COL6A2-46370341), on chromosome 21 based on the Human May 2004 (hg17) assembly at the UCSC Genome Browser (genome.ucsc.edu/).

In most instances, it is desirable to amplify the target sequence using any of several nucleic acid amplification procedures which are well known in the art (listed above and described in greater detail below). Specifically, nucleic acid amplification is the enzymatic synthesis of nucleic acid amplicons (copies) which contain a sequence that is complementary to a nucleic acid sequence being amplified. Nucleic acid amplification is especially beneficial when the amount of target sequence present in a sample is very low. By amplifying the target sequences and detecting the amplicon synthesized, the sensitivity of an assay can be vastly improved, since fewer target sequences are needed at the beginning of the assay to better ensure detection of nucleic acid in the sample belonging to the organism or virus of interest.

Amplification of polynucleotides utilizes methods such as the polymerase chain reaction (PCR), ligation amplification (or ligase chain reaction (LCR)) and amplification methods based on the use of Q-beta replicase. Also useful are strand displacement amplification (SDA), thermophilic SDA, nucleic acid sequence based amplification (3SR or NASBA) and transcription-associated amplification (TAA). These methods are well known and widely practiced in the art. Reagents and hardware for conducting PCR are commercially available.

Prior to the amplification step, it is typically necessary to synthesize a DNA copy (cDNA) of the RNA transcript of interest. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Primers useful to amplify the RNA transcript sequences are preferably complementary to, and hybridize specifically to sequences that flank a target region therein. The polynucleotide sequences generated by amplification may be sequenced directly. Alternatively, the amplified sequence(s) may be cloned prior to sequence analysis. As a third possibility, primers may be designed to overlap the SNP site for the practice of allele-specific PCR. Allele-specific PCR enables the discrimination of RNA-SNP alleles as only the correctly hybridized primers will be amplified. PCR primers refers to oligonucleotides that can be used in a polymerase chain reaction (PCR) to amplify a nucleotide sequence originated from an RNA species transcribed from a locus of interest, such as COL6A1, SOD1, COL6A2, ATP5O, BTG3, ADAMTS1, BACE2, ITSN1, APP, ATP5J, DSCR5, PLAC4, LOC90625, RPL17, SERPINB2 or COL4A2. At least one of the PCR primers for amplification of a nucleotide sequence encoding an above-named transcript should be sequence-specific for the locus.

Although PCR amplification of the target RNA-SNP alleles is typically used in practicing the present invention, one of skill in the art will recognize that amplification of the RNA species in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to amplify the signal of RNA markers in maternal blood. For a review of branched-DNA (bDNA) signal amplification for direct quantification of nucleic acid sequences in clinical samples, see Nolte, *Adv. Clin. Chem.* 33:201-235, 1998.

2. Other Methods for the Discrimination of RNA-SNP Alleles

The RNA-SNP alleles of interest can also be detected using other standard techniques, well known to those of skill in the art. Although the detection step is typically preceded by an amplification step, amplification is not required in the methods of the invention. For instance, the RNA transcript may be identified by size fractionation (e.g., gel electrophoresis), whether or not proceeded by an amplification step. After running a sample in an agarose or polyacrylamide gel and labeling with ethidium bromide according to well known techniques (see, Sambrook and Russell, *Molecular Cloning: A Laboratory Manual* 3d ed., 2001), the presence of a band of the same size as the standard control is an indication of the presence of a target RNA sequence, the amount of which may then be compared to the control based on the intensity of the band. Alternatively, oligonucleotide probes specific to RNA encoding, e.g., COL6A1, SOD1, COL6AZ ATP5O, BTG3, ADAMTS1, BACE2, ITSN1, APP, ATP5J, DSCR5, PLAC4, LOC90625, RPL17, SERPINB2 or COL4A2, can be used to detect the presence of such RNA species and indicate the amount of RNA molecules in comparison to the standard control, based on the intensity of signal imparted by the probe.

Sequence-specific probe hybridization is a well known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well known techniques and the detection is not a critical aspect of the present invention. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange high-performance liquid chromatography (HPLC) as described in Pearson and Regnier, *J. Chrom.*, 255:137-149, 1983.

Other useful methods for discriminating alleles of RNA transcripts include direct sequencing, such as pyrosequencing. The process of pyrosequencing involves a primer-template complex where each of the four deoxynucleotide triphosphates is added one at a time. When the deoxynucleotide triphosphate is incorporated by the DNA polymerase, light is emitted. The amount of light generated is proportional to the number of bases added. Accordingly, the downstream sequence can be inferred.

The primer extension reaction is also useful in the present invention. The primer extension reaction operates by discriminating the SNP alleles by the incorporation of deoxynucleotides and/or dideoxynucleotides to a primer extension primer which hybridizes to a region adjacent to the SNP site. The primer is extended with a polymerase. The primer extended SNP can be detected physically by mass spectrometry or by a tagging moiety such as biotin. As the SNP site is only extended by a complementary deoxynucleotide or dideoxynucleotide that is either tagged by a specific label or generates a primer extension product with a specific mass, the SNP alleles can be discriminated.

Mass spectrometry methods enable the detection of a polynucleotide, for example a PCR amplicon or a primer extension product. The presence of the polynucleotide sequence is verified by comparing the mass of the detected signal with the expected mass of the polynucleotide of interest. The relative signal strength for a particular polynucleotide sequence indicates the relative population of a specific allele, thus enabling calculation of the allele ratio directly from the data. For a review of genotyping methods by mass spectrometry, see Pusch et al., *Pharmacogenomics* 3:537-548, 2002.

D. Determining the Ratio of Alleles of RNA-SNPs

Generally, the determination of the ratio of the alleles of RNA-SNPs involves calculating the relative population of each RNA-SNP allele that is present in the sample, and dividing the value determined for one RNA-SNP allele by the value for the other RNA-SNP allele. Using a PCR based detection system entails dividing the label intensity associated with the PCR, primer extension or hybridization reaction products generated from one of the alleles with that of the other allele of the RNA transcript. Other methods for determining the ratio of alleles of RNA-SNP include comparing the abundance of sequencing products or the number of cloned sequences for each of the alleles. The RNA-SNP ratio can also be determined by comparing the mass signal intensities of the alleles by mass spectrometry.

Alternatively, the RNA-SNP ratio can be determined from the difference in the fluorescent intensity ($\Delta$Rn) accumulated for each allele during a reaction, or from the number of PCR cycles required for a reaction of each allele to have accumulated a threshold fluorescent intensity (Ct). The $\Delta$Ct and $\Delta\Delta$Rn are reflective of the RNA-SNP allele ratio because these values are proportional to the logarithm of the amount of the RNA allele. As a result, the difference in the threshold cycle values ($\Delta$Ct) or the difference in the accumulated fluorescent intensities ($\Delta\Delta$Rn) for each allele is reflective of the SNP ratio for a RNA transcript. For example, allele A can be detected with a FAM (6-carboxyfluorescein) labeled probe and allele B can be detected with a fluorescent probe such as VIC (from Applied Biosystems). The Ct and the $\Delta$Rn values are calculated for each of allele A and allele B. The difference of the two Ct values is determined using threshold cycle values, and affords the $\Delta$Ct value. The difference in the two $\Delta$Rn values is determined using the accumulated fluorescent intensities and affords the $\Delta\Delta$Rn value. As the Ct and $\Delta$Rn values are logarithmically related to the abundance of PCR products, the difference in the Ct and $\Delta$Rn values for each RNA-SNP is calculated and that difference (the $\Delta$Ct and $\Delta\Delta$Rn values) is reflective of the RNA-SNP ratio between the two RNA alleles.

E. Comparison of the RNA-SNP Ratio to a Standard Control

Once the ratio of alleles has been determined in the subject, the ratio is compared to the standard control in order to determine the presence of fetal aneuploidy. A RNA-SNP ratio that is either higher or lower when compared to a known value determined in the control sample, indicates the presence of a fetal aneuploidy. For example, a $\Delta$Ct value, $\Delta\Delta$Rn value or the label or mass intensity ratios between the SNP alleles that is either higher or lower when compared to a known value determined in the control sample, indicates the presence of a fetal aneuploidy.

In order to establish a standard control, a group of healthy pregnant women carrying healthy fetuses are first selected. These women are preferably, but not necessarily, of similar gestational age, which is within the appropriate time period of pregnancy for screening of conditions such as fetal chromosomal aneuploidy using the methods of the present invention.

Similarly, a standard control is established using samples from a group of healthy non-pregnant women. The healthy status of the selected pregnant women and the fetuses they are carrying is confirmed by well established, routinely employed methods including, but not limited to, cytogenetic analysis or conducting fetal genetic analysis using the methods described above for obtaining a biological sample. The standard control can be determined prior to testing for the presence of fetal aneuploidy.

Furthermore, the selected group of healthy pregnant women carrying healthy fetuses must be of a reasonable size, such that the average, mean or median ratio of RNA-SNP alleles encoding COL6A1, SOD1, COL6A2, ATP5O, BTG3, ADAMTS1, BACE2, ITSN1, APP, ATP5J, DSCR5, PLAC4, LOC90625, RPL17, SERPINB2 or COL4A2, calculated from the group can be reasonably regarded as representative of the normal or average, mean or median amount among the general population of healthy women carrying healthy fetuses. In some instances, the group comprises at least 10 women.

Once an average value is established for the ratio of RNA-SNP alleles based on the individual values found in each women of the selected group, this value is considered a standard for the RNA species. Any blood sample that contains a similar ratio of RNA of the same species can thus be used as a standard control. A solution containing RNA encoding COL6A1, SOD1, COL6A2, ATP5O, BTG3, ADAMTS1, BACE2, ITSN1, APP, ATP5J, DSCR5, PLAC4, LOC90625, RPL17, SERPINB2 or COL4A2, with a ratio of the established average of the same species can also be artificially assembled and serve as a standard control.

An increase in the RNA-SNP ratio that is at least 10% higher as compared to the average value in the control sample, indicates an increased risk of having a fetus with chromosomal disorder. In some cases, the increase in the RNA-SNP ratio is at least 50% higher. In other cases, the increase in the RNA-SNP ratio is at least 100% higher. In still other cases, an RNA-SNP ratio that is at least 10% lower as compared to the average value in the control sample, indicates an increased risk of having a fetus with a chromosomal disorder. In some other cases, the decrease is at least 50%, or at least 90%.

A RNA-SNP ratio that is at least one standard deviation higher or lower than the average value in the control sample indicates an increased risk of having a fetus with a chromosomal disorder. A RNA-SNP ratio that is at least two standard deviations higher or lower than the average value in the control sample indicates an increased risk of having a fetus with a chromosomal disorder. A RNA-SNP ratio that is at least three standard deviations higher or lower than the average value in the control sample indicates an increased risk of having a fetus with a chromosomal disorder. In some cases, a RNA-SNP ratio that is less than one standard deviation higher or lower than the average value in the control sample will also indicate an increased risk of having a fetus with a chromosomal disorder.

F. Kits for Detecting a Chromosomal Disorder in a Fetus of a Pregnant Woman

The present invention also provides kits for detecting the presence of a fetus having a chromosomal disorder. The kits of the present invention include primers for amplifying the region of interest. Primers useful in the kits of the present invention are described above for the discrimination of alleles. The primers can be specific for a marker or act in a non-specific fashion.

Another component of the kits of the present invention is a standard control representing the ratio of the RNA alleles in average pregnant women with a chromosomally normal fetus. The standard control is determined in the same manner as that described above for the methods of detecting the chromosomal disorder in the fetus of a pregnant woman.

The kits of the present invention can also comprise hybridization probes for discriminating the different alleles of each RNA species. The alleles of each RNA species can be single nucleotide polymorphisms, insertion/deletion polymorphisms or simple tandem repeat polymorphisms. Hybridization probes useful in the kits of the present invention are the same hybridization probes used for the methods of detecting the chromosomal disorder in the fetus of a pregnant woman. The hybridization probes can be radioactive, fluorescent, chemiluminescent or enzymatic. Oligonucleotides used as probes can be prepared according to known techniques (Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984). The probes of the present invention can be specific or non-specific. One of skill in the art will recognize that other methods of discriminating the alleles of each RNA species are useful in the kits of the present invention, such as those methods described above.

Kits of the instant invention may comprise additional elements that one of skill in the art will appreciate are useful in the kits of the present invention.

The following examples are provided by way of illustration only and not by way of limitation. Those of skill in the art will readily recognize a variety of non-critical parameters that can be changed or modified to yield essentially similar results.

III. EXAMPLES

The methods of the present invention are useful for detecting chromosomal disorders in individuals who are heterozygous for a particular genetic locus, to detect if the individuals have an abnormal number of chromosomes at that particular locus, e.g., an abnormal 3 instead of the normal 2. In the case of pregnancy, while the biological sample is taken from the pregnant woman directly, the individual being tested fro the chromosomal aneuploidy is the fetus that the pregnant woman is carrying. In one embodiment of the application of this approach for prenatal diagnosis, the extra copy of the gene is expressed along with the normal gene pair in placental tissues. The ratio of the RNA alleles in the placenta deviates from that of the normal placenta, as a result of the extra copy of the gene. The RNA transcripts are then released into the maternal blood, and their relative abundance is reflective of the placental gene expression profile. Accordingly, the ratio of the RNA alleles in the blood or its fractions (e.g. plasma) of the pregnant woman carrying a fetus having a chromosomal disorder, deviates from that of a pregnant woman carrying a euploid fetus (FIG. 1).

The detection of a chromosomal disorder using the RNA alleles requires the identification of a marker that is specific for the fetus and is present at detectable expression levels in the mother's blood, identification of a transcribed region on that marker having high placental expression, the ability to detect the transcript in the mother's blood, determination that the transcripts are pregnancy-specific, and determination of the allelic-ratio of the transcripts in order to assess the presence or absence of the chromosomal disorder.

The examples below demonstrate specific examples of identifying useful markers and trancripts, methods for detecting the transcripts and ensuring that the transcripts are pregnancy-specific, and methods for quantifying the transcripts and determining the RNA allele ratio to detect a chromosomal disorder. One of skill in the art will recognize that other methods and techniques are also useful in practicing the instant invention.

Example 1

Identification of SNPs Useful for Detecting Trisomy 21 in Fetuses

The identification of SNPs useful for the detection of fetal trisomy 21 requires the identification of an RNA species that is expressed by fetal cells and is present in detectable concentrations in the analyzed biological samples.

Identification of Fetal-Specific Transcripts with High Placental Expression Levels Gene expression profiles of five first-trimester chorionic villus sample (CVS) samples were obtained by microarray analysis of each individual tissue sample. In an effort to identify placenta-expressed transcripts amongst the circulating RNA molecules in maternal plasma, the gene expression profiles of maternal whole blood (specifically maternal hematopoietic cells) were obtained and compared with that of the corresponding placental tissues. Placenta-expressed transcripts in early pregnancy were identified by selecting transcripts whose expression levels were increased in the CVS tissues when compared to the corresponding whole blood samples in all five comparisons.

Sample processing and RNA extraction. Five first-trimester placental tissue samples were obtained from pregnant women by CVS before therapeutic terminations. Fetal karyotype in all cases were subsequently confirmed to be normal. The placental tissue samples were stored in RNAlater™ (Ambion®, Austin, Tex.) immediately upon collection and kept at −80° C. until RNA extraction. Six milliliters of maternal peripheral blood were collected concurrently at the time of tissue collection and stored in PAXgene™ Blood RNA Tubes (PreAnalytiX, Hombrechtikon, Switzerland). Total RNA from placental tissues were extracted with the Trizol Reagent (Invitrogen, Carlsbad, Calif.) and purified with RNeasy mini-kit (Qiagen, Hilden, Germany) following manufacturer's protocols. Total RNA from peripheral blood was extracted by PAXgene™ Blood RNA Kit (PreAnalytiX, Hombrechtikon, Switzerland) according to manufacturer's instructions, with the inclusion of DNase treatment (RNase-Free DNase Set, Qiagen, Hilden, Germany).

Gene expression analysis by high-density oligonucleotide arrays. For each sample, ten micrograms of the extracted RNA were labeled and hybridized to the GeneChip® Human Genome U133A and U133B Arrays (Affymetrix, Santa Clara, Calif.) according to the manufacturer's instructions. After hybridization, each array was washed and stained in a GeneChip® Fluidics Station 400 (Affymetrix). The chips were scanned with the GeneArray Scanner (Affymetrix) and analyzed using the GeneChip® Microarray Suite 5.0 (Affymetrix). Transcripts that were predominantly expressed in placental tissues instead of maternal peripheral blood and are derived from chromosome 21 were selected. Out of 7226 gene transcripts expressed in the CVS samples, 1245 transcripts were identified to have higher expression in the CVS than the maternal peripheral blood samples. Among this panel of transcripts, 13 placenta expressed genes located on chromosome 21 were identified (Table 1).

TABLE 1

Microarray detection of placenta-expressed genes located on chromosome 21. Transcripts are sorted in descending order according to the median of the respective microarray signals.

| Probe Set ID | Sequence Derived From | Transcripts | Symbol | Location | *Signal (median) |
|---|---|---|---|---|---|
| 213428_s_at | AA292373 | Collagen, type VI, alpha 1 | COL6A1 | 21q22.3 | 8419.2 |
| 200642_at | NM_000454.1 | superoxide dismutase 1, soluble (amyotrophic lateral sclerosis 1 (adult)) | SOD1 | 21q22.11 | 7084.7 |
| 209156_s_at | AY029208.1 | Collagen, type VI, alpha 2 | COL6A2 | 21q22.3 | 7076.9 |
| 200818_at | NM_001697.1 | ATP synthase, H+ transporting, mitochondrial F1 complex, O subunit (oligomycin sensitivity conferring protein) | ATP5O | 21q22.11 | 3247.8 |
| 213134_x_at | AI765445 | BTG family, member 3 | BTG3 | 21q21.1 | 2564.9 |
| 214953_s_at | X06989.1 | amyloid beta (A4) precursor protein (protease nexin-II, Alzheimer disease) | APP | 21q21.3 | 2376.1 |
| 202325_s_at | NM_001685.1 | ATP synthase, H+ transporting, mitochondrial F0 complex, subunit F6 | ATP5J | 21q21.1 | 2303.1 |
| 214750_at | L13197 | placenta-specific 4 | PLAC4 | 21q22.3 | 2209.9 |
| 222162_s_at | AK023795.1 | a disintegrin-like and metalloprotease (reprolysin type) with thrombospondin type 1 motif, 1 | ADAMTS1 | 21q21.2 | 1780.8 |
| 217867_x_at | NM_012105.1 | beta-site APP-cleaving enzyme 2 | BACE2 | 21q22.3 | 1093.4 |
| 221689_s_at | AB035745.1 | Down syndrome critical region gene 5 | DSCR5 | 21q22.2 | 900.7 |
| 209298_s_at | AF114488.1 | intersectin 1 (SH3 domain protein) | ITSN1 | 21q22.1-q22.2 | 199.9 |
| #232191_at | BC005107.1 | hypothetical protein BC005107 | LOC90625 | 21q22.3 | 6910.2 |

*Medians of microarray signals from five first trimester placental tissues
Transcripts that were detected by Human Genome U133B Arrays (Affymetrix). Transcripts without specification were detected by Human Genome U133A Arrays (Affymetrix)

Identification of Applicable SNPs and Determination of Allele Frequencies

SNPs in the transcribed regions of the selected chromosome 21 genetic loci with predominant placental tissue expression were identified from a public database. The allele frequencies of each SNP were then determined in both Chinese and Caucasian populations. SNPs with high heterozygosity rates were targeted.

Among the 13 chromosome-21 genes with predominant placental expression (Table 1), four of the genes with the highest placental expression levels, namely collagen VI alpha 1 (COL6A1), superoxide dismutase 1 (SOD1), collagen VI alpha 2 (COL6A2) and mitochondrial ATP synthase O subunit (ATP5O), were selected for further evaluation. SNPs that are located within exons of these genes were selected in order to enable the study of mRNA polymorphisms. The allele frequencies of each of these coding polymorphisms were determined in 10 Chinese and 10 Caucasian buffy coat DNA samples by direct sequencing with the use of PCR primers flanking the corresponding SNPs (Table 2). Sequencing was performed using BigDye Terminator Cycle Sequencing v1.1 (Applied Biosystems, Foster City, Callif) and a Model 3100 DNA Analyzer (Applied Biosystems).

TABLE 2

PCR primers for the direct sequencing of the four chromosome 21 genes.

Sequences (5' to 3')

| Transcripts | Forward primer | SEQ ID NO: | Reverse primer | SEQ ID NO: |
|---|---|---|---|---|
| COL6A1 | GGCTGACATCACCATCCTG | 1 | AGAGCAGCAGCCTCTTCTTG | 3 |
|  | TTGGAAAGCCAGGACACAAC | 2 | TGAGGATTGGTGGGAAAAAC | 4 |
| SOD1 | TTTTCCACTCCCAAGTCTGG | 5 | CGACAGAGCAAGACCCTTTC | 7 |
|  | TTGCAACACCAAGAAAAAGC | 6 | TCTGGCAAAATACAGGTCATTG | 8 |
| COL6A2 | TCATCAACGTGGTCAACAGG | 9 | TCACTCTCGTGCTTCTCGTG | 12 |
|  | GTGGACATCGTCTTCCTGCT | 10 | GTGGATGGCAGTGAGGTTGT | 13 |
|  | AACGACAGTCTGCACGAGTC | 11 | CAGGTAGGTCAGGAGCCTTG | 14 |
| ATP5O | GGCCTGAGATTCTTCACTGC | 15 | AAAATTAGCGGGACATGGTG | 16 |

The allele frequencies of the transcribed SNPs are shown in Table 3. SNPs which were heterozygous in at least 30% of one of the two populations were considered to be informative and were selected as targets for further assay development.

TABLE 3

Genotyping of the coding SNPs in 10 Chinese and 10 Caucasian unrelated individuals for COL6A1, SOD1, COL6A2 and ATP5O.

| COL6A1 | dbSNP Allele | 1053312 A/G | 1053315 A/G | 13879 T/C | 1053320 T/C | 1053331 A/G | 9254 A/G |
|---|---|---|---|---|---|---|---|
| Chinese | f (minor allele) | 0.20 | 0.20 | 0 | 0.20 | 0 | 0.10 |
|  | Heterozygosity | 0.32 | 0.32 | 0 | 0.320 | 0 | 0.18 |
| Caucasian | f (minor allele) | 0.40 | 0.40 | 0.05 | 0.40 | 0.15 | 0.15 |
|  | Heterozygosity | 0.48 | 0.48 | 0.10 | 0.48 | 0.26 | 0.26 |

| SOD1 | dbSNP Allele | 1804450 T/C | 1804449 T/C | 4804447 T/C | 15012 G/A | 1804448 G/T |
|---|---|---|---|---|---|---|
| Chinese | f (minor allele) | 0 | 0 | 0 | 0.20 | 0 |
|  | Heterozygosity | 0 | 0 | 0 | 0.32 | 0 |
| Caucasian | f (minor allele) | 0 | 0 | 0 | 0.25 | 0 |
|  | Heterozygosity | 0 | 0 | 0 | 0.38 | 0 |

| COL6A2 | dbSNP Allele | 1042917 A/G | 2839114 A/G | 3182348 T/C | 1042930 A/G | 6652 T/C | 1043801 A/G |
|---|---|---|---|---|---|---|---|
| Chinese | f (minor allele) | 0.50 | 0.50 | 0 | 0 | 0 | 0 |
|  | Heterozygosity | 0.50 | 0.50 | 0 | 0 | 0 | 0 |
| Caucasian | f (minor allele) | 0.45 | 0.50 | 0 | 0 | 0.15 | 0.15 |
|  | Heterozygosity | 0.50 | 0.50 | 0 | 0 | 0.26 | 0.26 |

|  | dbSNP Allele | 3087667 C/T | 1043962 G/A | 1043985 T/C |
|---|---|---|---|---|
| Chinese | f (minor allele) | 0 | 0 | 0 |
|  | Heterozygosity | 0 | 0 | 0 |
| Caucasian | f (minor allele) | 0 | 0 | 0 |
|  | Heterozygosity | 0 | 0 | 0 |

TABLE 3-continued

| ATP5O | dbSNP Allele | 4842 A/G | 4591 C/T |
|---|---|---|---|
| Chinese | f (minor allele) | 0.15 | 0 |
|  | Heterozygosity | 0.26 | 0 |
| Caucasian | f (minor allele) | 0.40 | 0 |
|  | Heterozygosity | 0.48 | 0 |

The dbSNP accession numbers for each SNP locus are listed. For each SNP, the minor allele is listed first. "f (minor allele)" denotes the frequency of the minor allele.

Determination of Detectability and Pregnancy-Specificity of Selected Transcripts The four chromosome 21 transcripts with placenta expression can be detected in maternal plasma using real-time QRT-PCR assays developed for amplifying the non-polymorphic regions of the four transcripts. These transcripts are present in the plasma of pregnant women at significantly higher concentrations as compared to non-pregnant women. In addition, the concentration of the transcripts in the maternal plasma drops precipitously following birth of the child. Accordingly, the placenta is a predominant source of these mRNA transcripts in maternal plasma.

Sample collection and processing. Whole blood samples from six non-pregnant women and ten first-trimester pregnant women were collected. Peripheral blood samples from five third-trimester pregnant women before and at 24 hours after delivery were also recruited. Twelve milliliters of the blood samples were collected in EDTA tubes and were centrifuged at 1600×g for 10 min at 4° C. Plasma was then carefully transferred into plain polypropylene tubes. The plasma samples were re-centrifuged at 16000×g for 10 min at 4° C. Supernatants were collected into fresh polypropylene tubes. RNA extraction from maternal plasma was performed by mixing 3.2 ml of plasma with 4 ml of Trizol LS reagent (Invitrogen, Carlsbad, Calif.) and 0.8 ml of chloroform (Ng, E. K. O. et al., *Clin Chem* 48:1212-1217 (2002)). The mixture was centrifuged at 12000×g for 15 min at 4° C. and the aqueous layer was transferred into new tubes. One volume of 70% ethanol was added to one volume of the aqueous layer. The mixture was then applied to an RNeasy mini column (Qiagen, Hilden, Germany) and was processed according to manufacturer's recommendations. Total RNA was eluted with 60 µl of RNase-free water and stored at −80° C. DNase treatment (RNase-Free DNase Set, Qiagen, Hilden, Germany) was carried out to remove any contaminating DNA.

Development of real-time QRT-PCR assays. QRT-PCR assays were developed for the detection of collagen VI alpha 1 (COL6A1), superoxide dismutase 1 (SOD1), collagen VI alpha 2 (COL6A2) and mitochondrial ATP synthase O subunit (ATP5O) mRNA. The sequences of the primers and the TaqMan minor-groove-binding (MGB) fluorescent probes (Applied Biosystems, Foster City, Calif, USA) are shown in Table 4. Calibration curves were prepared by serial dilutions of high performance liquid chromatography-purified single stranded synthetic DNA oligonucleotides (Bustin, 2000) (Proligo, Singapore) specific for the respective amplicons, with concentrations ranging from 1 X $10^6$ copies to 10 copies. The sequences of the synthetic DNA oligonucleotide for COL6A1, SOD1, COL6A2 and ATP5O are described in Table 4. Absolute concentrations of all transcripts were expressed as copies/ml of plasma.

TABLE 4

Sequences of primers and probes for real-time QRT-PCR detection of the placenta-expressed transcripts encoded on chromosome 21.

| Transcripts | | Sequences (5' to 3')[1] | SEQ ID NO: |
|---|---|---|---|
| COL6A1 | F primer | GACAAAGTCAAGTCCTTCACCAA | 17 |
|  | R primer | GCGTTCCACACCAGGTTT | 18 |
|  | Probe | (FAM) CGCTTCATCGACAACC (MGBNFQ) | 19 |
|  | standard curve | TGGACAAAGTCAAGTCCTTCACCAAGCGCTTCATCGACAACCTGAGGGACAGGTACTACCGCTGTGACCGAAACCTGGTGTGGAACGCAG | 20 |
| SOD1 | F primer | CAGGGCATCATCAATTTCG | 31 |
|  | R primer | TGCTTCCCCACACCTTCA | 22 |
|  | Probe | (FAM) CAGAAGGAAAGTAATGGACCA (MGBNFQ) | 23 |
|  | standard curve | TGCAGGGCATCATCAATTTCGAGCAGAAGGAAAGTAATGGACCAGTGAAGGTGTGGGGAAGCATT | 24 |
| COL6A2 | F primer | GATCAACCAGGACACCATCAA | 25 |
|  | R primer | CCGTAGGCTTCGTGTTTCA | 26 |

TABLE 4-continued

Sequences of primers and probes for real-time QRT-PCR detection of the placenta-expressed transcripts encoded on chromosome 21.

| Transcripts | | Sequences (5' to 3')[1] | SEQ ID NO: |
|---|---|---|---|
| | Probe | (FAM) CGCATCATCAAGGTC (MGBNFQ) | 27 |
| | standard curve | GAGATCAACCAGGACACCATCAACCGCATCATCAAGGTCATGAAACACGAAGCCTACGGAG | 28 |
| ATP5O | F primer | CCCTCACTACCAACCTGATCA | 29 |
| | R primer | CCTTGGGTATTGCTTAATCGA | 30 |
| | Probe | (FAM) TGCTTGCTGAAAATG (MGBNFQ) | 31 |
| | standard curve | TCCCCTCACTACCAACCTGATCAATTTGCTTGCTGAAAATGGTCGATTAAGCAATACCCAAGGAG | 32 |

[1]FAM: fluorescent label; MGBNFQ: minor groove binding non-fluorescent quencher.

The QRT-PCR reactions were set up according to the manufacturer's instructions (EZ rTth RNA PCR reagent set, Applied Biosystems) in a reaction volume of 25 µl. The QRT-PCR assays were carried out in a combined thermal cycler and fluorescent detector (ABI Prism 7700, Applied Biosystems). For all of the four transcripts, the PCR primers (Proligo) and the fluorescent probes (Applied Biosystems) were used at concentrations of 300 nM and 100 nM, respectively. 5 µl of extracted plasma RNA were used for amplifications. Multiple negative water blanks were included in every analysis.

The thermal profiles used for COL6A1, SOD1, COL6A2 and ATP5O analysis were as follows: the reaction was initiated at 50° C. for 2 min for the included uracil N-glycosylase to act, followed by reverse transcription at 60° C. for 30 min. After a 5-min denaturation at 95° C., 40 cycles of PCR were carried out using denaturation at 92° C. for 15 s and 1 min annealing/extension at 57° C. for COL6A1 and ATP5O, 56° C. for COL6A2 and 59° C. for SOD1.

Figure 2:
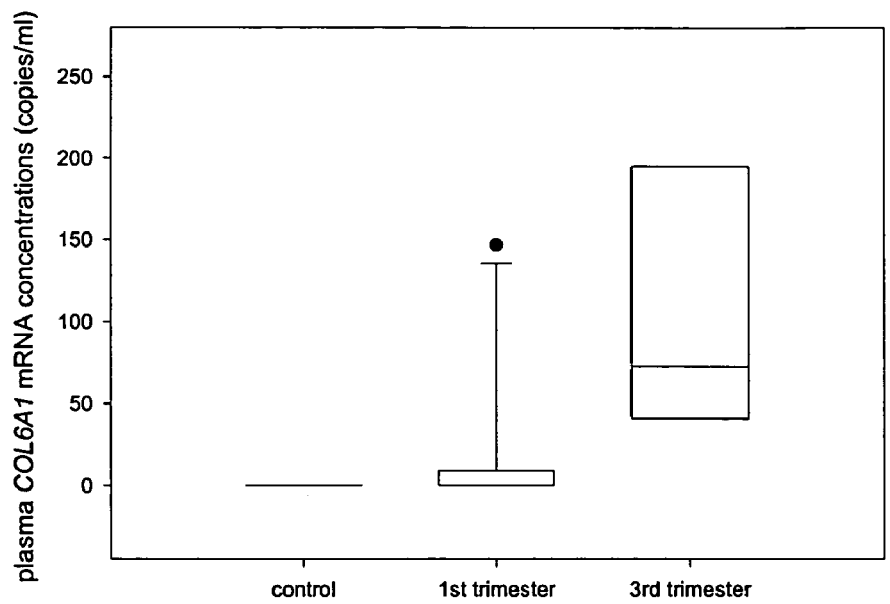
FIG. 2. Box plots of concentrations of placenta-derived mRNA transcripts in maternal plasma of non-pregnant women, and women in the first and third trimesters of pregnancies, respectively. (A) COL6A1 mRNA. (B) SOD1 mRNA. (C) COL6A2 mRNA and (D) ATP5O mRNA. Control, non-pregnant women; $1^{st}$ trimester, women in first trimester of pregnancy; $3^{rd}$ trimester, women in third trimester of pregnancy. The lines inside the boxes denote the medians. The boxes mark the interval between the $25^{th}$ and $75^{th}$ percentiles. The error bars denote the interval between $10^{th}$ and $90^{th}$ percentiles. The filled circles mark the data points outside the $10^{th}$ and $90^{th}$ percentiles.
Figure 2:
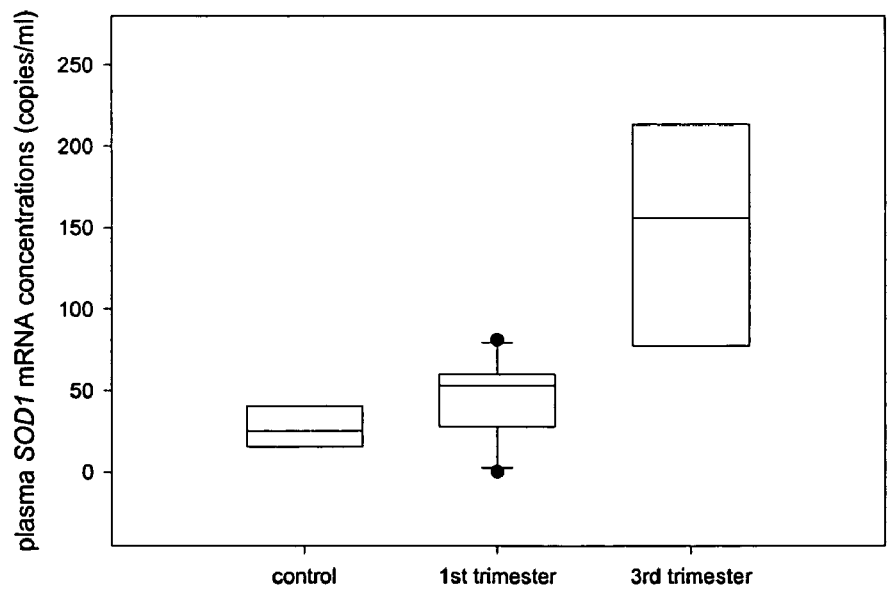
Figure 2:
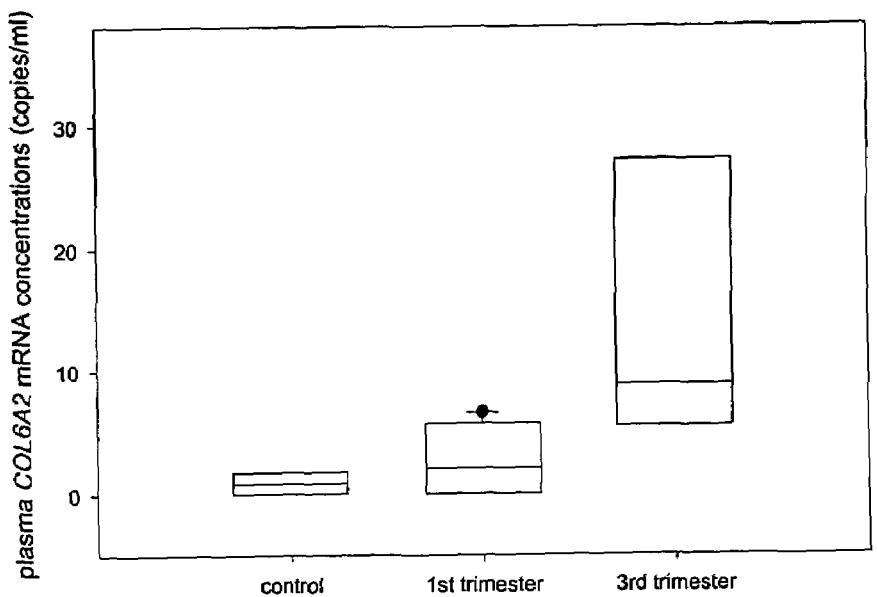
Figure 2:
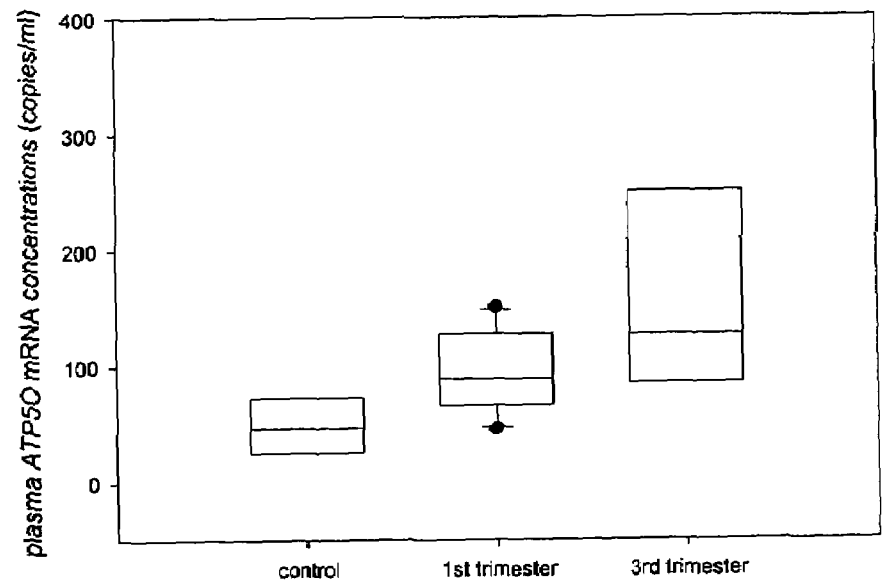
Figure 3:
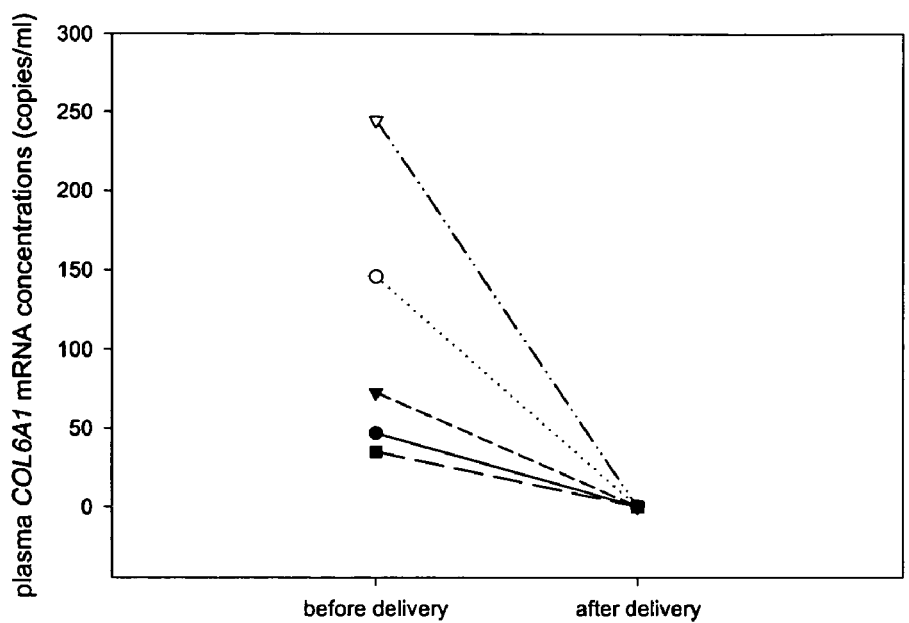
FIG. 3. Clearance of placenta-derived mRNA transcripts from maternal plasma after delivery. (A) COL6A1, (B) SOD1, (C) COL6A2 and (D) ATP5O mRNA concentrations in maternal plasma before and at 24 hours after delivery. Each line represents a paired plasma sample obtained from one subject.
Figure 3:
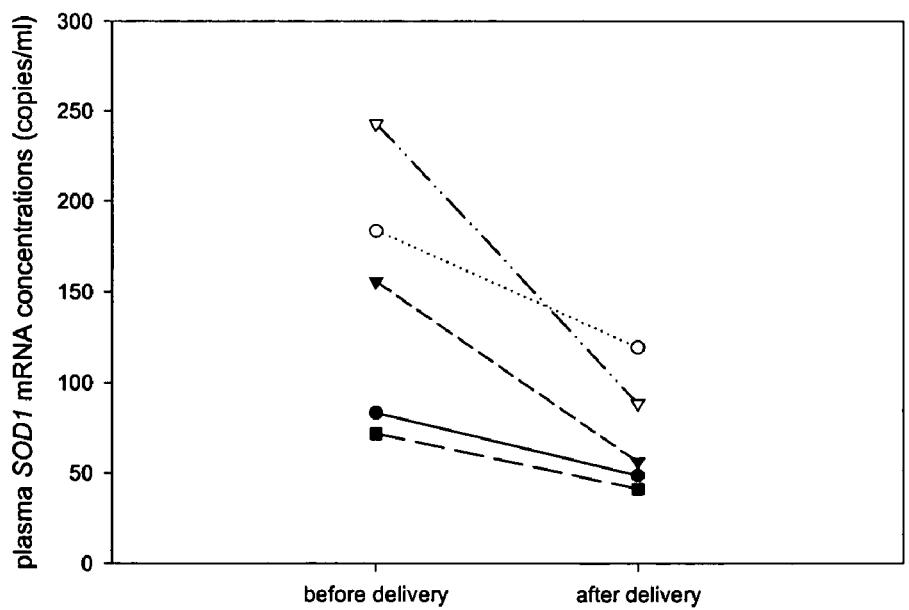
Figure 3:
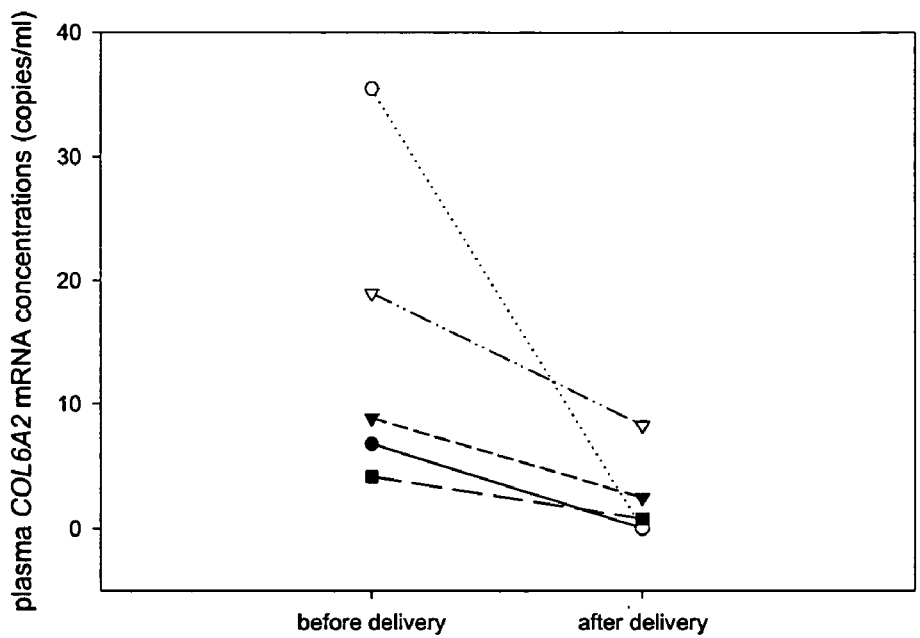
Figure 3:
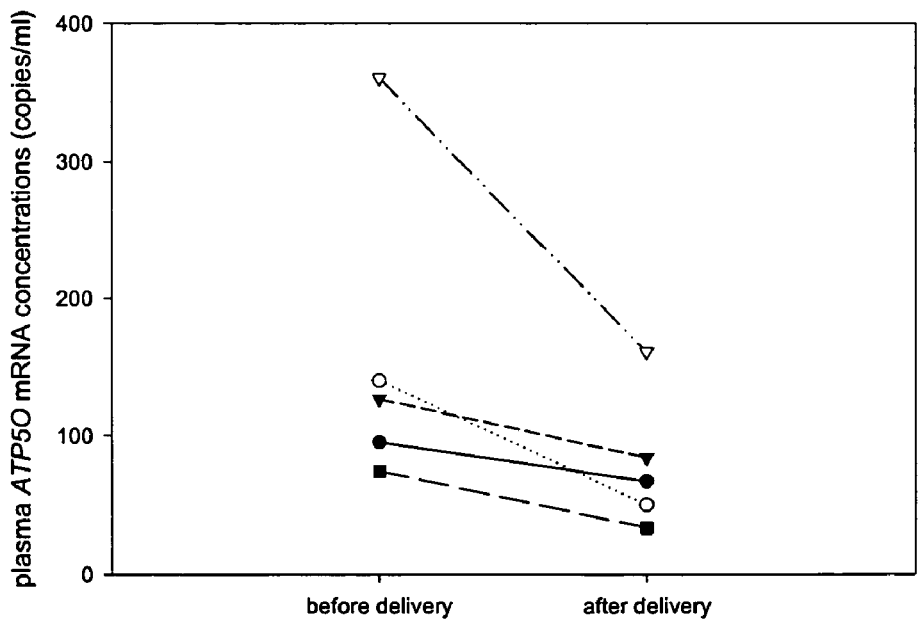

Placenta-expressed chromosome 21 transcripts can be detected in maternal plasma and are pregnancy-specific. The median plasma mRNA concentrations in non-pregnant women, first trimester and third trimester pregnancies were 0 copies/ml, 0 copies/ml and 72.6 copies/ml, respectively, for COL6A1 (FIG. 2A); 25.3 copies/ml, 53.0 copies/ml and 155.6 copies/ml for SOD1 (FIG. 2B); 0.8 copies/ml, 2.1 copies/ml and 8.8 copies/ml for COL6A2, (FIG. 2C); and 6.2 copies/ml, 88.2 copies/ml and 126.4 copies/ml for ATP5O (FIG. 2D). For all of the four transcripts, their plasma concentrations in the third trimester of pregnancy were significantly higher than that in the non-pregnant group (Mann-Whitney Rank Sum test, $P<0.05$ for COL6A1, SOD1, COL6A2 and ATP5O mRNA). Furthermore, in the pre-delivery plasma samples, the median COL6A1, SOD1, COL6A2 and ATP5O mRNA concentrations were 72.6 copies/ml, 155.6 copies/ml, 8.8 copies/ml and 126.4 copies/ml, respectively (FIG. 3A for COL6A1 mRNA, FIG. 3B for SOD1 mRNA, FIG. 3C for COL6A2 mRNA and FIG. 3D for ATP5O mRNA). While in the postpartum plasma samples, the median mRNA concentrations of COL6A1, SOD1, COL6A2 and ATP5O were 0 copies/ml, 56.2 copies/ml, 0.8 copies/ml and 56.2 copies/ml, respectively.

Example 2

Detection of Trisomy 21 in the Fetus of a Pregnant Woman by Real-Time Quantitative RT-PCR The two SNPs with the highest polymorphic rates were selected as targets for allele-specific QRT-PCR development. Discriminative hybridization probes were designed to allow discrimination of the different alleles of each SNP. Identical genotyping results were obtained by both the real-time PCR and direct sequencing which confirmed the allele-specificity of the probes. The probes were then incorporated into QRT-PCR assays where the relative expression levels of the different alleles of each SNP in placental tissues were first measured. RNA extracted from normal CVS and normal term placentas, as well as from placentas of trisomy 21 pregnancies were assayed by the allele-specific QRT-PCR. The ratios of the alleles of each SNP in the pregnancies with and without trisomy 21 are substantially different, enabling the detection of trisomy 21 in the fetus using the mother's plasma.

Sample collection and processing. Placental tissue samples from 13 first trimester and 20 third trimester pregnancies were obtained from pregnant women by chorionic villus sample (CVS) before therapeutic terminations or immediately after elective cesarean delivery, respectively. Placental tissues from seven trisomy 21 pregnancies were also recruited. All tissues were processed as described above.

Development of allele-specific real time QRT-PCR. The two informative coding SNPs with the highest polymorphic rates, rs1053312 (dbSNP Accession numbers) and rs2839114 of the COL6A1 and COL6A2 genes, respectively, were selected. Allele-specific real-time quantitative RT-PCR assays were established for measuring the relative concentrations of the two alleles of each SNP. To allow allelic discrimination, two fluorogenic MGB probes, each specific for one allele, are included in each QRT-PCR assay. The two probes are labeled with either FAM (6-carboxyfluorescein) and VIC fluorescent reporter dyes. The sequences of the primers and probes of the allele-specific QRT-PCR systems are shown in Table 5. Identical genotyping results were obtained by both the real-time PCR and direct sequencing which confirmed the allele-specificity of the probes.

TABLE 5

Sequences of primers and probes for allele-
specific real-time QRT-PCR detection of the
targeted RNA-SNPs.

| Transcripts | dbSNP | | Sequences (5' to 3')[1] | | SEQ ID NO: |
|---|---|---|---|---|---|
| COL6A1 | 1053312 | F primer | GGCAGCCACAACTTTGACAC | | 33 |
| | | R primer | CTCGGCCAGGCGCTT | | 34 |
| | | Probe (allele G) | (VIC) ACCAAGCGCTTCGC (MGBNFQ) | | 35 |
| | | Probe (allele A) | (FAM) ACCAAGCACTTCGC (MGBNFQ) | | 36 |
| COL6A2 | 2839114 | F primer | GGCGCCAGAAGACACGT | | 37 |
| | | R primer | GTCGTGGCGCCCGT | | 38 |
| | | Probe (allele G) | (VIC) TGATGACCACCGCAAA (MGBNFQ) | | 39 |
| | | Probe (allele A) | (FAM) TGATGACTACCGCAAA (MGBNFQ) | | 40 |

[1]VIC and FAM: fluorescent labels; MGBNFQ: minor groove binding non-fluorescent quencher.

The QRT-PCR reactions for allele discrimination and relative quantification were set up according to the procedure set forth above using the PCR primers (Proligo) and the MGB probes (Applied Biosystems) at concentrations of 450 nM and 100 nM, respectively, and 17 ng of placental RNA samples for amplifications. Each QRT-PCR was performed in duplicate in an Applied Biosystems 7700 Sequence Detector. The thermal profile used was that described above using a temperature of 59° C. for the annealing/extension step. Only heterozygous samples were included in the analysis.

Statistical Analysis. Statistical analysis was performed using the Sigma Stat 2.03 software (SPSS).

Relative quantification of chromosome 21 encoded RNA-SNPs. The relative amounts of the two alleles are determined either by the difference in their threshold cycle values ($\Delta Ct$) or by the difference in their accumulated fluorescent intensities ($\Delta\Delta Rn$), as calculated by the following equations:

$$\Delta Ct = Ct_{FAM} - Ct_{VIC}$$

$$\Delta\Delta Rn = \Delta Rn_{FAM} - \Delta Rn_{VIC}$$

where $Ct_{FAM}$ and $Ct_{VIC}$ are the threshold cycle values of allele A (as detected by a FAM-labeled probe) and allele B (as detected by a VIC-labeled probe). $\Delta Rn_{FAM}$ and $\Delta Rn_{VIC}$ are the accumulated fluorescent intensities of allele A and allele B, as calculated by the SDS v1.9 software (Applied Biosystems). The Ct and $\Delta Rn$ values are logarithmically related to the abundance of PCR products, thus the difference in the Ct and $\Delta Rn$ values for each RNA-SNP (the $\Delta Ct$ and $\Delta\Delta Rn$ values) is reflective of the RNA-SNP ratio between the two RNA alleles.

Figure 4:
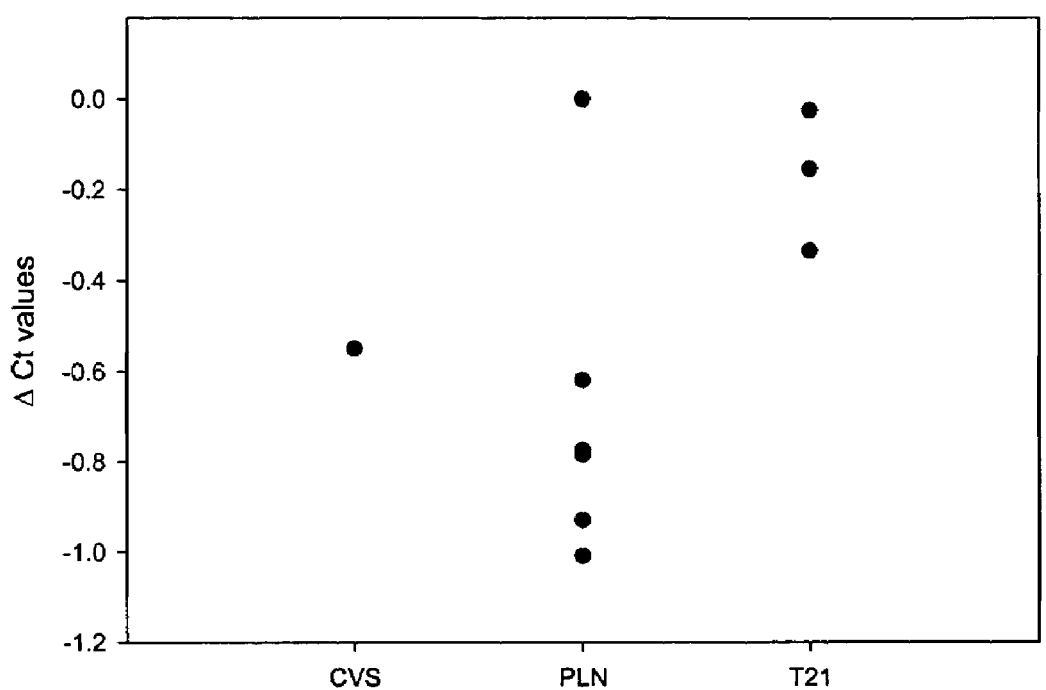
FIG. 4. Ratios between the two transcript alleles for the SNP rs1053312 of COL6A1 gene in placental tissues. The relative quantities between the RNA alleles were determined by allele-specific real-time quantitative RT-PCR. RNA from normal CVS (CVS), normal term placentas (PLN) and trisomy 21 placentas (T21) were assayed. The ratios were calculated by the difference in threshold cycle values ($\Delta$Ct).

For the SNP rs1053312 (COL6A1), one CVS, six term placentas from normal pregnancies and three trisomy 21 placenta samples were heterozygous for the polymorphic site, as determined by the allele-specific QRT-PCR. In FIG. 4, the $\Delta Ct$ values for the three trisomy 21 placentas deviated from the $\Delta Ct$ values of the CVS and term placental tissues obtained from normal pregnancies.

Figure 5:
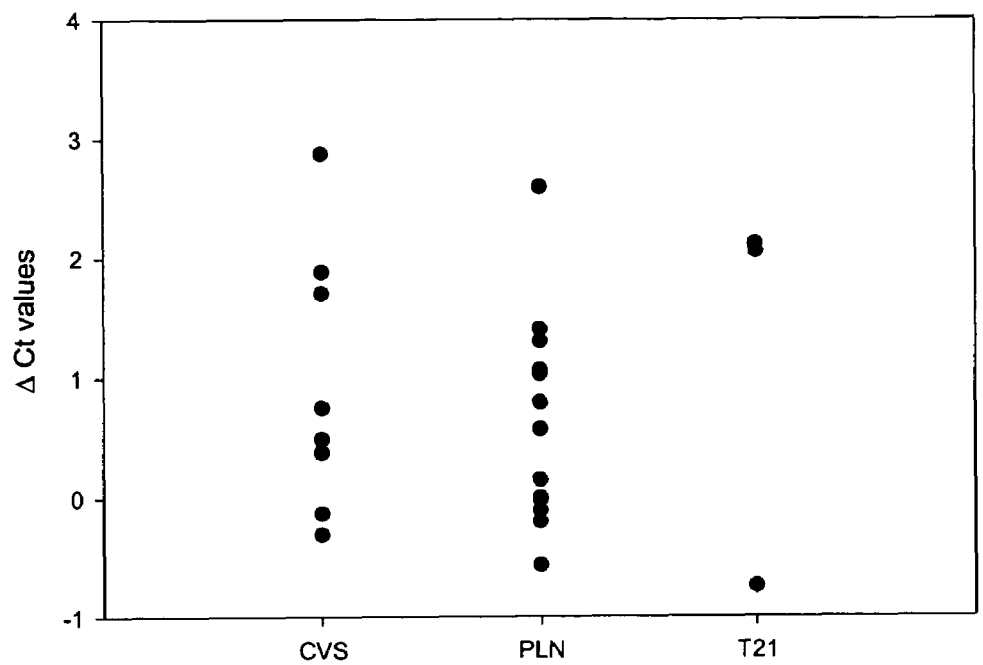
FIG. 5. Ratios between the two transcript alleles for the SNP rs2839114 of COL6A2 gene in placental tissues as determined by allele-specific real-time quantitative RT-PCR. RNA from normal CVS (CVS), normal term placentas (PLN) and trisomy 21 placentas (T21) were assayed. The ratios were calculated either by (A) the difference in threshold cycle values ($\Delta$Ct) or (B) the difference in their fluorescent intensities attained in the last PCR cycle ($\Delta\Delta$Rn).
Figure 5:
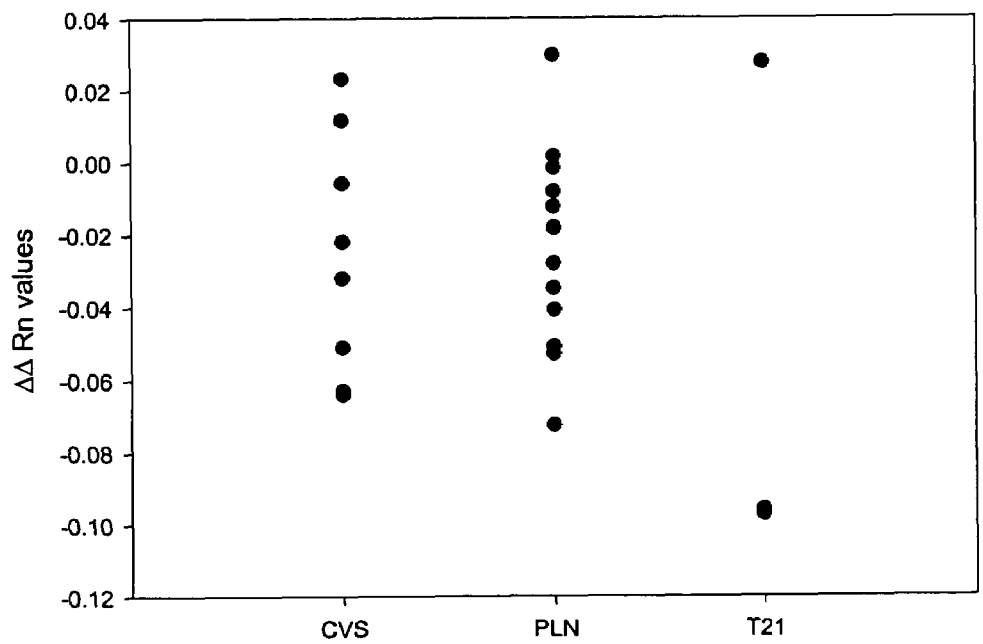

For the SNP rs2839114 (COL6A2), eight CVS and thirteen term placentas from normal pregnancies, as well as three trisomy 21 placentas were heterozygous for the SNP locus as genotyped by the allele-specific QRT-PCR assay. As shown in FIG. 5A, the $\Delta Ct$ values of the three trisomy 21 placentas deviated from those of the normal pregnancies, with two trisomy 21 cases exhibiting greater $\Delta Ct$ values and the remaining case with a reduced value: The deviations of the $\Delta Ct$ values of trisomy 21 placentas may fall either above or below the normal pregnancy range, dependent on which allele is overrepresented. Similar results were obtained by using the $\Delta\Delta Rn$ values (FIG. 5B).

Example 3

Detection of Trisomy 21 in the Fetus of a Pregnant Woman by Primer Extension and Mass Spectrometry Detection The two SNPs with the highest polymorphic rates (rs1053320 on COL6A1 and rs2839114 on COL6A2) were targeted for further assay development. Primer extension reaction assays enabled determination of the SNP genotype of the placental tissue samples. The samples were processed using mass spectrometry to differentiate the different RNA-SNP alleles, and determine the relative expression levels of the RNA-SNP alleles in order to calculate the ratio of alleles. The difference in the ratios of the alleles of each SNP for pregnancies with and without trisomy 21 is sufficiently large that detection of trisomy 21 in the fetus is possible using the mother's plasma.

Placental tissue collection and processing. Second-timester placental tissue samples were obtained from pregnant women carrying trisomy 21 fetuses before therapeutic terminations. Third-trimester placental tissue samples were collected from karyotypically normal fetuses immediately after delivery. The placental tissue samples were divided into two portions, one of which was stored in RNAlater™ (Ambion®, Austin, Tex.) immediately upon collection and kept at −80° C. until RNA extration, while the other portion was immediately kept at −80° C. until DNA extration. DNA was extracted from the placental tissues using the QIAamp mini kit using the tissue protocol according to the manufacturer's instruction (Qiagen, Hilden, Germany). Total RNA from placental tissues were extracted with the Trizol Reagent (Invitrogen, Carlsbad, Calif) and purified with RNeasy mini-kit (Qiagen, Hilden, Germany) following manufacturer's protocols.

Placental DNA and RNA amplification. For RNA amplification, a total of 450 ng of placental RNA was reverse transcribed with random hexamers (TheromScript, Invitrogen) according to manufacturer's instruction. 25 ng of DNA or cDNA corresponding to 50 ng of total RNA was used for each PCR reaction (AmpliTaq Gold, Applied Biosystems). The primer sequences for the amplification of each of the SNP locus on COL6A1and COL6A2 are shown in Table 6. PCR primers were used at 200 nM final concentrations for a PCR volume of 25 μ. The PCR condition was: 95° C. for 10 min, followed by denaturing at 94° C. for 20 sec, annealing at 56° C. for 30 sec, and extension at 72° C. for 1 min for 45 cycles, and finally incubation at 72° C. for 3 min.

Diego, USA) for 40 min at 37° C. followed by 5 min at 85° C. to remove excess dNTPs. A primer extension primer and a mixture of 2',3'-dideoxynucleoside triphosphates (ddNTPs) and dNTPs were added to the treated PCR products. Sequences for the primer extension primer designed to interrogate the chosen SNP on COL6A1 and COL6A2 are shown in Table 7. A thermoSequenase (Sequenom) was used for the base extension reactions using standard MassARRAY™ Homogeneous MassEXTEND™ (hME) assay protocol from Sequenom. The base extension condition was: 94° C. for 2 min, followed by 94° C. for 5 sec, 52° C. for 5 sec, and 72° C. for 5 sec for 75 cycles. Sequences of the primer extended products for each SNP allele are shown in Table 7. The final extension products were treated with SpectroCLEAN (Sequenom) resin to remove salts in the reaction buffer. Approximately 10 nL of reaction solution was dispensed onto a 384-format SpectroCHIP (Sequenom) using a SpectroPoint (Sequenom) nanodispenser. A compact MALDI-TOF mass

TABLE 6

Primer sequences for the amplification of the SNP loci on COL6A1 and COL6A2.

| Transcripts | SNP | | Sequences (5' to 3') | SEQ ID NO: |
|---|---|---|---|---|
| COL6A1 | rs1053320 | F primer | ACGTTGGATGCTATGTGACCCGCTTCTACC | 41 |
| | | R primer | ACGTTGGATGGAGTTGCCATCTGAGAAGAG | 42 |
| COL6A2 | rs2839114 | F primer | ACGTTGGATGACCGCCTCATCAAGGAGAGC | 43 |
| | | R primer | ACGTTGGATGAAGTTGAGGTCATCGTCCCG | 44 |

SNP detection by primer extension reaction. Primer extension reaction assays were designed to determine the SNP genotype of the placental tissue samples. The placental RNA-SNP genotypes were compared with that obtained for placental DNA. The placental DNA and RNA PCR products were treated with shrimp alkaline phosphatase (Sequenom, San spectrometer (Bruker) was used for data acquisitions. The expected molecular weights of all relevant peaks are calculated before the analysis (Table 7) and identified from the mass spectrum. The SNP genotype is determined by scoring the presence or absence of the mass signals corresponding to a particular SNP allele.

TABLE 7

Sequences of the primer extension primers and expected sequences and molecular masses of the extended products for the respective SNP alleles for rs1053320 on COL6A1 and rs2839114 on COL6A2.

| Transcripts | SNP | | Extended Sequences[1] | SEQ ID NO: | Mass (Da) |
|---|---|---|---|---|---|
| COL6A1 | rs1053320 | un-extended | CTCTTCTTGGCAGCGCC | 45 | 5113.3 |
| | | allele T | CTCTTCTTGGCAGCGCCA | 46 | 5410.5 |
| | | allele C | CTCTTCTTGGCAGCGCCGGA | 47 | 6068.9 |
| COL6A2 | rs2839114 | un-extended | AAGACACGTGTGTTTGCGGT | 48 | 6188.0 |
| | | allele A | AAGACACGTGTGTTTGCGGTA | 49 | 6485.2 |
| | | allele G | AAGACACGTGTGTTTGCGGTGGT | 50 | 7134.6 |

[1]Bold fonts indicate the extended dNTPs and ddNTPs.

Figure 6:
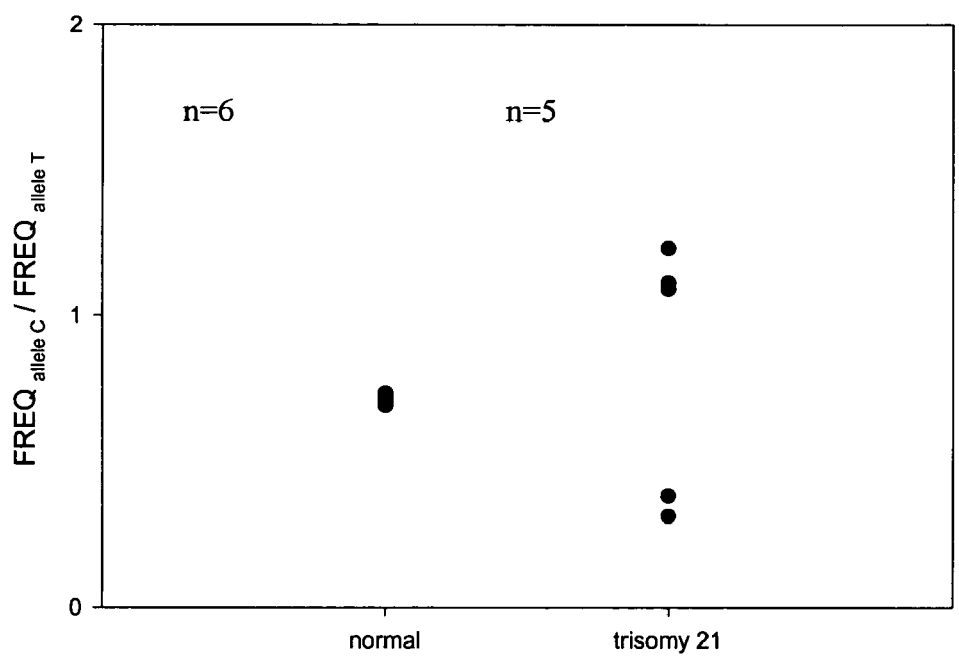
FIG. 6. Ratios of allelic frequencies of SNP rs1053320 (COL6A1) in placentas of heterozygous normal and trisomy 21 fetuses determined by primer extension followed by mass spectrometry analysis. (A) Placental DNA. (B) Placental RNA.
Figure 6:
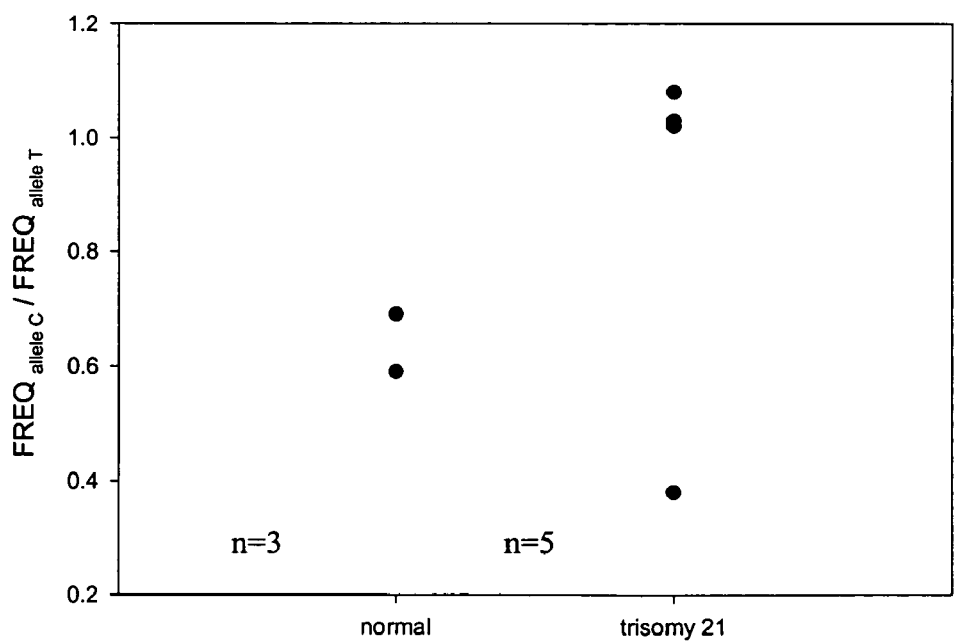
Figure 7:
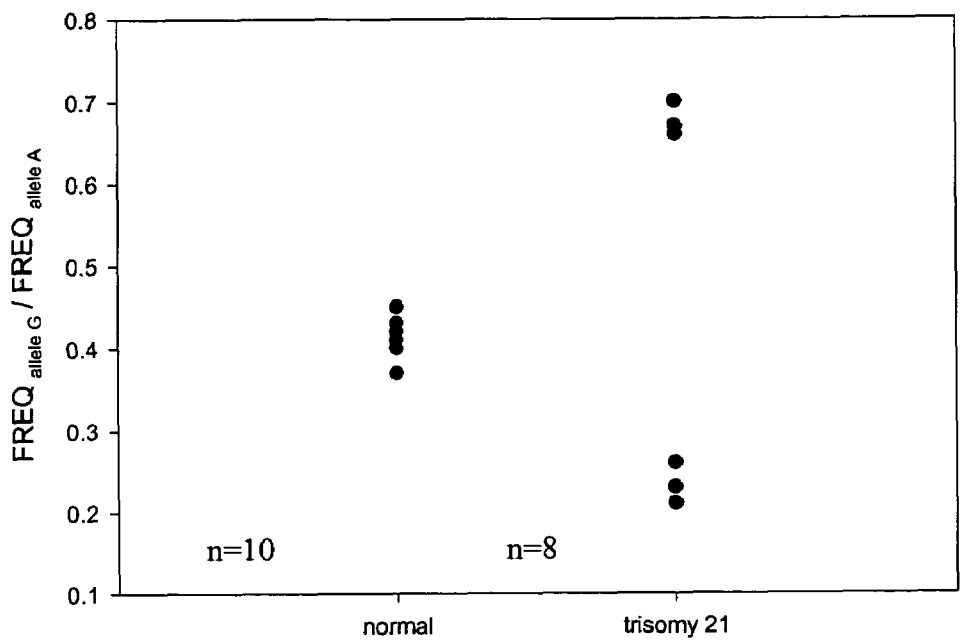
FIG. 7. Ratios of allelic frequencies of SNP rs2839114 (COL6A2) in placentas of heterozygous normal and trisomy 21 fetuses determined by primer extension followed by mass spectrometry analysis. (A) Placental DNA. (B) Placental RNA.
Figure 7:
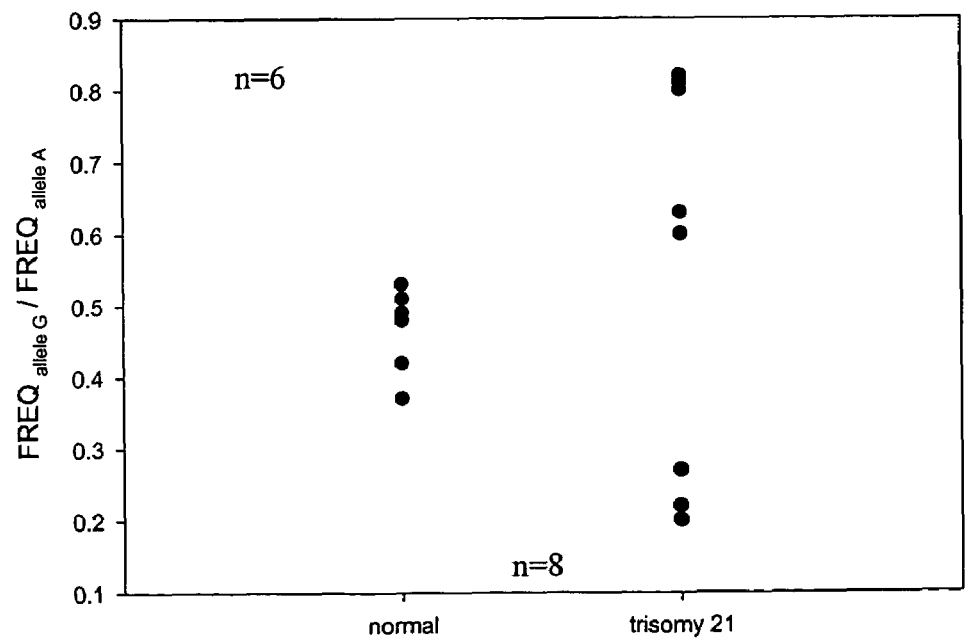

Determination of SNP ratio. Mass spectrometric data were automatically imported into the SpectroTYPER (Sequenom) database for automatic analysis. The ratio of the peak frequency of the mass signals for the two SNP alleles in fetuses heterozygous for the interrogated SNP was determined. The SNP ratio obtained for karyotypically normal and trisomy 21 fetuses were compared. The placental DNA SNP ratio of the trisomy 21 fetuses deviated from that obtained for the normal fetuses for the SNPs on both COL6A1 (FIG. 6A) and COL6A2 (FIG. 7A). The SNP-ratio for the trisomy 21 fetuses would either be decreased or increased compared with that of the normal fetuses depending on the SNP genotype of the trisomic chromosome 21. The placental tissue SNP ratio of the interrogated SNPs on COL6A1 (FIG. 6B) and COL6A2 (FIG. 7B) RNA transcripts for the trisomy 21 fetuses was also shown to deviate from that obtained for normal fetuses.

Example 4

Non-Invasive Prenatal Detection of Trisomy 21 Fetus Using Circulating Fetal RNA in Maternal Plasma by Primer Extension and Mass Spectrometry In order to demonstrate that additional SNPs are also useful for the detection of chromosomal disorders in the fetus of a pregnant woman, placenta-specific 4 (PLAC4) (Table 19) was investigated. Primer extension reaction assays enabled determination of the RNA-SNP genotype of the placental tissue and maternal plasma samples. The primer extension products were analyzed using mass spectrometry to quantify the RNA-SNP allele ratios. The difference in the ratios of the alleles of a PLAC4 SNP for pregnancies with and without trisomy 21 is sufficiently great so that detection of trisomy 21 of the fetus is possible using the mother's plasma.

Identification of Applicable Coding SNPs in Placenta-Specific 4 (PLAC4) Gene and Determination of Allele Frequencies SNP identification. The placenta-specific 4 (PLAC4) gene is highly expressed in the placenta, but expressed at low levels in the buffy coat cells. The PLAC4 gene is located in the Down syndrome critical region of chromosome 21. The PLAC4 gene sequence is listed in Table 19 and spans the nucleotide coordinates 41469028-41480585 on chromosome 21 based on the Human May 2004 (hg17) assembly at the UCSC Genome Browser (genome.ucsc.edu/). The PLAC4 gene sequence as listed in Table 19 consists of all known and predicted PLAC4 RNA splicing variants identified by the GenBank accession numbers: AF269287, AK027868, AK092431, BC093685, BC101615, BC101617, L13197, NM_182832 and LOC191585. Polymorphic SNPs were identified by sequencing the exonic/transcribed regions of the PLAC4 gene. Direct sequencing was performed on placental DNA samples from 10 unrelated Chinese pregnant women. Twenty nanograms of genomic DNA was first amplified by PCR. Sequencing was performed using BigDye Terminator Cycle Sequencing v1.1 (Applied Biosystems, Foster City, Calif.) and a Model 3100 DNA Analyzer (Applied Biosystems).

Allele frequency determination. Four coding SNPs in the transcribed region of PLAC4 were found to be polymorphic in the Chinese population (Table 8). These four SNPs are located at the chromosome 21 nucleotide positions 41470591, 41471145, 41476236 and 41478755, respectively, of the chromosome 21 sequence of the Human May 2004 (hg17) assembly at the UCSC Genome Browser (genome.ucsc.edu/). The dbSNP accession numbers for the SNPs found at the chromosome 21 nucleotide positions 41470591 and 41478755 are rs9977003 and rs8130833, respectively. The remaining two SNPs were novel ones which are hereby named as PLAC4-41471145 and PLAC4-41476236, according to their nucleotide coordinates on chromosome 21 on the Human May 2004 (hg17) assembly at the UCSC Genome Browser (genome.ucsc.edul). Their allele frequencies are shown in Table 9. rs8130833 was the most polymorphic SNP among the four SNPs and was selected for further assay development.

TABLE 8

Four polymorphic SNPs located in the coding region of PLAC4.

| SNP | Sequence | SEQ ID NO: |
|---|---|---|
| PLAC4-41478755[1] (rs8130833)[2] | 5'- TTTTACAAAATAAGCCTAATCGTAAAATATCACTATAGTATATAGAACCATGTTTAGGCC AGATATATTCGTC[A/G]TCTAACTTGTATTTAACCCAAATGGTGTTGCAATACAAAATGAGTT TCTTTTTCTTTAAGCCAAATTTGAATTTGCTCCAATAGCTTAAAAGACACCCTAGCGGCG -3' | 51 |
| PLAC4-41471145[1] | 5'- CTCACATCTCTAAAGGCCACTCAGGTGGGACACCATCAAGACATTGAAAATCGACAGAAG GAAGGCAGGAAGGGGAGAGGATC[A/G]AACCTGTCAAAATAGATATTCAGAAAATCTGTGCTC TAAAATAAGGCAGCCCTTCCCTCACAGCACACTTATTCCTAATTTCAACAGGACTCCTAG -3' | 52 |
| PLAC4-41470591[1] (rs9977003)[2] | 5'- TCATTCTGAGGCGGTGCTGCTGAAAATCTTGGTGCTGAACGTGTGTTTTTGAGATTTCCA GTCTATCAC[A/G]GGGCCACAAGGTGTAAATATCAAGAAAAATGAATTACTAGAAAGGCAAAG TGAAAAAGACATACAAAATACAAGTGTCATTCTTTTTATTCTTAGTTTGGACAGATAGTC -3' | 53 |
| PLAC4- | 5'- TAATTGATTCTTGGGGTATCCCTGTCTTTACCCTGTCTTTAAGGTTTTAGCAAGACTAAG | 54 |

TABLE 8-continued

Four polymorphic SNPs located in the coding region of PLAC4.

| SNP | Sequence | SEQ ID NO: |
|---|---|---|
| 41476236[1] | TCTCCTGGTTGAAC[C/T]GGGGAGCTATTTTTTCCTTTGTGGGGAAGGACAGTATTTTATTTT TATATTGGAGGGCCTTTTGAACCTGTCCTAAATTCTAAAGGGGAGGGGGGAAGGTTCATA -3' | |

The PLAC4 mRNA was transcribed in the reverse direction of the sequences showed in the table.
[1]The number marks the location of the SNP based on the Human May 2004 (hg17) assembly at the UCSC Genome Browser (genome.ucsc.edu/).
[2]dbSNP accession number

TABLE 9

Allele frequencies of four PLAC4 coding SNPs in placental DNA samples of 10 unrelated Chinese pregnant women.

| SNP | rs8130833 | PLAC4-41471145 | rs9977003 | PLAC4-41476236 |
|---|---|---|---|---|
| Allele | G/A | A/G | A/G | T/C |
| f (minor allele) | 0.25 | 0.10 | 0.10 | 0.10 |
| Heterozygosity | 0.38 | 0.18 | 0.18 | 0.18 |

For each SNP, the minor allele is listed first.
"f (minor allele)" denotes the frequency of the minor allele.

Determination of Allelic Ratios of PLAC4 RNA in Maternal Plasma Using a SNP Marker Sample collection and processing. First- and second-trimester placental tissue samples were obtained from seven pregnant women carrying trisomy 21 fetuses. Placental tissues from 26 pregnant women carrying karyotypically normal fetuses were also collected by chorionic villus sampling (CVS). The placental samples were stored in RNAlater™ (Ambion®, Austin, Tex.) immediately upon collection and kept at −80° C. until RNA extraction. Peripheral blood samples were collected from 43 pregnant women carrying a single euploid fetus and five pregnant women carrying a single trisomy 21 fetus during their first-trimester of pregnancy. Plasma samples were harvested as described in Example 1.

Total RNA from the placental tissues was extracted with Trizol (Qiagen, Hilden, Germany) following the manufacturer's protocol. RNA was extracted from 1.6 to 3.2 ml of the maternal plasma samples. For every milliliter of plasma, 3 ml of Trizol LS reagent and 0.8 ml of chloroform were added. The mixture was centrifuged at 12,000×g for 15 min at 4° C. After centrifugation, the aqueous layer was collected. Five hundred and thirty-eight microliters of absolute ethanol was added per 1 ml of aqueous layer. The mixture was applied to the RNeasy mini columns (Qiagen, Hilden, Germany) and were processed according to manufacturer's recommendations. Total RNA was eluted with 48 µl of RNase-free water for each column. The final eluted RNA from the two columns was pooled together. DNase treatment was then carried out to remove any contaminating DNA (Invitrogen, Carlsbad, Calif., USA).

Reverse transcription and PCR amplification. 1.25 micrograms of placental RNA or 48 µL of plasma RNA was reverse transcribed in a reaction volume of 40 µl or 100 µl, respectively, according to manufacturer's instructions (ThermoScript, Invitrogen, Carlsbad, Calif., USA), using gene-specific primers (sequences are shown in Table 10).

For each PCR amplification reaction, 40 µl of the placental cDNA or 100 µl of the maternal plasma cDNA was used in a total volume of 80 µl or 200 µl respectively. Each reaction contained 0.6X HotStar Taq PCR buffer with 0.9 mM MgCl2 (Qiagen), 25 µM each of dATP, dGTP and dCTP, 50 µM of dUTP (Applied Biosystems), 200 nM each of forward and reverse primers (Integrated DNA Technologies) and 0.02 U/µl of HotStar Taq Polymerase (Qiagen). The PCR primer sequences are shown in Table 10. The PCR reaction was initiated at 95° C. for 7 min, followed by denaturation at 95° C. for 40 sec, annealing at 56° C. for 1 min, extension at 72° C. for 1 min for 55 cycles, and a final incubation at 72° C. for 3 min.

TABLE 10

Primer sequences for reverse transcription and PCR amplification of the sequence containing SNP rs8130833.

| Primer | Sequence (5' to 3') | SEQ ID NO: |
|---|---|---|
| Gene-specific primer for reverse transcription | GTATATAGAACCATGTTTAGGCCAG | 55 |
| Forward PCR primer | ACGTTGGATGGTATTGCAACACCATTTGGG | 56 |
| Reverse PCR primer | ACGTTGGATGTAGAACCATGTTTAGGCCAG | 57 |

SNP detection and allelic ratio quantification by primer extension reaction. The primer extension reaction was performed as was described in Example 3. The PCR product was first treated with shrimp alkaline phosphatase (Sequenom, San Diego, USA). Four microliters of base extension cocktail containing 771 nM of extension primer (Integrated DNA Technologies), 1.15 U of Thermosequenase (Sequenom) and 64 µM each of ddATP, ddCTP, ddTTP and dGTP (Sequenom, San Diego, USA) were mixed with 5 µl of water and 5 µl of the PCR product. The thermal profile was 94° C. for 2 min, followed by 94° C. for 5 sec, 52° C. for 5 sec, and 72° C. for 5 sec for 100 cycles. Sequences and molecular weights for the extension primer and the extension products for each SNP allele are shown in Table 11. The molecular weights of the final extension products were determined by MALDI-TOF mass spectrometer as was described in Example 3. The ratios of the peak areas for the primer extension products representing the two SNP alleles in fetuses heterozygous for the SNP were determined.

TABLE 11

Sequences and molecular weights of the extension primer and the expected extension products for SNP rs8130833.

| | Sequence | SEQ ID NO: | Molecular Weight (Da) |
|---|---|---|---|
| Unextended primer | AGGCCAGATATATTCGTC | 58 | 5498.6 |
| Extension product for allele A | AGGCCAGATATATTCGTCA | 59 | 5795.8 |
| Extension product for allele G | AGGCCAGATATATTCGTCGT | 60 | 6116.0 |

Letters in bold font indicate the dNTPs and ddNTPs residues added to the extension primer.

Development of Real-Time QRT-PCR Assay

A QRT-PCR assay for PLAC4 mRNA was developed to assess if there are quantitative differences in maternal plasma PLAC4 mRNA concentrations between trisomy 21 and normal pregnancies. The sequences of the primers (Integrated DNA Technologies, Coralville, IA), TaqMan minor groove binding (MGB) fluorescent probes (Applied Biosystems, Foster City, CA, USA) and the calibrator (Proligo, Singapore) are shown in Table 12.

TABLE 12

Sequences of the PCR primers, the probe and the calibrator for real-time QRT-PCR detection of PLAC4 mRNA.

| Primer | Sequence (5' to 3') | SEQ ID NO: |
|---|---|---|
| F primer | CCTTTCCCCCTTATCCAACT | 61 |
| R primer | GTACTGGTTGGGCTCATTTTCT | 62 |
| Probe | (FAM) CCCTAGCCTATACCC (MGBNFQ) | 63 |
| Calibrator | CACCTTTCCCCCTTATCCAACTAGCCCTAGCCTATACCCTCTGCTGCCCA AGAAAATGAGCCCAACCAGTACAC | 64 |

MGBNFQ: minor groove binding non-fluorescent quencher

The QRT-PCR reactions were set up according to the manufacturer's instructions (EZ rTth RNA PCR reagent set, Applied Biosystems) in a reaction volume of 25 μl. The QRT-PCR assays were carried out in an ABI PRISM® 7900HT (Applied Biosystems, Foster City, Calif., USA). The PCR primers and the fluorescent probe were used at concentrations of 400 nM and 100 nM, respectively. 5 μl of extracted RNA were used for amplification. The thermal cycling profile was: the reaction was initiated at 50° C. for 2 min, followed by reverse transcription at 60° C. for 30 min. After a 5-min denaturation at 95° C., 45 cycles of PCR were carried out using denaturation at 95° C. for 15 s and 1 min at 60° C.

Figure 8:
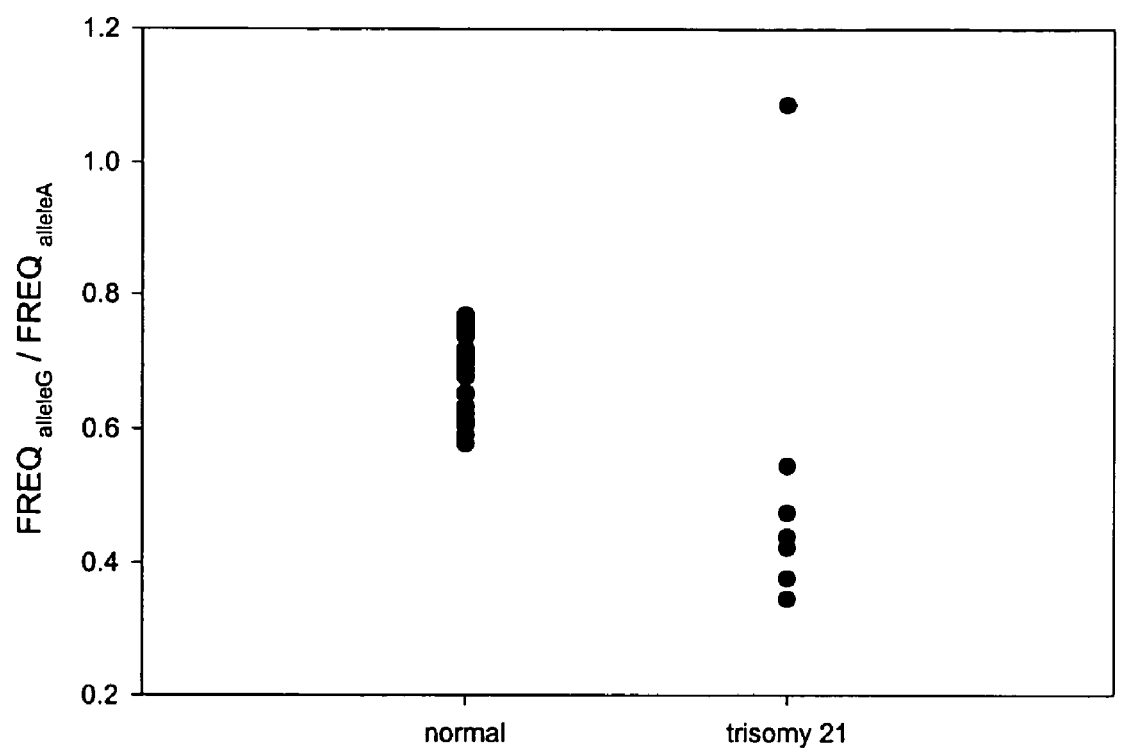
FIG. 8. PLAC4 transcript allelic ratios in placentas of pregnant women carrying normal and trisomy 21 fetuses. The allelic ratios were determined by primer extension followed by mass spectrometry analysis using SNP rs8130833.

Detection of Difference in PLAC4 RNA Allelic Ratio in Placentas and Maternal Plasma Samples from Pregnant Women with Trisomy 21 and Normal Fetuses The RNA transcript allelic ratios in the placentas of karyotypically normal and trisomy 21 pregnancies were compared using the SNP rs8130833. The ratios were calculated by dividing the relative amount of allele G (higher-mass allele, i.e., the allele whereby the extension product demonstrates a higher mass in the mass spectra) to the relative amount of allele A (lower-mass allele, i.e., the allele whereby the extension product demonstrates a lower mass in the mass spectra). As shown in FIG. 8, all trisomy 21 samples showed allelic ratios well distinguishable from the normal samples. The allelic ratios of the trisomy 21 samples segregated into two groups. Trisomy samples with an extra G allele showed an allelic ratio higher than the normal range, while samples with an extra A allele showed an allelic ratio lower than the normal range.

Figure 9:
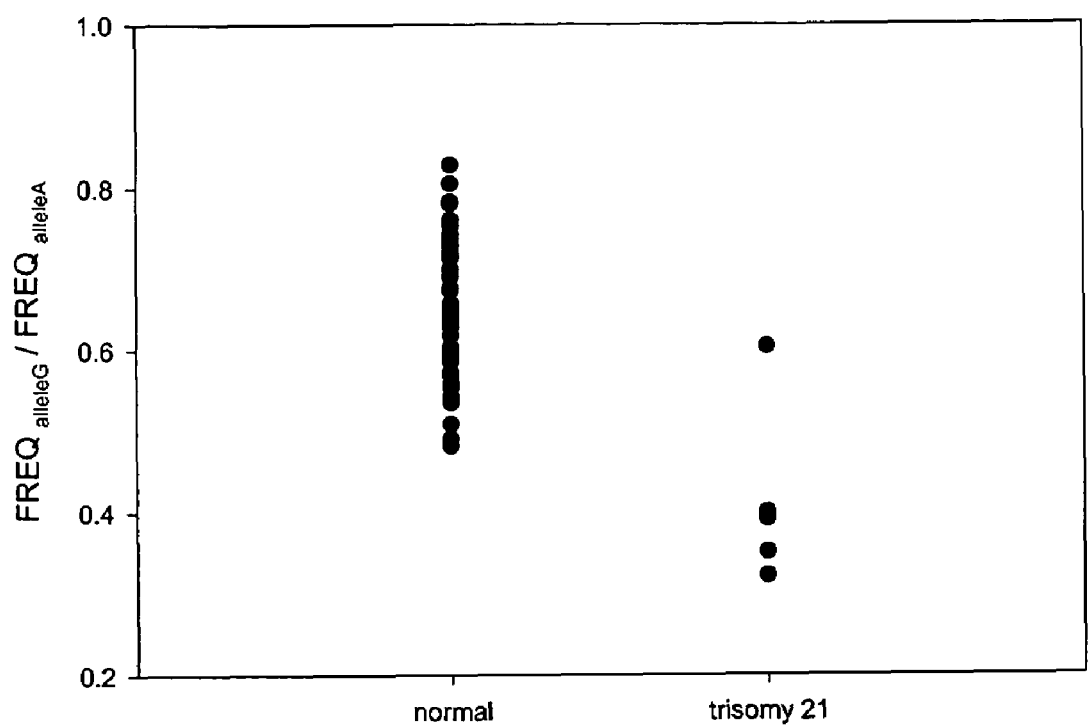
FIG. 9. PLAC4 transcript allelic ratios in the plasma samples of pregnant women carrying normal and trisomy 21 fetuses.

The PLAC4 mRNA allelic ratios were also compared in maternal plasma from women carrying karyotypically normal and trisomy 21 fetuses using the SNP rs8130833. All but one trisomy sample demonstrated allelic ratios that deviated from the normal samples (FIG. 9). The data show that fetal aneuploidy can be detected non-invasively by analyzing the allelic ratios of circulating fetal-specific transcripts in maternal plasma by using polymorphic markers such as SNP.

Figure 10:
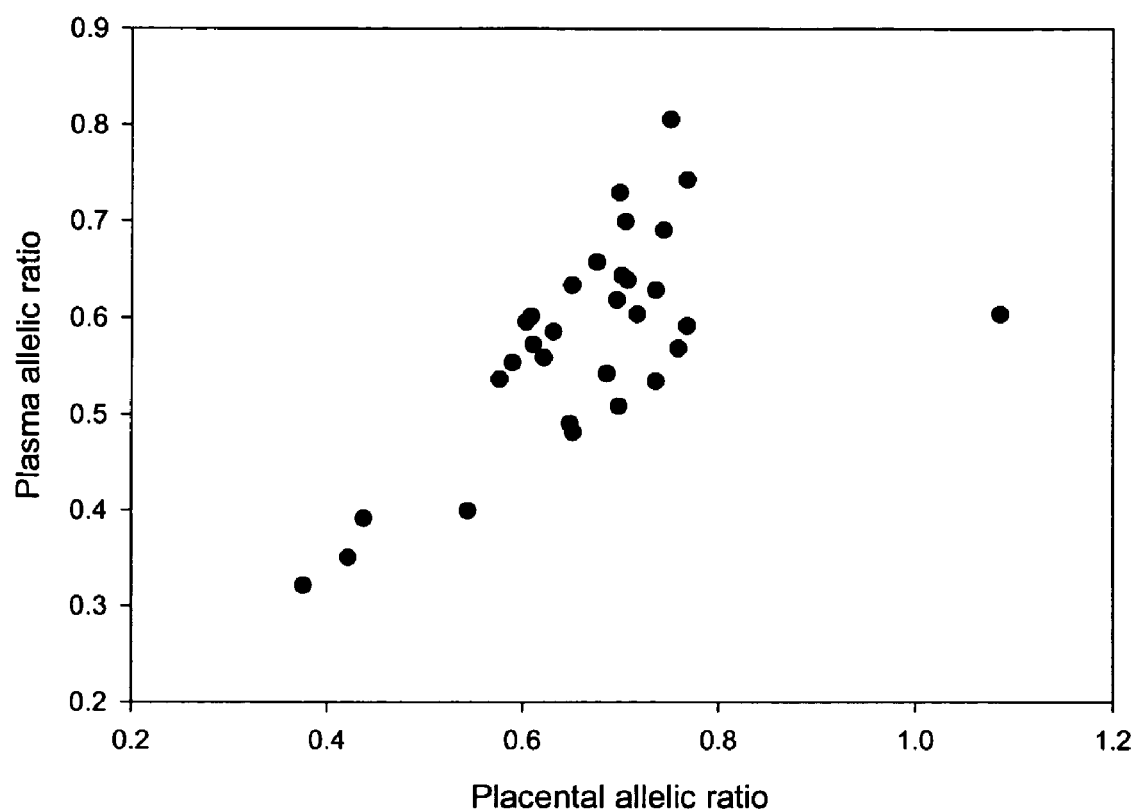
FIG. 10. Correlation of allelic ratios of the PLAC4 transcript from placentas and maternal plasma samples.

A positive correlation was found for the SNP rs8130833 allelic ratio between the placental PLAC4 RNA and the circulating PLAC4 RNA in the maternal plasma (FIG. 10) (Pearson correlation, P<0.05). This finding provides additional evidence that the placenta is a major source for releasing PLAC4 mRNA into maternal plasma.

Comparison of Circulating PLAC4 mRNA in Euploid and Trisomy 21 Pregnancies

Figure 11:
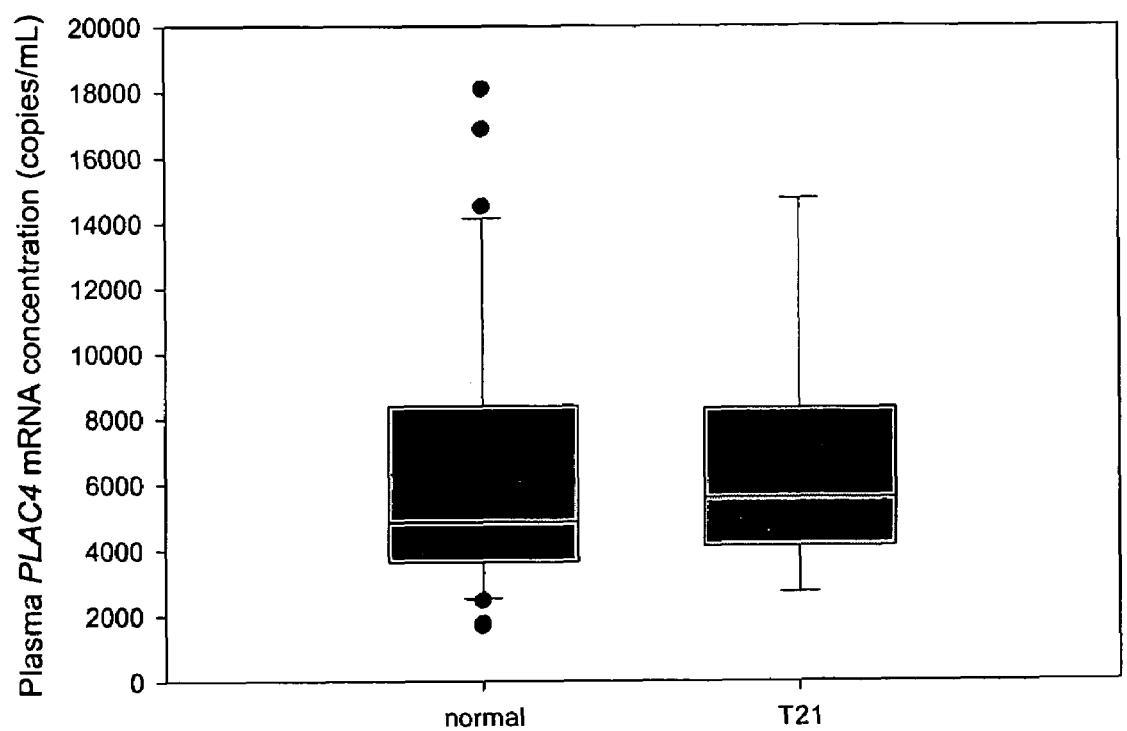
FIG. 11. Comparison of maternal plasma PLAC4 mRNA concentration in trisomy 21 and control pregnancies. The boxes mark the interval between the 25th and 75th percentiles. The whiskers denote the interval between the 10th and 90th percentiles. The filled circles mark the data points outside the 10th and 90th percentiles.

Circulating PLAC4 mRNA concentrations were compared between karyotypically normal and trisomy 21 pregnancies. Plasma samples were collected from 29 pregnant women carrying euploid fetuses and five pregnant women carrying trisomy 21 fetuses during the first- and second-trimester of pregnancy. The plasma samples were measured for PLAC4 mRNA concentrations by real-time one-step RT-PCR as described. As shown in FIG. 11, PLAC4 mRNA was detected in all of the trisomic plasma samples. The medians for the trisomy 21 and normal pregnancies are 5581 copies/ml and 4836 copies/ml, respectively. No statistically significant difference was established for the plasma PLAC4 mRNA concentrations between the normal and the trisomy 21 pregnancies. This demonstrates that the mere quantification of PLAC4 mRNA in maternal plasma does not provide a reliable assessment of the presence of fetal trisomy 21.

Example 5

Detection of Trisomy 18 Fetus Using Fetal-Expressed RNA in Placentas by Primer Extension and Mass Spectrometry In order to demonstrate that additional chromosomal disorders can be detected using other genes, serpin peptidase inhibitor clade B (ovalbumin) member 2 (SERPINB2) (GenBank Accession number: NM_002575) was investigated for the ability to detect trisomy 18. Primer extension reaction assays enabled determination of the SNP genotype of the placental tissue samples. The samples were processed using mass spectrometry to differentiate the different RNA-SNP alleles, and determine the relative expression levels of the RNA-SNP alleles in order to calculate the ratio of alleles. The difference in the ratios of the alleles of a SERPINB2 SNP for pregnancies with and without trisomy 18 is sufficiently great that detection of trisomy 18 in the fetus is possible using placental RNA samples.

Determination of Allelic Ratio of Serpin Peptidase Inhibitor Clade B (Ovalbumin) Member 2 mRNA in Placentas The placental-expressed serpin peptidase inhibitor dade B (ovalbumin) member 2 (SERPINB2) was chosen. The SERPINB2 gene is located on chromosome 18. A polymorphic SNP (Table 13) located within the coding region of SERPINB2 gene was identified from a public database and was chosen for assay development.

TABLE 13

A polymorphic SNP within the coding region of SERPINB2 gene (SEQ ID NO:65).

| SNP | Sequence |
| --- | --- |
| SERPINB2 (rs6098)[1] | 5'- GTTCTGTGTTATATATAAAGAATTCCTTCTTTCTTTTCAAGGCACAAGCTGCAGATAAAAT CCATTCATCCTTCCGCTCTCTCAGCTCTGCAATCAATGCATCCACAGGG[A/G]ATTATTTACTG GAAAGTGTCAATAAGCTGTTTGGTGAGAAGTCTGCGAGCTTCCGGGAAGTAAGTGAAACCTG -3' |

[1] dbSNP accession number

Sample collection and processing. First- and second-trimester placental tissue samples were obtained from four pregnant women carrying trisomy 18 fetuses. Placental samples from eight first-trimester pregnant women carrying karyotypically normal fetuses were also collected by chorionic villus sampling (CVS). The samples were stored in RNAlater™ (Ambion®, Austin, Tex.) immediately upon collection and kept at −80° C. until RNA extraction. Total RNA was extracted using Trizol (Qiagen, Hilden, Germany) following the manufacturer's protocol. The extracted RNA sample was treated with DNase (Invitrogen, Carlsbad, Calif., USA) to remove any contaminating DNA.

Reverse transcription and PCR amplification. 0.625 micrograms of placental RNA was reverse transcribed in a reaction volume of 20 µl according to manufacturer's instructions (ThermoScript, Invitrogen, Carlsbad, Calif., USA). The reverse transcription was performed using the reverse PCR primer with sequence shown in Table 14.

For PCR amplification, 20µl of the placental cDNA was used in a total reaction volume of 40 µl Each reaction contained 0.6X HotStar Taq PCR buffer with 0.9 mM MgCl$_2$ (Qiagen), 25 µl each of dATP, dGTP and dCTP, 50 µM of dUTP (Applied Biosystems), 200 nM each of forward and reverse primers (Integrated DNA Technologies) and 0.02 U/µl of HotStar Taq Polymerase (Qiagen). The PCR primer sequences are shown in Table 14. The PCR reaction was initiated at 95° C. for 7 min, followed by denaturation at 95° C. for 40 sec. annealing at 56° C. for 1 min, extension at 72° C. for 1 min for 50 cycles, and a final incubation at 72° C. for 3 min.

TABLE 14

Primer sequences for reverse transcription and PCR amplification of the SERPINB2 gene.

| Primer | Sequence (5' to 3') | SEQ ID NO: |
| --- | --- | --- |
| Forward PCR primer | ACGTTGGATGTGATGCGATTTTGCAGGCAC | 66 |
| Reverse PCR primer | ACGTTGGATGCAGACTTCTCACCAAACAGC | 67 |

SNP detection by primer extension reaction. The primer extension reaction was performed as described in Example 3. The PCR product was first treated with shrimp alkaline phosphatase (Sequenom, San Diego, USA). Four microliters of base extension cocktail containing 771 nM of extension primer (Integrated DNA Technologies), 1.15U of Thermosequenase (Sequenom) and 64μl M each of ddATP, ddCTP, ddTTP and dGTP (Sequenom, San Diego, USA) were mixed with 5μl of water and 5μl of the PCR product. The thermal profile was 94° C. for 2 min, followed by 94° C. for 5 sec, 52° C. for 5 sec, and 72° C. for 5 sec for 85 cycles. Sequences of the primer extension products for each SNP allele are shown in Table 15. The molecular weights of the final extension products were detected by the MALDI-TOF mass spectrometer as described in Example 3. The ratios of the peak frequencies for the two SNP alleles in fetuses heterozygous for the SNP were determined.

Example 6

Detection of Trisomy 13 Fetus Using Fetal-Expressed RNA in Placentas by Primer Extension and Mass Spectrometry In order to demonstrate that additional chromosomal disorders can be detected using other genes, collagen type IV alpha 2 (COL4A2) (GenBank Accession number: X05610) was investigated for the ability to detect trisomy 13. Primer extension reaction assays enabled determination of the SNP genotype of the placental tissue samples. The samples were processed using mass spectrometry to differentiate the different RNA-SNP alleles, and determine the relative expression levels of the RNA-SNP alleles in order to calculate the ratio of

TABLE 15

Sequences and molecular weights of the extension primer and the expected extension products for the coding SNP of SERPINB2 gene.

| | Sequence | SEQ ID NO: | Mass (Da) |
|---|---|---|---|
| Unextended primer | TCAATGCATCCACAGGG | 68 | 5179.4 |
| Extension product for allele A | TCAATGCATCCACAGGGA | 69 | 5476.6 |
| Extension product for allele G | TCAATGCATCCACAGGGGA | 70 | 5805.8 |

Letters in bold font indicate the dNTPs and ddNTPs residues added to the extension primer.

Figure 12:
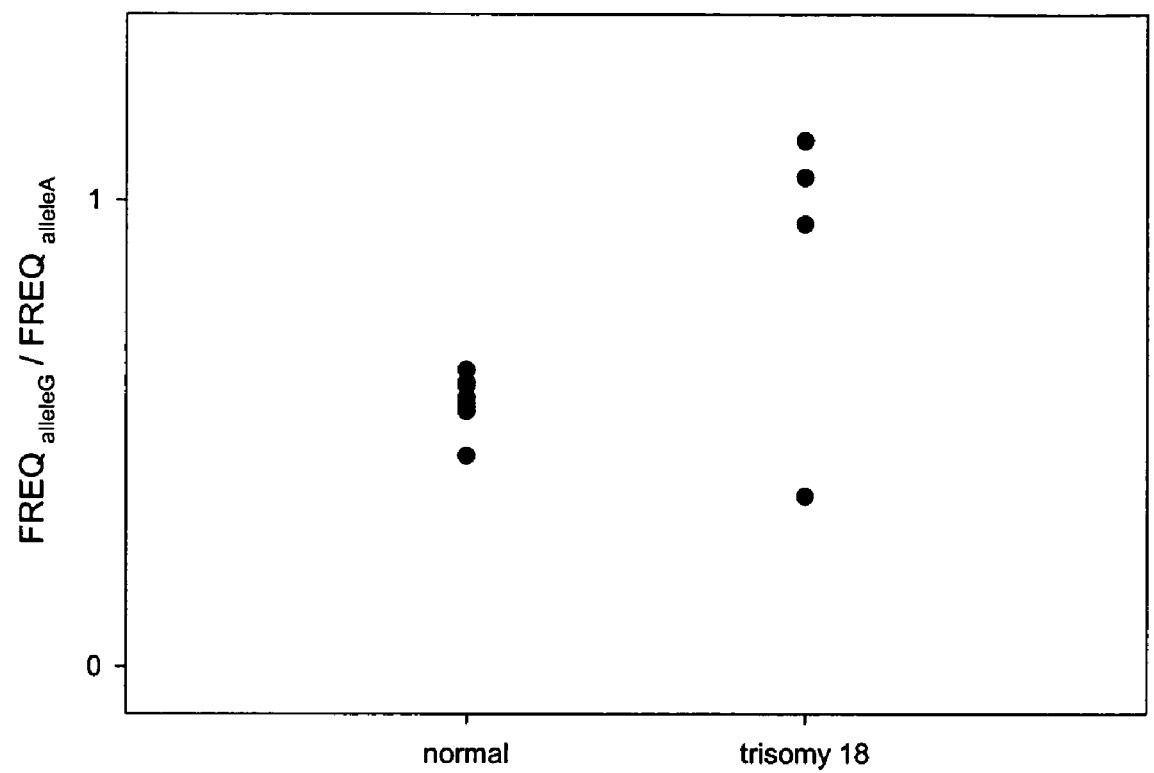
FIG. 12. SERPINB2 transcript allelic ratios in placentas of pregnant women carrying normal and trisomy 18 fetuses. The allelic ratios were determined by primer extension followed by mass spectrometry analysis using SNP rs6098.

Deviation of Allelic Ratios of SERPINB2 Transcripts in the Trisomy 18 Placentas from the Normal Placentas The SNP ratios of SERPINB2 mRNA in the placentas of karyotypically normal and trisomy 18 pregnancies were compared. The ratio was calculated by dividing the relative amount of allele G (higher-mass allele) to the relative amount of allele A (lower-mass allele). As shown in FIG. 12, all trisomy 18 samples showed allelic ratios that deviated from the normal samples without overlapping. The allelic ratios of the trisomy 18 samples segregated into two groups. Trisomy 18 samples with an extra G allele showed allelic ratios higher than the normal range, while a sample with an extra A allele showed allelic ratio lower than the normal range.

alleles. The difference in the ratios of the alleles of a COL4A2 SNP for pregnancies with and without trisomy 13 is sufficiently great that detection of trisomy 13 in the fetus is possible using placental RNA samples.

Determination of SNP Ratio of Collagen Type IV Alpha 2 mRNA in Placentas

The placental-expressed collagen type IV alpha 2 (COL4A2) mRNA was chosen. The COL4A2 gene is located on chromosome 13. A polymorphic SNP (Table 16) located within the coding region of COL4A2 gene was identified from a public database and was targeted for assay development.

TABLE 16

A polymorphic SNP within the coding region of COL4A2 gene (SEQ ID NO:71).

| SNP | Sequences |
|---|---|
| COL4A2 (rs7990383)[1] | 5'- GACGAAGCTATCAAAGGTCTTCCGGGACTGCCAGGACCCAAGGGCTTCGCAGGCATCAACG GGGAGCCGGGGAGGAAAGGGGACA[G/A]AGGAGACCCCGGCCAACACGGCCTCCCTGGGTTCCC AGGGCTCAAGGTGAGGAGCAATTTCATCATGAAGCTGGCAAGACACTCTGAGGCCTCCCCA-3' |

[1]dbSNP accession number

Sample collection and processing. First- and second-trimester placental tissue samples were obtained from three pregnant women carrying trisomy 13 fetuses. Placental samples from seven first-trimester pregnant women carrying karyotypically normal fetuses were also collected by chorionic villus sampling (CVS). The placental samples were stored in RNAlater™ (Ambion®, Austin, Tex.) immediately upon collection and kept at −80° C. until RNA extraction. Total RNA was extracted with Trizol (Qiagen, Hilden, Germany) following the manufacturer's protocol. The extracted RNA was treated with DNase (Invitrogen, Carlsbad, Calif., USA) to remove any contaminating DNA.

Reverse transcription and PCR amplification. 1.25 micrograms of the placental RNA were reverse transcribed in a reaction volume of 40 µl according to the manufacturer's instruction (ThermoScript, Invitrogen, Carlsbad, Calif., USA). The reverse transcription was performed using the reverse PCR primer with sequence shown in Table 17.

For the PCR amplification, 40µl of the placental cDNA was used in a total volume of 80 µl. Each reaction contained 0.6X HotStarTaq PCR buffer with 0.9 mM MgCl$_2$ (Qiagen), 25 µM each of dATP, dGTP and dCTP, 50 µM of dUTP (Applied Biosystems), 200 nM each of forward and reverse primers (Integrated DNA Technologies) and 0.02 U/µl of HotStar Taq Polymerase (Qiagen). The PCR primer sequences are shown in Table 17. The PCR reaction was initiated at 95° C. for 7 min, followed by denaturation at 95° C. for 40 sec, annealing at 56° C. for 1 min, extension at 72° C. for 1 min for 50 cycles, and a final incubation at 72° C. for 3 min.

TABLE 17

Primer sequences for reverse transcription and PCR amplification of the COL4A2 gene.

| Primer | Sequence (5' to 3') | SEQ ID NO: |
|---|---|---|
| Forward PCR primer | ACGTTGGATGAAGGGCTTCGCAGGCATCAA | 72 |
| Reverse PCR primer | ACGTTGGATGACCAATGTTGCCAGGCACTC | 73 |

SNP detection and allelic ratio quantification by primer extension reaction. The primer extension reaction was performed as was described in Example 3. The PCR product was first treated with shrimp alkaline phosphatase (Sequenom, San Diego, USA). Four microliters of base extension cocktail containing 771 nM of extension primer (Integrated DNA Technologies), 1.15U of Thermosequenase (Sequenom) and 64 µM each of ddATP, ddCTP, ddGTP and dTTP (Sequenom, San Diego, USA) were mixed with 5 µl of water and 5 µl of the PCR product. The thermal profile was 94° C. for 2 min, followed by 94° C. for 5 sec, 52° C. for 5 sec, and 72° C. for 5 sec for 100 cycles. Sequences of the primer extended products for each SNP allele are shown in Table 18. The molecular weights of the final extension products were detected by MALDI-TOF mass spectrometry as was described in Example 3. The peak frequency ratios for the two SNP alleles in fetuses heterozygous for the SNP were determined.

TABLE 18

Sequences and molecular weights of the extension primer and the expected extension products for the coding SNP of COL4A2 gene.

| | Sequence | SEQ ID NO: | Mass (Da) |
|---|---|---|---|
| Unextended primer | GTTGGCCGGGGTCTCCT | 74 | 5209.4 |
| Extension product for allele G | GTTGGCCGGGGTCTCCTC | 75 | 5482.6 |
| Extension product for allele A | GTTGGCCGGGGTCTCCTTTG | 76 | 6131.0 |

The extension primer anneals to the reverse strand of the sequence.
Letters in bold font indicate the dNTPs and ddNTPs residues added to the extension primer.

Figure 13:
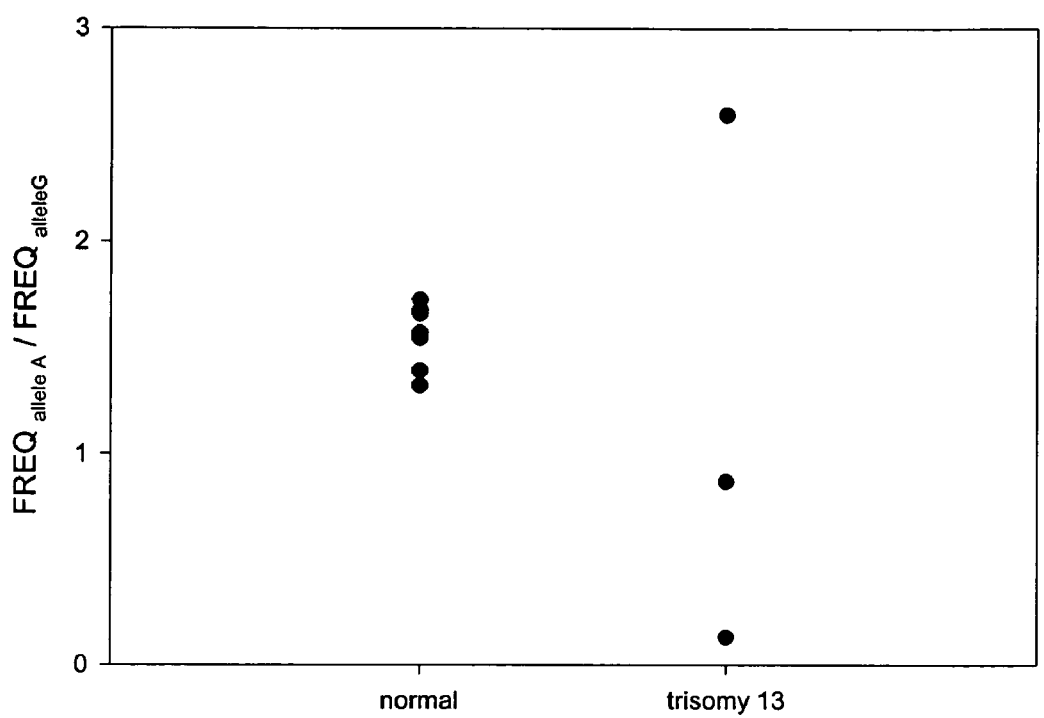
FIG. 13. COL4A2 transcript allelic ratios in placentas of pregnant women carrying normal and trisomy 13 fetuses. The allelic ratios were determined by primer extension followed by mass spectrometry analysis using SNP rs7990383.

Deviation of allelic ratios of COL4A2 transcripts in the trisomy 13 placentas from the normal placentas The allelic ratios of COL4A2 mRNA in the placentas of karyotypically normal and trisomy 13 pregnancies were compared. The ratio was calculated by dividing the relative amount of allele A (higher-mass allele) to the relative amount of allele G (lower-mass allele). As shown in FIG. 13, all trisomy 13 placentas showed allelic ratios that deviated from the normal samples without overlapping. The allelic ratios of the trisomy 13 samples segregated into two groups. The trisomy sample with an extra A allele showed allelic ratio higher than the normal range, while samples with an extra G allele showed allelic ratios lower than the normal range.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

Genomic sequence of PLAC4 gene locus (SEQ ID NO:77). This PLAC4 gene locus spans the nucleotide coordinates 41469028-41480585 on chromosome 21 based on the Human May 2004 (hg17) assembly at the UCSC Genome Browser (genome.ucsc.edu/).

TABLE 19

Genomic sequence of PLAC4 gene locus (SEQ ID NO:77).
This PLAC4 gene locus spans the nucleotide coordinates 41469028-41480585
on chromosome 21 based on the Human May 2004 (hg17) assembly at the UCSC
Genome Browser (genome.ucsc.edu/).

chr21: 41469028-41480585
Base position[1]

| | |
|---|---|
| 41469028 | TGGGATGTTTTCAGATTTTTATTATATGGCAATCATATACCTGCACCTAGAAATATACAA |
| 41469088 | CCTCGGCGCTGCCATTGCAGGAAGACAAAGAGACTGTCTAGAGAGTAACGTGGCGATGCC |
| 41469148 | CTGGGCAGCTCCATCATTCCAGGGTACCATAAAGGGAAGTGGGAATGCACACTCCATCTG |
| 41469208 | TTTCACGCTAGGCTGAAAGTGGCAGGGGGAGAATTTACACCTGGCCTGCAAAAGGCAGCC |
| 41469268 | TTGTGTTCCCACTTCAGAGCCCCAACTTCTCCAAAGCCAGTGCTTGGGAAATGGCCTTGT |
| 41469328 | TGGCAGCAGGCAGGAGACTGGTGCAGTGTGCCAGCTGTGCAAACCCCCACCAGACTGGTG |
| 41469388 | CAGTGTGCCAGCTGTGCAAACCCCCACCAGCAGCACCCCCACCAGCAGCCAAAGAAAACA |
| 41469448 | ATTTCTAAAGCAGCCCCCAGGATTTCATGCCACGGGGGTGGTGAGGGGTAGGAGGAGGTG |
| 41469508 | GAAAGCATTGAATCAGAAAGTCTTCCAGGTACCAGCAATGCCAGGGTTAATATGGTCTGG |
| 41469568 | CTTGCTTTTCAGGTGAGCACCTGTAGCTGGCAGGAAAGTGGCTTCTTGGTGGAGGTGGGC |
| 41469628 | ATGAATTCCAGAAGCCTTGGAGAGACATCCAGAGCCCTTCCCACTACATCGTGCTGCCTC |
| 41469688 | CTGGGGAAATTCCTAAGCTTTTTTTGAATCAGAAAAGCCACTGACAAGCAGACAGAATTG |
| 41469748 | TGTGGCTTGCGCAGTGATTGGAGAGCTAGGTGCTTTGGGTACTAGTCCCAGAGCTGCTAC |
| 41469808 | TTGTCGAATGTTGGGTATTGGAGAGAAGTCATTTGAGCTGTCTGAGCCTCTGTTTCCTCA |
| 41469868 | TCTGTAAATCAGGGAATTTGAACAAGTGACCTCAGATTCCTTCTAGAAGCTCTAACAGTC |
| 41469928 | AATGATATCATCTATTTCATTTGAGAGAATCTCCATAGCTCTAATTTTTTGCCCCCAGAC |
| 41469988 | CAATCTGCTTCAGCTTTGTGTGGGTGCAACACCTGGGGTCCTGTTAAAATGCAGAATCGG |
| 41470048 | ATTCAGTGACCGAGAGCAGAGCTGAGGGTGGCTGCTGCCAGCTCACAGGTCACACTTGGA |
| 41470108 | GTCGTTGCTTCTTTCCCCAAACCAGCTGCCGATGGTTCCTGGAAAGAGCAGGAATACCTT |
| 41470168 | GCAGAAGGGCCTAGAAATAGAGATTCCCATATGCAGTCCAGACTTATTGGGTGAGCCTGT |
| 41470228 | CTGCACTAGGACCTGAGAATCTGCATTTTATTATATCCCTTGAGTCCCCTTTAAGCAGCC |
| 41470288 | ACGCTGGCCCCAGCCATTGGACTCTATTTGGAGGCCACTGCAGAGGCCAGATGCCCCTCT |
| 41470348 | GCTCGGCGGTTTCCTGTGCAGAAAGGCTGTGTTCTTTCTTCTTCCTAAATACTCTTCCTA |
| 41470408 | GGTTAAGTGTTTCCTTCTCTTTGCCCATCTAGAAAATCTCCACCTCAAGCAGGTCGTGTT |
| 41470468 | CCAAAAACTCCTCGTGTTGGGCAAGTGGAAAACACGCAGTTTTTTCTAGGGGTCTCATTC |
| 41470528 | TGAGGCGGTGCTGCTGAAAATCTTGGTGCTGAACGTGTGTTTTTGAGATTTCCAGTCTAT |
| 41470588 | CACAGGGCCACAAGGTGTAAATATCAAGAAAAATGAATTACTAGAAAGGCAAAGTGAAAA |
| 41470648 | AGACATACAAAATACAAGTGTCATTCTTTTTATTCTTAGTTTGGACAGATAGTCCATTCT |

TABLE 19-continued

Genomic sequence of PLAC4 gene locus (SEQ ID NO:77).
This PLAC4 gene locus spans the nucleotide coordinates 41469028-41480585
on chromosome 21 based on the Human May 2004 (hg17) assembly at the UCSC
Genome Browser (genome.ucsc.edu/).

| | |
|---|---|
| 41470708 | TCTACACTGGTCCCACGGTTTCTGAAGCTTCCTGTAATGATCAGTGGTTACCTTGTTGCC |
| 41470768 | CAAGTAACTGCAAATCCCTCCTCTACAAAGTGTQCTTGCTCCAAGGCAGTGCAAACTAGA |
| 41470828 | AGTTGTTACAAATGGTTCCAGTAACAAATTTGTTTGGCGGCCTTTTCCCATGAATGAGAC |
| 41470888 | AGTGGTTATTTTTGCTAAAGCAGAAAGGAAATGTGATACTATTGGGCTGTGTTTTGCCCT |
| 41470948 | CTGGAGTAATCCTGCTTGGGGAAAATGGAGGCTTGTTCCAGAATGCAGAAATCCCTGTTA |
| 41471008 | AATTAGGCAGTCTTGGGCTGGAGGACGTGTGCCTGCCTCCCCAGTGCCTCACAACTCACA |
| 41471068 | TCTCTAAAGGCCACTCAGGTGGGACACCATCAAGACATTGAAAATCGACAGAAGGAAGGC |
| 41471128 | AGGAAGGGGAGAGGATCGAACCTGTCAAAATAGATATTCAGAAAATCTGTGCTCTAAAAT |
| 41471188 | AAGGCAGCCCTTCCCTCACAGCACACTTATTCCTAATTTCAACAGGACTCCTAGTCTTGC |
| 41471248 | CCCACAGCGTCACAGCCTACAGCAAATTAGAAACTGGGGTGGGGGCGGATATTATTCCA |
| 41471308 | CCAGTAATACCCTTGGGACGGGGCACACAAGATGTTTGCCCTCCTACCTCTCTGTCACCT |
| 41471368 | TCCCAAGAAAGGGTCAAGATGAAACAGTGTGCGTTTATGGTATTGCGAGAGTTAAGTGAG |
| 41471428 | CTGCGGTGTATTAGAACCTTAGCCTCGCGCAGCGTCAGCCGTGTGGTAAGTGTTCCATAA |
| 41471488 | ATCTTCGTTTAGAAAAAGTGGCAAATTCCAGGCTGCTAGTAAACAAAGGAGGGAAGACAG |
| 41471548 | ACAAAACGGAACAGCAACAACAGAAAACCCAAGAACTAGATGCCCAACAATCTGGGTCTG |
| 41471608 | TATCTTGAAGGAATGTGCATCCTGTCCTCTGACTGCAAACCCAGGCCTTCTGTGGCCCCA |
| 41471668 | CGATGCTGCCTCCTAGCCCTCCTAAGGTGGGAATGGAGCTTTACCCCTTGGTGGCAAACA |
| 41471728 | GACCTGGCTCCATGGATCTCAACCTGGGGTGATTGTGTCCCACCCCAGGGGACATCTGG |
| 41471788 | CATCCTCTGGGGACATTTTGAGTTCTCACAACTTAGAGGGTGCTACTGGCGTCCTGTGGG |
| 41471848 | TGGAGACTGGAAGTGCTGCTCGGCATTCTTTGCCGTACAGGGCAGCCCCCACAACAAAGA |
| 41471908 | ACGATCTGGTCCAAAATGGCAACCATGCCAAGATTGAGAAATCCTGGTTACTCGACACAG |
| 41471968 | CAGGTCGGCTGGCCTAGGAGTTGCTGCCCAGAGAGGCAAAGGGAGAATGTCCAGTGGAAA |
| 41472028 | CAGCTGCCCTGAGCATACAGGGCACGCTGACACCTGCTGATTCCCCATCCTTAAGGTCC |
| 41472088 | TGTATTGTTCCTAACACCACGTGGATCTTCTTGCCAGATGCATTAAAGTGTGAGAAGAGT |
| 41472148 | TAAAAATCACTTATAACTGGAGTGACTGGGGGTTAAAGAGGAGAAAAAATTTGAACCTGA |
| 41472208 | CTCAAAGGATGAGCATGTTTTTCTTTCTTTCTTCGGCACATTGGCTGGGTGTGGCGGCTC |
| 41472268 | CATGCCTATTATCCCAGCACTTTGGAAGGCCGAGGTGGGAGGATTGCTTGAGGTTAGGAG |
| 41472328 | TTCAAGATCAGCCTAGGCAACATAGCAAGTCCCTATCTATATAATTTTTTTTTAAATTA |
| 41472388 | GCCAAGCTTGGTGGTGCATGCCTGTAGTCCCAGCTACTCAGGAGGCTGAGGCAGGAGGAT |
| 41472448 | CACTTGAGCTCAGGAGTTCAAGGCTGCAATGAATTACGATTGTGCCACTGCACTCCAGCA |
| 41472508 | TGTGCAACAGAGCAAGACCTTGCCTCAAAACATATTAAGCACCTACTGCATGTCAGGGCC |
| 41472568 | TTGGTCTAAGCCCTGGTATGCAACAGTCAACTAGACAQAGAGAGTCTTGGCTTTTACAGA |
| 41472628 | ACCTCCCCTTATAAGGAAGACAGATTGTCAAGGAAGTAAACAGACTTTTAGAGGAGTGCT |
| 41472688 | GTGAGACAGTGCCATGTGGGAAGGGGTATTGGTGAAAGAATCCTGCTTTATAAGGGCGGT |
| 41472748 | TATGGAAGACCTCTCTGAGGAGGTGCAATTTGAGATGAGATTGGCTTGAGGAGGACTGAG |
| 41472808 | CCTTCAGAAGTTAGGGAAAGCGTGTCCCAGGCTGCAGCCAGGGAGGTGAAGACTTGAGGG |
| 41472868 | TGTCAGGGTGAGGAGTGAGGGTGTCAGGGTGACTGAGGGTGCCAGGGTGAGGAGTGAGGG |

TABLE 19-continued

Genomic sequence of PLAC4 gene locus (SEQ ID NO:77).
This PLAC4 gene locus spans the nucleotide coordinates 41469028-41480585 on chromosome 21 based on the Human May 2004 (hg17) assembly at the UCSC Genome Browser (genome.ucsc.edu/).

| | |
|---|---|
| 41472928 | TGTCAGGGTGAGGAGTGAGGGTGTCCAGGGTGAGGAGTGAGGGTGTCAGGGTGAGGAGTG |
| 41472988 | AGGGTGTCCAGGTTGAGTGAGGGTGTCCAGGATGAGGAGTGAGGGTGTCCAGGGTGAGGA |
| 41473048 | GTGAGGGAGTCCAGGGTGAGGAGTGAGGGAGTCCAGGGTGAGGATTGAGGGTGTCAGGGT |
| 41473108 | GAGTGAGAGTGTCCAGGGTGAGGAGTGAGGGTATCCAGGGTGAGTGAGGGTGTCCAGGGT |
| 41473168 | GAGGAGTGAGGGTATCCAGGGTGAGTGAGGGTGTCCAGGGTGAGTGAGGGTGTCAGGGTG |
| 41473228 | AGTGAACGTGTCCAGGGTGAGTGAGGGTGTCCAGGGTGCAGAGTGAGGTGTCCAGGGTGA |
| 41473288 | GGAGTGACGGTGTCTGGGGTGAGTGAGGGTGTCCAGGGTGAGGAGTGAGGGTGTCAGGGT |
| 41473348 | GAGTGAGGGTGTCCAGGGTGAGTGCACATGTGTGGTGAGGAGGTGTTTGCAGTGCTTCAG |
| 41473408 | GCGCAGCAACTCTTTCATCTAGTTTAAAATTGTGCTCTGAGGTTAGATTTTAGTAGAACA |
| 41473468 | AAGGCCTTACAAAGAATGTGAAAACATTGTGCTTCCCTGCTTACAGGCAATTAAAAAGGA |
| 41473528 | GAATCAAGCTGAGGGTGCCTGGTGTGGGGTGGGTGGAGAAGACCACAGAGACTATTGTG |
| 41473588 | TGTTTTATTCAACAGTGTCCTGGGCTGCTTTCTCCAGAAATGTCCCTGACACATGGATGT |
| 41473648 | AAGTGTGGCTAGTTTACTGGGAGATGATCCCAGTGATGCAGGACAGGCGAGCCCTAAGAT |
| 41473708 | TGAAGCATAGCCCGGGAGGGTTCTTAGCTTTGCCCAGGAAGGAACTCAAGGGCAAGCCAG |
| 41473768 | TGGTGTTAGCAACTTTTATTGAAGCGGCCGGCTGTGCACAGCAGCAGCAGAGGCGCTGCT |
| 41473828 | CCTTGCAAAGCAGGGCTGCCCTACAGGCTGTGCGCCCACAGTAGCAGCTCAGAGGCAGTT |
| 41473888 | CTGCAGTGGTATTTGTATCCACTTTTAATTATATGCAAATGAAGGGGCAGTTTATGCAGA |
| 41473948 | CATTTCCAGGGTGAGGGTGGTAACTTCTGGGTGCTGCCAGAGCCATGGTGAACTGACTTG |
| 41474008 | ACACAGGTCGGTGTGTCCTATGGAAACTAGCATCTGCCCTGGACCTATTTTAGCTAGTGC |
| 41474068 | TCAGTTTGGTCTGAGTGCCTGAGCCCCACTTCCAGAGTTGAGTCCCACCTCCTACCTCAT |
| 41474128 | TCCCCCTTCAGAGATTAGATACTCCTCCTTAATCTTAAGGGGGCTGCAGAAGGGCGGAGA |
| 41474188 | TCTGTTTTCCGTAACTACTTCCTGCTGAGTTTATGGACGTAGGCCCTGCCTGGCACTGGA |
| 41474248 | GGAGTAAAAATCTCTGGATACCTGATCTAAGGAGCCCAGAGGCAGGACGATTTCATTCTC |
| 41474308 | CGTGTCAGTGGACAGGATGGGCTGGAAGCCTTGTGCCAGCATTGTCTCTGGAACTGTGGT |
| 41474368 | AATCTAGAATACACAAACTTTACTAAGAGGTTAAAGAAGCAAGGACCAAACATTTGTAAC |
| 41474428 | AAGACAGTTGTCAAAGGTCCTAGAAGAGGTGAAAAACAGGTGAGACTTGGGAAGGCACTT |
| 41474488 | TTGATGGTTGACCAGATATAGTTGGGGGCAGTGCCCTGGTTATATCTATGTAACTAGGTA |
| 41474548 | GCTTGCTCATAGATCTTTTGAATGTTAACCTCAACCTGTCCAGAGTTAATATATGTGCAG |
| 41474608 | CAGGTTTTATTAATAACTGCACAAGACCCCACCTTGTTCAGCTAGTAAATAATCCAATGC |
| 41474668 | TAGTCTGTTATCAACAACTACATTTTCCAGAGTCTGGGGAACTCTTGAATTCTCTTTAAT |
| 41474728 | GCCTGATCTCCGTTGGTGGCTAAGGATTCTAGGATTTGAGCCAAGTTCTTTAGCGTTAAC |
| 41474788 | TCATGGTAGGCAAAGCCACCCCAGGGTGCTGCTAGTCCTATTGCCACCCTGATTCCTGCC |
| 41474848 | AGAATTAGTTTTATTGCTTACTTATTTCTGATATTCTTGGGTCCTAGGCGTTATAGATTG |
| 41474908 | TGACCCCTGGAGGGGTAAGAGTGGCCAACGTTCATTCATGTCAGTTCCAAGTTTTTTAGA |
| 41474968 | TACAAGGGAAAGCTATTCCTTAAAGAAGAGGTGACTCCTTAGGGAGTTGGAGTGGTTACA |
| 41475028 | GGGTGTGACTTCTTCCCATTCATAGTCACAAACAAAAATGAACCCAACTAGGGCACCAAG |
| 41475088 | AGAAGCCCTGCGGGGTGCGATGTTTATACTTCATTGCCAGGTTGGGTCTATAGAGATATT |

TABLE 19-continued

Genomic sequence of PLAC4 gene locus (SEQ ID NO:77).
This PLAC4 gene locus spans the nucleotide coordinates 41469028-41480585
on chromosome 21 based on the Human May 2004 (hg17) assembly at the UCSC
Genome Browser (genome.ucsc.edu/).

| | |
|---|---|
| 41475148 | TTCCACCTGTTCTCATGGTGGTGGTTGAACAATCTTTGTTTTCTAGAAGAAGGTAGTACT |
| 41475208 | GTCACCTTCCCAGATCAGGCAGTTGTTTTTCCTTTGTATGTTCCCATCCGGGAGAAGGTA |
| 41475268 | CCATATATGGTCTTTTCACTCACAAATGGAATCTCATTTACCTCCCCGTGGTCTTGGAAA |
| 41475328 | CTTGGCAACTAGAGTTGGACCAGAGCATCGCAGGGAAGCTTCCACTTTTGTGTCATTAAT |
| 41475388 | GCAAGAGTGGATGCAAATGTTAGAGTTATGAGTGCACTGGAGATATAGATGCCCAACTTC |
| 41475448 | CCAGATTCCGATAATAGTGGTCAGGGCAGGGGACAGCAGGGTCCAGGGGGATCCACTA |
| 41475508 | AGTGGGGAAGAGTTCCACTTCACAATAGGGGTTTGGGTATTTTGGGGTGCTATGGTTAGT |
| 41475568 | TAGGAGGTCTGGGGACATGGTCCTGAGATTTTCCAGATAGGTCGGAAGATGAAACTGTCT |
| 41475628 | ATCCTGGGGGTGTTGATGACAAATCTGGCAGCCATAAAGATGATTCTATGATGCTATAAT |
| 41475688 | TTTTGAAATATTTACTGTAGAATTTTGTCCACCCTCCCTGTCCACATACACACTAGCTTA |
| 41475748 | GGTTAATTAGAAGAGCAAACAGAATTAACAGTGGCATCATGGTATCTGGTTGGGTCTTAG |
| 41475808 | AGTAGCTTCTATACCCAACAAGCCCACAGGAGATGTTTCCCAGGAGGAGGTGGCTGGTTA |
| 41475868 | AAGCCATAGAAAGGAAGTACTACAGTCAGGAAGAAGAGCAAGATCAATGCTCCTATTCCC |
| 41475928 | ATCTACAGCATTACATTACCTCTTCTGGCTGAGTGTTGATTATTTTAAATAGGTAGCAGA |
| 41475988 | GGTCTTCCAAAGCTTTACTGATATTGGTTGTGGTTGTAGTGCCCTTCCTTTGTGCCTGTG |
| 41476048 | ACTCATAAGAAACAGGTTTAGTCCTGGATCTGTGTGCCCAAGTAGGTGTTCCCTGAAGTT |
| 41476108 | TAACAGCAGTGGGGGTACTTAACAATACCTGATAAGGCCCCTTCCATTTCATTGTAATTG |
| 41476168 | ATTCTTGGGGTATCCCTGTCTTTACCCTGTCTTTAAGGTTTTAGCAAGACTAAGTCTCCT |
| 41476228 | GGTTGAACCGGGGAGCTATTTTTTCCTTTGTGGGGAAGGACAGTATTTTATTTTTATATT |
| 41476288 | GGAGGGCCTTTTGAACCTGTCCTAAATTCTAAAGGGGAGGGGGAAGGTTCATATAGGTA |
| 41476348 | ATTACTACAAGCCAAGACCACAGCAGCTCAACACATAAAATCCATAGACAAATCAGTTTT |
| 41476408 | ACAACCCCATTTCCTGGCTTCTAGTTCTTGGCTTCCATACTGCTCAAAAGGAGTTCAAGG |
| 41476468 | GCCAATGAGTGCCCGCCCACCTCCACACTCATGCACTGTGCAGATGACTTACACAGACCA |
| 41476528 | TCTACAACATAGCTGAATTTCCTGACATGTTCTATACTACCTCTTTCTTAAAGTTATTTT |
| 41476588 | ACTCTAGGATAGGGAATTTACTATACAGGATTCCTCCACATATAAAATTACTCTTTCTTT |
| 41476648 | ATATCCTTCCTTGCAAAACAAACAAAAAATACATTTCTATTCATAATATTCTTTACATC |
| 41476708 | TCTCTTTTCTACTCACTGGTTCACTCATGTTTTGAACCTCCCATTTAGTAACTTCCGGAT |
| 41476768 | TAGACAAAAAATTTTTTCTCAATAAAGAATACATTTCTTTAGCACATTTTATGGAAACCT |
| 41476828 | AGGAAGGAAGAAGTCATGAACTTCACACTAGACATTGTCATTCTATAACTGAGAACCATT |
| 41476888 | CTACCATTTTATGATTTTAAACCACACATTAAGCATATCCCATTTACGTGTATTTAATTA |
| 41476948 | TTTCACTTTTAACTTTATCTAGATCACCGAGAACCAAGGTACCATGCAAAGCTGGTCACC |
| 41477008 | ATTTAAAGCCATTTTAACCATTTTAAAGCCTATGAACATCAGTGACTTACCTAGGTAAAA |
| 41477068 | ATCCTAAAGTTAAATTTTAGAAGATACAAGATTCTCTTCAAACTAATAAGCTTTCAGTAG |
| 41477128 | TCTTATTTGTTGAATGTATGAGTGTTCTTTTATCTATAAGCCAGTTTGACAGCACGCTAG |
| 41477188 | ATGTAACACACATCACAATACATGTACATATACCCAAAAACATATTAAATAAAATGACCT |
| 41477248 | ATACAAGACAACTGGATTCAAGTTATTTACAGAACTGGGACCCATCTACCTGGCCAAATT |
| 41477308 | TTGTTTGCCCCGATAGGTATGGAAAACAGGAAAAGGCAGGACAGGGAATCCCATAGCATC |

TABLE 19-continued

Genomic sequence of PLAC4 gene locus (SEQ ID NO:77).
This PLAC4 gene locus spans the nucleotide coordinates 41469028-41480585
on chromosome 21 based on the Human May 2004 (hg17) assembly at the UCSC
Genome Browser (genome.ucsc.edu/).

| | |
|---|---|
| 41477368 | AACTAAAAAGGGGAGGAAGCAAACTGCATTGCTCAAAAGGAGATTCTGGAGTCCCCACGC |
| 41477428 | CACTGGAGAGCACACTCAGTGGTGGAAATACCAAAGAAAAATGTTCAGGCGGCTGCTTAT |
| 41477488 | CTGCCACTGTGGAAAGCTGTCCTCTGGGACAGTAAACTTACTTGAGCTAAGCAGCTCACT |
| 41477548 | GGGGCTAGTAGGAGAAGGTTAGCTCTAGTATTGATGGAAGCTTTTTGTTGTTATTGTTCT |
| 41477608 | CTCTCACCAGAGCAGTTAGGACATTTGCATTGCCAGGGGCCCTTTTGCGTATAGTAGGCG |
| 41477668 | CAGTGATTCTGGCCCAGGGGTCAGCAAGTCAGGCATCAAGTCTTGTCTAGGCATCCCAGA |
| 41477728 | TGCTAATTTTGTAACATTTTCTCAAGATGAGTAATCCTGAGGGGCAAG<u>GAGGCTTAAAGT</u> |
| 41477788 | <u>CACTGTTAACAATTGTACTTTTTGGCTATTTCTTTTTACTCCCCTCTTTTGCCCTGTCCC</u> |
| 41477848 | <u>TGTTGTTGTAAACTTTAAAGGCTATGTTTAAGCGTCGTTTCATAGGACTTGAAGGTCCCA</u> |
| 41477908 | <u>TTGCTGCTTTTTGTAGATTCCTCCTAATGTCAGGAGAAGATTGAATGAGAAAATGTATAC</u> |
| 41477968 | <u>CCAGGAGAGCTTGCCCTTCTGGGGTGTCTGGGCCTGCATTAGTATATTTCCTGAGTGCTT</u> |
| 41478028 | <u>CAACTAAAAGACCCTGAAACAGAGCGGGATTTTCATCTTTTCCCCGAGTTACTTCTTTAA</u> |
| 41478088 | <u>CCTTGTCATAATTGACTGGCTTAACCACACACTTTTTCCTCTACTTTTTTTTCCCCACAG</u> |
| 41478148 | <u>CACAGCAAGCGGATGACAATATTTGTAAATCGTGGCAATTTGAAGAACATAGTCAACGTA</u> |
| 41478208 | <u>ACAAACTCTTGTATAAGCTTTTCTGGTTTATCTGAAAACTGGCCAATTCTTTCCTTTTAT</u> |
| 41478268 | <u>AAGGTCTAATTAGACATGGAAAGTGGCATATGTACTCTTTGAGTGTTCCCTCATTTCCAT</u> |
| 41478328 | <u>CAACTACTTTCCACAGTGGACACAGGCTTGACCTTAGGGGCTGATATGGAGCCCCACTCC</u> |
| 41478388 | <u>TGGTGTACTGGTTGGGCTCATTTTCTTGGGCAGCAGAGGGTATAGGCTAGGGCTAGTTGG</u> |
| 41478448 | <u>ATAAGGGGAAAGGTGCCTGATGATATTGGGGTGGAATCTCATTAGGGAATTGGCGAGAA</u> |
| 41478508 | <u>CCCCCACTCAGGACTGGGGACTGAAGAGACTCTGGGGAGGCTTATGAACTTTCTATGGG</u> |
| 41478568 | <u>GAGCAGCTAGGTGGGGATCCCTTATGCATGGCATTCTAATGCCTGGAAGTAACGTGATCC</u> |
| 41478628 | <u>AGTATAGAGCCATAAAAGCCTGTACATAAGGGATCTCTTCCCATTTTCCTTCTCTTTTAC</u> |
| 41478688 | <u>AAAATAAGCCTAATCGTAAAATATCACTATAGTATATAGAACCATGTTTAGGCCAGATAT</u> |
| 41478748 | <u>ATTCGTCATCTAACTTGTATTTAACCCAAATGGTGTTGCAATACAAAATGAGTTTCTTTT</u> |
| 41478808 | <u>TCTTTAAGCCAAATTTGAATTTGCTCCAATAGCTTAAAAGACACCCTAGCGGCGAGTCCC</u> |
| 41478868 | <u>TTGGGATACTCCTTGTTGTCCCCATGCCTATATTAAGGATCTCTCTACAGAGGGTTTTAT</u> |
| 41478928 | <u>TAGCCCAAGTTTAGCAAAAGCCTAGTTACTCTTCCCTCTTAAATTCCCGTGTTCTTTAAA</u> |
| 41478988 | <u>GGTGTAAATATAGATAGCAAGGTGTTATAAAAATGGATTATGAGCTACG</u>AATGGGCAGTC |
| 41479048 | GAATGTGGAGCCTAAATTCCATAGAGATCTAGAGTTGGGTGGAGAGGGGGCTAAACAAAT |
| 41479108 | GGAGGAAGGGAAAGGGGTAAACAGCGTTGCCCAAGGGGAGACCTCAGAGGCTCTGACTTG |
| 41479168 | CTGAAGAACCTACCCAGTAGTGGAGATACTGAAAAAAATATTGGGCTGGCCACTTGTCTA |
| 41479228 | CCACTGTAGGTGGCTGACTGCCAGGCCAGGAGCCTGGGAGCTCCCAATTCCTTTGACCAA |
| 41479288 | GAGCAGCTTAGGCAAGGGAGTTATAAGACAGTACACAGGAAGGAGCTTGCAATTGGCTAT |
| 41479348 | TAGGAAAATAATACTCCTAACTTCAGGGTGGAAAAAGACAAGACCAATATTCGCCTAGCG |
| 41479408 | AAAGGGGTATAACCCACAATCCTAGAGGAAATGTCAGTGCTAAAAACCCCAGAGCATCTG |
| 41479468 | GAGGGTGGCCTATAATACCGATGCTGAGAACCCAAAATGCCTGCGTTTCAGCCAACAAGG |
| 41479528 | ATGCCCTCGCCAAAGCAGCTGTGCACAGCAGTGCCAAAAACCCTGGGGTACCCAGTGGGC |

TABLE 19-continued

Genomic sequence of PLAC4 gene locus (SEQ ID NO:77).
This PLAC4 gene locus spans the nucleotide coordinates 41469028-41480585
on chromosome 21 based on the Human May 2004 (hg17) assembly at the UCSC
Genome Browser (genome.ucsc.edu/).

| | |
|---|---|
| 41479588 | GGCCAACCCCGTGAACCCAAGACCAGGTTACAGAACATAGAACAACGTGACAACGTGACT |
| 41479648 | CTGGTATCCCAGAGTCAACACAACAGGGGACCTCTCACAACCAAGTGTCCTGCCTTAAAC |
| 41479708 | AATTGCCCAAATACAATTAACAGAAAGTCGAAAGCAAACATAAGACTCCAAACAAGACAT |
| 41479768 | ACATGTTAGGACTGAAAATGAAACCAAAGTGGAGCAATAAAATGGAGTCAGAGGAGAAAG |
| 41479828 | AACCAGGTGAAGGGGTGGCAAGAATGTGCTTCAAGGCACCTAAACCGTGGGGAACTGACC |
| 41479888 | GCTTAGCCAAAGGCTTTTATTTCCTAGCTTACCTGATATTACTGGGGAGGGTGCAAAGG |
| 41479948 | GGACTCTCACCCATCCACAGAAGACAAAATGGCACCAGCCAGTCTTCCACGTGGGACCCG |
| 41480008 | GGTGCAGGTCTCTCTAGGTTCCCCAGCTTGGGGGTGCTCAGCTTCTGTGTCGGGGCTGG |
| 41480068 | CTCGTTAGAGCAGTGGGTCCCACACGAGGCAGCTGTACTATGGACACTTGGCTGTCCACT |
| 41480128 | CAGTTTCACCACCTGCCAGGGAAAGATGATGGCTGTGAAAAGAGGCACTGGTTAGGGTTA |
| 41480188 | GAGCTCGGTAGTGTTAGCAGCTCTTTATTGGTACTTCCTCAGTGTTACAGATCTTACATC |
| 41480248 | CTCAATCACAGACTGCTTCACCGTCTCTTGCTGTCTTGCCAACTGCTGTCTCTTGTCTCT |
| 41480308 | CACCAATTGCTGCCTCTCTGTCTCTGCTGTCTTGCCTCTCTGCCAATTGCCACCATCTCC |
| 41480368 | GCTGTCCTTGTCCCTTTGCTGGTTGCCAGATGATGCAGGACAGGCAAGCCCCAAGACTGG |
| 41480428 | GGCTTAGCCTGGGAGAGTTCTTGGATTTGCCCAAAGATTCAAGGGTGAGCTGGTGGTGTT |
| 41480488 | AGGCAGCAGCTTTCATGGAAGCAGCTGTGCACAGCAGCGCCAGAGATGCCGCTCCTTGCA |
| 41480548 | GATCAGGGCTGCTCCATAGGCTGTGTGCCCTGAGTAGC |

Bold fonts: sequence known or predicted to be the transcribed regions of the PLAC4 gene.
Underlined fonts: reference sequence corresponding to the PLAC4 mRNA from NCBI database (NM_182832)
[1]Nucleotide coordinates on chromosome 21 based on the Human May 2004 (hg17) assembly at the UCSC Genome Browser (genome.ucsc.edu/).

---

What is claimed is:

1. A method for detecting the presence of a chromosomal disorder in the fetus of a pregnant woman, comprising the steps of:
   (a) obtaining an RNA-containing biological sample from the pregnant woman, wherein the RNA-containing biological sample contains fetal RNA, and wherein the biological sample is selected from the group consisting of maternal blood, maternal plasma or serum, placental tissue, and a sample obtained via chorionic villus sampling (CVS);
   (b) discriminating alleles from RNA transcribed from at least one genetic locus from at least one chromosome of concern;
   (c) determining the ratio of the alleles of the RNA transcripts; and
   (d) comparing the ratio from step (c) to a standard control representing a ratio of alleles from comparable biological samples obtained from pregnant women each carrying a chromosomally normal fetus, wherein an increase or decrease in the ratio from the standard control indicates an increased risk of having a fetus with a chromosomal disorder.

2. The method of claim 1, in which the chromosomal disorder is a member selected from the group consisting of trisomy 21, trisomy 18 and trisomy 13.

3. The method of claim 2, in which the chromosomal disorder is trisomy 21.

4. The method of claim 1, in which the chromosomal disorder is on the X chromosome or the Y chromosome.

5. The method of claim 1, in which the biological sample in step (a) is maternal blood.

6. The method of claim 1, in which the biological sample in step (a) contains cellular elements or cellular remnants in maternal blood.

7. The method of claim 1, in which the fetal RNA in step (a) is derived from the placenta.

8. The method of claim 1, in which step (b) is performed using reverse transcriptase polymerase chain reaction (RT-PCR).

9. The method of claim 1, in which step (b) and/or step (c) is performed using a member selected from the group consisting of a primer extension reaction, mass spectrometry, hybridization using at least one probe, hybridization using at least one fluorescently labeled probe, direct sequencing, cloning and sequencing, and electrophoresis.

10. The method of claim 1, in which the alleles in steps (b), (c) and (d) are differentiated by sequence variation.

11. The method of claim 10, in which the sequence variation is a single nucleotide polymorphism (SNP).

12. The method of claim 10, in which the sequence variation is an insertion/deletion polymorphism.

13. The method of claim 10, in which the sequence variation is a simple tandem repeat polymorphism.

14. The method of claim 1, in which the RNA is transcribed from a member selected from the group consisting of chromosome 21, chromosome 18, chromosome 13, chromosome X, and chromosome Y.

15. The method of claim 14, in which the RNA is transcribed from chromosome 21.

16. The method of claim 1, in which the RNA is mRNA.

17. The method of claim 1, wherein the RNA is transcribed from at least one genetic locus selected from the group consisting of collagen VI alpha 1 (COL6A1), superoxide dismutase1 (SOD1), collagen VI alpha 2 (COL6A2), mitochondrial ATP synthase O subunit (ATP5O), BTG family, member 3 (BTG 3), a disintegrin-like and metalloprotease (reprolysin type) with thrombospondin type1 motif, 1 (ADAMTS1), beta-site APP-cleaving enzyme 2(BACE2), intersectin 1 (ITSN1), amyloid beta (A4) precursor protein (APP), ATP synthase, H+transporting, mitochondrial F0 complex, subunit F6 (ATP5J), Down syndrome critical region gene 5(DSCR5), placenta-specific 4 (PLAC4), ribosomal protein L17 (RPL17), serpin peptidase inhibitor clade B (ovalbumin) member 2 (SERPINB2) and collagen type IV alpha 2 (COL4A2).

18. The method of claim 17, wherein the RNA contains at least one single nucleotide polymorphism (SNP) of the genetic locus.

19. The method of claim 18, wherein the RNA is transcribed from at least one genetic locus selected from the group consisting of collagen VI alpha1 (COL6A1) and collagen VI alpha 2 (COL6A2).

20. The method of claim 19, wherein the SNP in the RNA transcribed from the genetic locus of the COL6A1 is $^{Arg}850_{His}$ or $^{Ser}932_{Ser}$.

21. The method of claim 19, wherein the SNP in the RNA transcribed from the genetic locus of the COL6A2 is $^{Val}728_{Val}$.

22. The method of claim 17, wherein the RNA is transcribed from the genetic locus for placenta-specific 4 (PLAC4).

23. The method of claim 22, wherein the RNA is any variant transcribed from the PLAC4 gene, such as AF269287, AK027868, AK092431, BC093685, BC101615, BC101617, L13197, NM_182832 and LOC191585.

24. The method of claim 22, wherein the RNA transcribed from the genetic locus of the PLAC4 gene contains a single nucleotide polymorphism or an insertion-deletion polymorphism selected from the group consisting of rs3804026, rs4818219, rs7844, rs9015, rs13643, rs9305729, rs9305730, rs5019195, rs5019194, rs5844069, rs1049904, rs16998089, rs12482116, rs11909439, rs7278659, rs12106409, rs12106395, rs12106401, rs12106434, rs2183584, rs3949725, rs8130833, rs10222145, rs9981478, rs8130833, rs9977003, PLAC4-41471145 and PLAC4-41476236.

25. The method of claim 1, wherein the woman is during the first trimester of gestation.

26. The method of claim 1, wherein the woman is during the second trimester of gestation.

27. The method of claim 1, wherein the comparison in step (d) shows an increased risk of the fetus having a chromosomal disorder if the ratio in step (c) is higher or lower by 1 standard deviation from the standard control.

28. The method of claim 1, wherein the comparison in step (d) shows an increased risk of the fetus having a chromosomal disorder if the ratio in step (c) is higher or lower by 2 standard deviations from the standard control.

29. The method of claim 1, wherein the comparison in step (d) shows an increased risk of the fetus having a chromosomal disorder if the ratio in step (c) is higher or lower by 3 standard deviations from the standard control.

30. The method of claim 1, wherein the RNA is transcribed from at least one genetic locus selected from the group consisting of collagen VI alpha 1 (COL6A1), collagen VI alpha 2 (COL6A2), placenta-specific 4 (PLAC4), serpin peptidase inhibitor clade B (ovalbumin) member 2 (SERPINB2) and collagen type IV alpha 2 (COL4A2).

\* \* \* \* \*

UNITED STATES PATENT AND TRADEMARK OFFICE
CERTIFICATE OF CORRECTION

PATENT NO. : 7,645,576 B2
APPLICATION NO. : 11/384128
DATED : January 12, 2010
INVENTOR(S) : Lo et al.

It is certified that error appears in the above-identified patent and that said Letters Patent is hereby corrected as shown below:

In claim 17, column 93, lines 29-30, insert a space between the word "dismutase" and the number "1;"

In claim 17, column 93, line 33, insert a space between the word "type" and the number "1;"

In claim 17, column 93, line 34, insert a space between the number "2" and "(BACE2);"

In claim 17, column 93, line 38, insert a space between the number "5" and "(DSCR5);" and In claim 19, column 93, line 47, insert a space between the word "alpha" and the number "1."

Signed and Sealed this

Sixth Day of April, 2010

David J. Kappos
*Director of the United States Patent and Trademark Office*

SEQUENCE LISTING

<160> NUMBER OF SEQ ID NOS: 77

<210> SEQ ID NO 1
<211> LENGTH: 19
<212> TYPE: DNA
<213> ORGANISM: Artificial Sequence
<220> FEATURE:
<223> OTHER INFORMATION: PCR forward primer for direct sequencing of
      collagen VI alpha 1 (COL6A1) chromosome 21 gene

<400> SEQUENCE: 1
ggctgacatc accatcctg                                             19

<210> SEQ ID NO 2
<211> LENGTH: 20
<212> TYPE: DNA
<213> ORGANISM: Artificial Sequence
<220> FEATURE:
<223> OTHER INFORMATION: PCR forward primer for direct sequencing of
      collagen VI alpha 1 (COL6A1) chromosome 21 gene

<400> SEQUENCE: 2
ttggaaagcc aggacacaac                                            20

<210> SEQ ID NO 3
<211> LENGTH: 20
<212> TYPE: DNA
<213> ORGANISM: Artificial Sequence
<220> FEATURE:
<223> OTHER INFORMATION: PCR reverse primer for direct sequencing of collagen VI alpha 1 (COL6A1) chromosome 21 gene

<400> SEQUENCE: 3
agagcagcag cctcttcttg                                              20

<210> SEQ ID NO 4
<211> LENGTH: 20
<212> TYPE: DNA
<213> ORGANISM: Artificial Sequence
<220> FEATURE:
<223> OTHER INFORMATION: PCR reverse primer for direct sequencing of collagen VI alpha 1 (COL6A1) chromosome 21 gene

<400> SEQUENCE: 4
tgaggattgg tgggaaaaac                                              20

<210> SEQ ID NO 5
<211> LENGTH: 20
<212> TYPE: DNA
<213> ORGANISM: Artificial Sequence
<220> FEATURE:
<223> OTHER INFORMATION: PCR forward primer for direct sequencing of superoxide dismutase 1 (SOD1) chromosome 21 gene

<400> SEQUENCE: 5
ttttccactc ccaagtctgg                                              20

<210> SEQ ID NO 6
<211> LENGTH: 20
<212> TYPE: DNA
<213> ORGANISM: Artificial Sequence
<220> FEATURE:
<223> OTHER INFORMATION: PCR forward primer for direct sequencing of superoxide dismutase 1 (SOD1)  chromosome 21 gene

<400> SEQUENCE: 6
ttgcaacacc aagaaaaagc                                              20

<210> SEQ ID NO 7
<211> LENGTH: 20
<212> TYPE: DNA
<213> ORGANISM: Artificial Sequence
<220> FEATURE:
<223> OTHER INFORMATION: PCR reverse primer for direct sequencing of superoxide dismutase 1 (SOD1)  chromosome 21 gene

<400> SEQUENCE: 7
cgacagagca agaccctttc                                              20

<210> SEQ ID NO 8
<211> LENGTH: 22
<212> TYPE: DNA
<213> ORGANISM: Artificial Sequence
<220> FEATURE:
<223> OTHER INFORMATION: PCR reverse primer for direct sequencing of superoxide dismutase 1 (SOD1)  chromosome 21 gene

<400> SEQUENCE: 8
tctggcaaaa tacaggtcat tg                                           22

<210> SEQ ID NO 9
<211> LENGTH: 20
<212> TYPE: DNA
<213> ORGANISM: Artificial Sequence
<220> FEATURE:
<223> OTHER INFORMATION: PCR forward primer for direct sequencing of
      collagen VI alpha 2 (COL6A2) chromosome 21 gene

<400> SEQUENCE: 9
tcatcaacgt ggtcaacagg                                               20

<210> SEQ ID NO 10
<211> LENGTH: 20
<212> TYPE: DNA
<213> ORGANISM: Artificial Sequence
<220> FEATURE:
<223> OTHER INFORMATION: PCR forward primer for direct sequencing of
      collagen VI alpha 2 (COL6A2) chromosome 21 gene

<400> SEQUENCE: 10
gtggacatcg tcttcctgct                                               20

<210> SEQ ID NO 11
<211> LENGTH: 20
<212> TYPE: DNA
<213> ORGANISM: Artificial Sequence
<220> FEATURE:
<223> OTHER INFORMATION: PCR forward primer for direct sequencing of
      collagen VI alpha 2 (COL6A2) chromosome 21 gene

<400> SEQUENCE: 11
aacgacagtc tgcacgagtc                                               20

<210> SEQ ID NO 12
<211> LENGTH: 20
<212> TYPE: DNA
<213> ORGANISM: Artificial Sequence
<220> FEATURE:
<223> OTHER INFORMATION: PCR reverse primer for direct sequencing of
      collagen VI alpha 2 (COL6A2) chromosome 21 gene

<400> SEQUENCE: 12
tcactctcgt gcttctcgtg                                               20

<210> SEQ ID NO 13
<211> LENGTH: 20
<212> TYPE: DNA
<213> ORGANISM: Artificial Sequence
<220> FEATURE:
<223> OTHER INFORMATION: PCR reverse primer for direct sequencing of
      collagen VI alpha 2 (COL6A2) chromosome 21 gene

<400> SEQUENCE: 13
gtggatggca gtgaggttgt                                               20

<210> SEQ ID NO 14
<211> LENGTH: 20
<212> TYPE: DNA
<213> ORGANISM: Artificial Sequence
<220> FEATURE:
<223> OTHER INFORMATION: PCR reverse primer for direct sequencing of
      collagen VI alpha 2 (COL6A2) chromosome 21 gene

<400> SEQUENCE: 14
caggtaggtc aggagccttg                                               20

```
<210> SEQ ID NO 15
<211> LENGTH: 20
<212> TYPE: DNA
<213> ORGANISM: Artificial Sequence
<220> FEATURE:
<223> OTHER INFORMATION: PCR forward primer for direct sequencing of
      mitochondrial ATP synthase O subunit (ATP5O)
      chromosome 21 gene

<400> SEQUENCE: 15
ggcctgagat tcttcactgc                                                   20

<210> SEQ ID NO 16
<211> LENGTH: 20
<212> TYPE: DNA
<213> ORGANISM: Artificial Sequence
<220> FEATURE:
<223> OTHER INFORMATION: PCR reverse primer for direct sequencing of
      mitochondrial ATP synthase O subunit (ATP5O)
      chromosome 21 gene

<400> SEQUENCE: 16
aaaattagcg ggacatggtg                                                   20

<210> SEQ ID NO 17
<211> LENGTH: 23
<212> TYPE: DNA
<213> ORGANISM: Artificial Sequence
<220> FEATURE:
<223> OTHER INFORMATION: QRT-PCR F primer for detection of collagen VI
      alpha 1 (COL6A1) placenta-expressed transcript
      encoded on chromosome 21

<400> SEQUENCE: 17
gacaaagtca agtccttcac caa                                               23

<210> SEQ ID NO 18
<211> LENGTH: 18
<212> TYPE: DNA
<213> ORGANISM: Artificial Sequence
<220> FEATURE:
<223> OTHER INFORMATION: QRT-PCR R primer for detection of collagen VI
      alpha 1 (COL6A1) placenta-expressed transcript
      encoded on chromosome 21

<400> SEQUENCE: 18
gcgttccaca ccaggttt                                                     18

<210> SEQ ID NO 19
<211> LENGTH: 16
<212> TYPE: DNA
<213> ORGANISM: Artificial Sequence
<220> FEATURE:
<223> OTHER INFORMATION: QRT-PCR fluorescent probe for detection of
      collagen VI alpha 1 (COL6A1) placenta-expressed
      transcript encoded on chromosome 21
<220> FEATURE:
<221> NAME/KEY: modified_base
<222> LOCATION: (1)...(1)
<223> OTHER INFORMATION: n = c modified by 6-carboxyfluorescein (FAM)
<220> FEATURE:
<221> NAME/KEY: modified_base
<222> LOCATION: (16)...(16)
<223> OTHER INFORMATION: n = c modified by minor groove binding
      non-fluorescent quencher (MGBNFQ)

<400> SEQUENCE: 19
ngcttcatcg acaacn                                                       16
```

<210> SEQ ID NO 20
<211> LENGTH: 90
<212> TYPE: DNA
<213> ORGANISM: Artificial Sequence
<220> FEATURE:
<223> OTHER INFORMATION: QRT-PCR calibration standard curve single
stranded synthetic DNA oligonucleotide for detection of
collagen VI alpha 1 (COL6A1) placenta-expressed
transcript encoded on chromosome 21

<400> SEQUENCE: 20
tggacaaagt caagtccttc accaagcgct tcatcgacaa cctgagggac aggtactacc    60
gctgtgaccg aaacctggtg tggaacgcag                                     90

<210> SEQ ID NO 21
<211> LENGTH: 19
<212> TYPE: DNA
<213> ORGANISM: Artificial Sequence
<220> FEATURE:
<223> OTHER INFORMATION: QRT-PCR F primer for detection of superoxide
dismutase (SOD1) placenta-expressed transcript
encoded on chromosome 21

<400> SEQUENCE: 21
cagggcatca tcaatttcg                                                 19

<210> SEQ ID NO 22
<211> LENGTH: 18
<212> TYPE: DNA
<213> ORGANISM: Artificial Sequence
<220> FEATURE:
<223> OTHER INFORMATION: QRT-PCR R primer for detection of superoxide
dismutase (SOD1) placenta-expressed transcript
encoded on chromosome 21

<400> SEQUENCE: 22
tgcttcccca caccttca                                                  18

<210> SEQ ID NO 23
<211> LENGTH: 21
<212> TYPE: DNA
<213> ORGANISM: Artificial Sequence
<220> FEATURE:
<223> OTHER INFORMATION: QRT-PCR fluorescent probe for detection of
superoxide dismutase (SOD1) placenta-expressed
transcript encoded on chromosome 21
<220> FEATURE:
<221> NAME/KEY: modified_base
<222> LOCATION: (1)...(1)
<223> OTHER INFORMATION: n = c modified by 6-carboxyfluorescein (FAM)
<220> FEATURE:
<221> NAME/KEY: modified_base
<222> LOCATION: (21)...(21)
<223> OTHER INFORMATION: n = a modified by minor groove binding
non-fluorescent quencher (GBNFQ)

<400> SEQUENCE: 23
nagaaggaaa gtaatggacc n                                              21

<210> SEQ ID NO 24
<211> LENGTH: 65
<212> TYPE: DNA
<213> ORGANISM: Artificial Sequence
<220> FEATURE:
<223> OTHER INFORMATION: QRT-PCR calibration standard curve single
stranded synthetic DNA oligonucleotide for detection of
superoxide dismutase (SOD1) placenta-expressed
transcript encoded on chromosome 21

<400> SEQUENCE: 24
tgcagggcat catcaatttc gagcagaagg aaagtaatgg accagtgaag gtgtgggaa    60 gcatt                                                               65

<210> SEQ ID NO 25
<211> LENGTH: 21
<212> TYPE: DNA
<213> ORGANISM: Artificial Sequence
<220> FEATURE:
<223> OTHER INFORMATION: QRT-PCR F primer for detection of collagen VI
      alpha 2 (COL6A2) placenta-expressed transcript
      encoded on chromosome 21

<400> SEQUENCE: 25
gatcaaccag gacaccatca a                                             21

<210> SEQ ID NO 26
<211> LENGTH: 19
<212> TYPE: DNA
<213> ORGANISM: Artificial Sequence
<220> FEATURE:
<223> OTHER INFORMATION: QRT-PCR R primer for detection of collagen VI
      alpha 2 (COL6A2) placenta-expressed transcript
      encoded on chromosome 21

<400> SEQUENCE: 26
ccgtaggctt cgtgtttca                                                19

<210> SEQ ID NO 27
<211> LENGTH: 15
<212> TYPE: DNA
<213> ORGANISM: Artificial Sequence
<220> FEATURE:
<223> OTHER INFORMATION: QRT-PCR fluorescent probe for detection of
      collagen VI alpha 2 (COL6A2) placenta-expressed
      transcript encoded on chromosome 21
<220> FEATURE:
<221> NAME/KEY: modified_base
<222> LOCATION: (1)...(1)
<223> OTHER INFORMATION: n = c modified by 6-carboxyfluorescein (FAM)
<220> FEATURE:
<221> NAME/KEY: modified_base
<222> LOCATION: (15)...(15)
<223> OTHER INFORMATION: n = c modified by minor groove binding
      non-fluorescent quencher (MGBNFQ)

<400> SEQUENCE: 27
ngcatcatca aggtn                                                    15

<210> SEQ ID NO 28
<211> LENGTH: 61
<212> TYPE: DNA
<213> ORGANISM: Artificial Sequence
<220> FEATURE:
<223> OTHER INFORMATION: QRT-PCR calibration standard curve single
      stranded synthetic DNA oligonucleotide for detection of
      collagen VI alpha 2 (COL6A2) placenta-expressed
      transcript encoded on chromosome 21

<400> SEQUENCE: 28
gagatcaacc aggacaccat caaccgcatc atcaaggtca tgaaacacga agcctacgga   60
g                                                                  61

<210> SEQ ID NO 29
<211> LENGTH: 21
<212> TYPE: DNA
<213> ORGANISM: Artificial Sequence
<220> FEATURE:

<223> OTHER INFORMATION: QRT-PCR F primer for detection of mitochondrial
      ATP synthase O subunit (ATP5O) placenta-expressed
      transcript encoded on chromosome 21

<400> SEQUENCE: 29
ccctcactac caacctgatc a                                             21

<210> SEQ ID NO 30
<211> LENGTH: 21
<212> TYPE: DNA
<213> ORGANISM: Artificial Sequence
<220> FEATURE:
<223> OTHER INFORMATION: QRT-PCR R primer for detection of mitochondrial
      ATP synthase O subunit (ATP5O) placenta-expressed
      transcript encoded on chromosome 21

<400> SEQUENCE: 30
ccttgggtat tgcttaatcg a                                             21

<210> SEQ ID NO 31
<211> LENGTH: 15
<212> TYPE: DNA
<213> ORGANISM: Artificial Sequence
<220> FEATURE:
<223> OTHER INFORMATION: QRT-PCR fluorescent probe for detection of
      mitochondrial ATP synthase O subunit (ATP5O)
      placenta-expressed transcript encoded on
      chromosome 21
<220> FEATURE:
<221> NAME/KEY: modified_base
<222> LOCATION: (1)...(1)
<223> OTHER INFORMATION: n = t modified by 6-carboxyfluorescein (FAM)
<220> FEATURE:
<221> NAME/KEY: modified_base
<222> LOCATION: (15)...(15)
<223> OTHER INFORMATION: n = g modified by minor groove binding
      non-fluorescent quencher (MGBNFQ)

<400> SEQUENCE: 31
ngcttgctga aaatn                                                    15

<210> SEQ ID NO 32
<211> LENGTH: 65
<212> TYPE: DNA
<213> ORGANISM: Artificial Sequence
<220> FEATURE:
<223> OTHER INFORMATION: QRT-PCR calibration standard curve single
      stranded synthetic DNA oligonucleotide for detection of
      mitochondrial ATP synthase O subunit (ATP5O) placenta-expressed
      transcript encoded on chromosome 21

<400> SEQUENCE: 32
tcccctcact accaacctga tcaatttgct tgctgaaaat ggtcgattaa gcaataccca   60
aggag                                                               65

<210> SEQ ID NO 33
<211> LENGTH: 20
<212> TYPE: DNA
<213> ORGANISM: Artificial Sequence
<220> FEATURE:
<223> OTHER INFORMATION: allele-specific QRT-PCR F primer for detection
      of collagen VI alpha 1 (COL6A1) RNA-SNP rs1053312

<400> SEQUENCE: 33
ggcagccaca actttgacac                                               20

<210> SEQ ID NO 34
<211> LENGTH: 15

<210> SEQ ID NO 34
<211> LENGTH: 15
<212> TYPE: DNA
<213> ORGANISM: Artificial Sequence
<220> FEATURE:
<223> OTHER INFORMATION: allele-specific QRT-PCR R primer for detection
of collagen VI alpha 1 (COL6A1) RNA-SNP rs1053312

<400> SEQUENCE: 34
ctcggccagg cgctt                                                        15

<210> SEQ ID NO 35
<211> LENGTH: 14
<212> TYPE: DNA
<213> ORGANISM: Artificial Sequence
<220> FEATURE:
<223> OTHER INFORMATION: allele-specific QRT-PCR fluorescent probe
(allele G) for detection of collagen VI alpha 1 (COL6A1)
RNA-SNP rs1053312
<220> FEATURE:
<221> NAME/KEY: modified_base
<222> LOCATION: (1)...(1)
<223> OTHER INFORMATION: n = a modified by VIC fluorescent reporter dye
<220> FEATURE:
<221> NAME/KEY: modified_base
<222> LOCATION: (14)...(14)
<223> OTHER INFORMATION: n = c modified by minor groove binding
non-fluorescent quencher (MGBNFQ)

<400> SEQUENCE: 35
nccaagcgct tcgn                                                         14

<210> SEQ ID NO 36
<211> LENGTH: 14
<212> TYPE: DNA
<213> ORGANISM: Artificial Sequence
<220> FEATURE:
<223> OTHER INFORMATION: allele-specific QRT-PCR fluorescent probe
(allele A) for detection of collagen VI alpha 1 (COL6A1)
RNA-SNP rs1053312
<220> FEATURE:
<221> NAME/KEY: modified_base
<222> LOCATION: (1)...(1)
<223> OTHER INFORMATION: n = a modified by 6-carboxyfluorescein (FAM)
<220> FEATURE:
<221> NAME/KEY: modified_base
<222> LOCATION: (14)...(14)
<223> OTHER INFORMATION: n = c modified by minor groove binding
non-fluorescent quencher (MGBNFQ)

<400> SEQUENCE: 36
nccaagcact tcgn                                                         14

<210> SEQ ID NO 37
<211> LENGTH: 17
<212> TYPE: DNA
<213> ORGANISM: Artificial Sequence
<220> FEATURE:
<223> OTHER INFORMATION: allele-specific QRT-PCR F primer for detection
of collagen VI alpha 2 (COL6A2) RNA-SNP rs2839114

<400> SEQUENCE: 37
ggcgccagaa gacacgt                                                      17

<210> SEQ ID NO 38
<211> LENGTH: 14
<212> TYPE: DNA
<213> ORGANISM: Artificial Sequence
<220> FEATURE:
<223> OTHER INFORMATION: allele-specific QRT-PCR R primer for detection
of collagen VI alpha 2 (COL6A2) RNA-SNP rs2839114

<400> SEQUENCE: 38

```
gtcgtggcgc ccgt                                                    14

<210> SEQ ID NO 39
<211> LENGTH: 16
<212> TYPE: DNA
<213> ORGANISM: Artificial Sequence
<220> FEATURE:
<223> OTHER INFORMATION: allele-specific QRT-PCR fluorescent probe
      (allele G) for detection of collagen VI alpha 2 (COL6A2)
      RNA-SNP rs2839114
<220> FEATURE:
<221> NAME/KEY: modified_base
<222> LOCATION: (1)...(1)
<223> OTHER INFORMATION: n = t modified by VIC fluorescent reporter dye
<220> FEATURE:
<221> NAME/KEY: modified_base
<222> LOCATION: (16)...(16)
<223> OTHER INFORMATION: n = a modified by minor groove binding
      non-fluorescent quencher (MGBNFQ)

<400> SEQUENCE: 39
ngatgaccac cgcaan                                                  16

<210> SEQ ID NO 40
<211> LENGTH: 16
<212> TYPE: DNA
<213> ORGANISM: Artificial Sequence
<220> FEATURE:
<223> OTHER INFORMATION: allele-specific QRT-PCR fluorescent probe
      (allele A) for detection of collagen VI alpha 2 (COL6A2)
      RNA-SNP rs2839114
<220> FEATURE:
<221> NAME/KEY: modified_base
<222> LOCATION: (1)...(1)
<223> OTHER INFORMATION: n = t modified by 6-carboxyfluorescein (FAM)
<220> FEATURE:
<221> NAME/KEY: modified_base
<222> LOCATION: (16)...(16)
<223> OTHER INFORMATION: n = a modified by minor groove binding
      non-fluorescent quencher (MGBNFQ)

<400> SEQUENCE: 40
ngatgactac cgcaan                                                  16

<210> SEQ ID NO 41
<211> LENGTH: 30
<212> TYPE: DNA
<213> ORGANISM: Artificial Sequence
<220> FEATURE:
<223> OTHER INFORMATION: PCR F primer for amplification of coll
      agen VI alpha 1 (COL6A1) SNP rs1053320

<400> SEQUENCE: 41
acgttggatg ctatgtgacc cgcttctacc                                   30

<210> SEQ ID NO 42
<211> LENGTH: 30
<212> TYPE: DNA
<213> ORGANISM: Artificial Sequence
<220> FEATURE:
<223> OTHER INFORMATION: PCR R primer for amplification of collagen VI
      alpha 1 (COL6A1) SNP rs1053320

<400> SEQUENCE: 42
acgttggatg gagttgccat ctgagaagag                                   30

<210> SEQ ID NO 43
<211> LENGTH: 30
<212> TYPE: DNA
```

```
<213> ORGANISM: Artificial Sequence
<220> FEATURE:
<223> OTHER INFORMATION: PCR F primer for amplification of collagen VI
      alpha 2 (COL6A2) SNP rs2839114

<400> SEQUENCE: 43
acgttggatg accgcctcat caaggagagc                                30

<210> SEQ ID NO 44
<211> LENGTH: 30
<212> TYPE: DNA
<213> ORGANISM: Artificial Sequence
<220> FEATURE:
<223> OTHER INFORMATION: PCR R primer for amplification of collagen VI
      alpha 2 (COL6A2) SNP rs2839114

<400> SEQUENCE: 44
acgttggatg aagttgaggt catcgtcccg                                30

<210> SEQ ID NO 45
<211> LENGTH: 17
<212> TYPE: DNA
<213> ORGANISM: Artificial Sequence
<220> FEATURE:
<223> OTHER INFORMATION: primer extension reaction assay un-extended
      primer extension primer for collagen VI alpha 1 (COL6A1)
      SNP rs1053320

<400> SEQUENCE: 45
ctcttcttgg cagcgcc                                              17

<210> SEQ ID NO 46
<211> LENGTH: 18
<212> TYPE: DNA
<213> ORGANISM: Artificial Sequence
<220> FEATURE:
<223> OTHER INFORMATION: primer extension reaction assay primer extended
      product for collagen VI alpha 1 (COL6A1) SNP
      rs1053320 allele T

<400> SEQUENCE: 46
ctcttcttgg cagcgcca                                             18

<210> SEQ ID NO 47
<211> LENGTH: 20
<212> TYPE: DNA
<213> ORGANISM: Artificial Sequence
<220> FEATURE:
<223> OTHER INFORMATION: primer extension reaction assay primer extended
      product for collagen VI alpha 1 (COL6A1) SNP
      rs1053320 allele C

<400> SEQUENCE: 47
ctcttcttgg cagcgccgga                                           20

<210> SEQ ID NO 48
<211> LENGTH: 20
<212> TYPE: DNA
<213> ORGANISM: Artificial Sequence
<220> FEATURE:
<223> OTHER INFORMATION: primer extension reaction assay un-extended
      primer extension primer for collagen VI alpha 2 (COL6A2)
      SNP rs2839114

<400> SEQUENCE: 48
aagacacgtg tgtttgcggt                                           20
```

```
<210> SEQ ID NO 49
<211> LENGTH: 21
<212> TYPE: DNA
<213> ORGANISM: Artificial Sequence
<220> FEATURE:
<223> OTHER INFORMATION: primer extension reaction assay primer extended
      product for collagen VI alpha 2 (COL6A2) SNP
      rs2839114 allele A

<400> SEQUENCE: 49
aagacacgtg tgtttgcggt a                                              21

<210> SEQ ID NO 50
<211> LENGTH: 23
<212> TYPE: DNA
<213> ORGANISM: Artificial Sequence
<220> FEATURE:
<223> OTHER INFORMATION: primer extension reaction assay primer extended
      product for collagen VI alpha 2 (COL6A2) SNP
      rs2839114 allele G

<400> SEQUENCE: 50
aagacacgtg tgtttgcggt ggt                                            23

<210> SEQ ID NO 51
<211> LENGTH: 180
<212> TYPE: DNA
<213> ORGANISM: Artificial Sequence
<220> FEATURE:
<223> OTHER INFORMATION: polymorphic SNP PLAC4-41478755 (rs8130833) in
      coding region of placenta-specific 4 (PLAC4) gene

<400> SEQUENCE: 51
ttttacaaaa taagcctaat cgtaaaatat cactatagta tatagaacca tgtttaggcc    60
agatatattc gtcrtctaac ttgtatttaa cccaaatggt gttgcaatac aaaatgagtt   120 tcttttctt taagccaaat ttgaatttgc tccaatagct taaaagacac cctagcggcg    180

<210> SEQ ID NO 52
<211> LENGTH: 180
<212> TYPE: DNA
<213> ORGANISM: Artificial Sequence
<220> FEATURE:
<223> OTHER INFORMATION: polymorphic SNP PLAC4-41471145 in coding region
      of placenta-specific 4 (PLAC4) gene

<400> SEQUENCE: 52
ctcacatctc taaaggccac tcaggtggga caccatcaag acattgaaaa tcgacagaag    60
gaaggcagga aggggagagg atcraacctg tcaaaataga tattcagaaa atctgtgctc   120
taaaataagg cagcccttcc ctcacagcac acttattcct aatttcaaca ggactcctag   180

<210> SEQ ID NO 53
<211> LENGTH: 180
<212> TYPE: DNA
<213> ORGANISM: Artificial Sequence
<220> FEATURE:
<223> OTHER INFORMATION: polymorphic SNP PLAC4-41470591 (rs9977003) in
      coding region of placenta-specific 4 (PLAC4) gene

<400> SEQUENCE: 53
tcattctgag gcggtgctgc tgaaaatctt ggtgctgaac gtgtgttttt gagatttcca    60
gtctatcacr gggccacaag gtgtaaatat caagaaaaat gaattactag aaaggcaaag   120
tgaaaaagac atacaaaata caagtgtcat tcttttatt cttagtttgg acagatagtc    180
```

<210> SEQ ID NO 54
<211> LENGTH: 180
<212> TYPE: DNA
<213> ORGANISM: Artificial Sequence
<220> FEATURE:
<223> OTHER INFORMATION: polymorphic SNP PLAC4-41476236 in coding
region of placenta-specific 4 (PLAC4) gene

<400> SEQUENCE: 54

```
taattgattc ttggggtatc cctgtcttta ccctgtcttt aaggttttag caagactaag      60
tctcctggtt gaacygggga gctattttt cctttgtggg gaaggacagt attttatttt     120
tatattggag ggccttttga acctgtccta aattctaaag gggaggggg aaggttcata    180
```

<210> SEQ ID NO 55
<211> LENGTH: 25
<212> TYPE: DNA
<213> ORGANISM: Artificial Sequence
<220> FEATURE:
<223> OTHER INFORMATION: gene-specific primer for reverse transcription
of SNP rs8130833

<400> SEQUENCE: 55

```
gtatatagaa ccatgtttag gccag                                           25
```

<210> SEQ ID NO 56
<211> LENGTH: 30
<212> TYPE: DNA
<213> ORGANISM: Artificial Sequence
<220> FEATURE:
<223> OTHER INFORMATION: PCR amplification forward primer for SNP
rs8130833

<400> SEQUENCE: 56

```
acgttggatg gtattgcaac accatttggg                                      30
```

<210> SEQ ID NO 57
<211> LENGTH: 30
<212> TYPE: DNA
<213> ORGANISM: Artificial Sequence
<220> FEATURE:
<223> OTHER INFORMATION: PCR amplification reverse primer for SNP
rs8130833

<400> SEQUENCE: 57

```
acgttggatg tagaaccatg tttaggccag                                      30
```

<210> SEQ ID NO 58
<211> LENGTH: 18
<212> TYPE: DNA
<213> ORGANISM: Artificial Sequence
<220> FEATURE:
<223> OTHER INFORMATION: primer extension reaction assay un-extended
primer extension primer for SNP rs8130833

<400> SEQUENCE: 58

```
aggccagata tattcgtc                                                   18
```

<210> SEQ ID NO 59
<211> LENGTH: 19
<212> TYPE: DNA
<213> ORGANISM: Artificial Sequence
<220> FEATURE:
<223> OTHER INFORMATION: primer extension reaction assay primer extended
product for SNP rs8130833 allele A

<400> SEQUENCE: 59
aggccagata tattcgtca                                               19

<210> SEQ ID NO 60
<211> LENGTH: 20
<212> TYPE: DNA
<213> ORGANISM: Artificial Sequence
<220> FEATURE:
<223> OTHER INFORMATION: primer extension reaction assay primer extended
      product for SNP rs8130833 allele G

<400> SEQUENCE: 60
aggccagata tattcgtcgt                                              20

<210> SEQ ID NO 61
<211> LENGTH: 20
<212> TYPE: DNA
<213> ORGANISM: Artificial Sequence
<220> FEATURE:
<223> OTHER INFORMATION: QRT-PCR F primer for detection of
      placenta-specific 4 (PLAC4) mRNA

<400> SEQUENCE: 61 cctttcccccc ttatccaact                                             20

<210> SEQ ID NO 62
<211> LENGTH: 22
<212> TYPE: DNA
<213> ORGANISM: Artificial Sequence
<220> FEATURE:
<223> OTHER INFORMATION: QRT-PCR R primer for detection of
      placenta-specific 4 (PLAC4) mRNA

<400> SEQUENCE: 62
gtactggttg ggctcatttt ct                                           22

<210> SEQ ID NO 63
<211> LENGTH: 15
<212> TYPE: DNA
<213> ORGANISM: Artificial Sequence
<220> FEATURE:
<223> OTHER INFORMATION: QRT-PCR fluorescent probe for detection of
      placenta-specific 4 (PLAC4) mRNA
<220> FEATURE:
<221> NAME/KEY: modified_base
<222> LOCATION: (1)...(1)
<223> OTHER INFORMATION: n = c modified by 6-carboxyfluorescein (FAM)
<220> FEATURE:
<221> NAME/KEY: modified_base
<222> LOCATION: (15)...(15)
<223> OTHER INFORMATION: n = c modified by minor groove binding
      non-fluorescent quencher (MGBNFQ)

<400> SEQUENCE: 63
ncctagccta taccn                                                   15

<210> SEQ ID NO 64
<211> LENGTH: 74
<212> TYPE: DNA
<213> ORGANISM: Artificial Sequence
<220> FEATURE:
<223> OTHER INFORMATION: QRT-PCR calibrator single stranded synthetic DNA
      oligonucleotide for detection of placenta-specific
      4 (PLAC4) mRNA

<400> SEQUENCE: 64
cacctttccc ccttatccaa ctagccctag cctataccct ctgctgccca agaaaatgag   60
cccaaccagt acac                                                    74

<210> SEQ ID NO 65
<211> LENGTH: 184
<212> TYPE: DNA
<213> ORGANISM: Artificial Sequence
<220> FEATURE:
<223> OTHER INFORMATION: SERPINB2 (rs6098) polymorphic SNP within coding
region of serpin peptidase inhibitor clade B
(ovalbumin) member 2 (SERPINB2)

<400> SEQUENCE: 65
gttctgtgtt atatataaag aattccttct ttcttttcaa ggcacaagct gcagataaaa    60
tccattcatc cttccgctct ctcagctctg caatcaatgc atccacaggg rattatttac    120
tggaaagtgt caataagctg tttggtgaga agtctgcgag cttccgggaa gtaagtgaaa    180
cctg    184

<210> SEQ ID NO 66
<211> LENGTH: 30
<212> TYPE: DNA
<213> ORGANISM: Artificial Sequence
<220> FEATURE:
<223> OTHER INFORMATION: reverse transcription and PCR amplification
forward primer for serpin peptidase inhibitor
clade B (ovalbumin) member 2 (SERPINB2) gene

<400> SEQUENCE: 66
acgttggatg tgatgcgatt ttgcaggcac    30

<210> SEQ ID NO 67
<211> LENGTH: 30
<212> TYPE: DNA
<213> ORGANISM: Artificial Sequence
<220> FEATURE:
<223> OTHER INFORMATION: reverse transcription and PCR amplification
reverse primer for serpin peptidase inhibitor
clade B (ovalbumin) member 2 (SERPINB2) gene

<400> SEQUENCE: 67
acgttggatg cagacttctc accaaacagc    30

<210> SEQ ID NO 68
<211> LENGTH: 17
<212> TYPE: DNA
<213> ORGANISM: Artificial Sequence
<220> FEATURE:
<223> OTHER INFORMATION: primer extension reaction assay un-extended
primer extension primer for coding SNP of serpin
peptidase inhibitor clade B (ovalbumin) member 2
(SERPINB2) gene

<400> SEQUENCE: 68
tcaatgcatc cacaggg    17

<210> SEQ ID NO 69
<211> LENGTH: 18
<212> TYPE: DNA
<213> ORGANISM: Artificial Sequence
<220> FEATURE:
<223> OTHER INFORMATION: primer extension reaction assay primer extended
product for coding SNP of serpin peptidase
inhibitor clade B (ovalbumin) member 2 (SERPINB2)
gene allele A

<400> SEQUENCE: 69
tcaatgcatc cacaggga    18

<210> SEQ ID NO 70
<211> LENGTH: 19
<212> TYPE: DNA
<213> ORGANISM: Artificial Sequence
<220> FEATURE:
<223> OTHER INFORMATION: primer extension reaction assay primer extended
product for coding SNP of serpin peptidase
inhibitor clade B (ovalbumin) member 2 (SERPINB2)
gene allele G

<400> SEQUENCE: 70
tcaatgcatc cacagggga                                                    19

<210> SEQ ID NO 71
<211> LENGTH: 183
<212> TYPE: DNA
<213> ORGANISM: Artificial Sequence
<220> FEATURE:
<223> OTHER INFORMATION: COL4A2 (rs7990383) polymorphic SNP within
coding region of collagen IV alpha 2 (COL4A2) gene

<400> SEQUENCE: 71
gacgaagcta tcaaaggtct tccgggactg ccaggaccca agggcttcgc aggcatcaac        60
ggggagccgg ggaggaaagg ggacaragga gaccccggcc aacacggcct ccctgggttc       120
ccagggctca aggtgaggag caatttcatc atgaagctgg caagacactc tgaggcctcc       180
cca                                                                    183

<210> SEQ ID NO 72
<211> LENGTH: 30
<212> TYPE: DNA
<213> ORGANISM: Artificial Sequence
<220> FEATURE:
<223> OTHER INFORMATION: reverse transcription and PCR amplification
forward primer for collagen IV alpha 2 (COL4A2)
gene

<400> SEQUENCE: 72
acgttggatg aagggcttcg caggcatcaa                                        30

<210> SEQ ID NO 73
<211> LENGTH: 30
<212> TYPE: DNA
<213> ORGANISM: Artificial Sequence
<220> FEATURE:
<223> OTHER INFORMATION: reverse transcription and PCR amplification
reverse primer for collagen IV alpha 2 (COL4A2)
gene

<400> SEQUENCE: 73
acgttggatg accaatgttg ccaggcactc                                        30

<210> SEQ ID NO 74
<211> LENGTH: 17
<212> TYPE: DNA
<213> ORGANISM: Artificial Sequence
<220> FEATURE:
<223> OTHER INFORMATION: primer extension reaction assay un-extended
primer extension primer for coding SNP of collagen IV
alpha 2 (COL4A2) gene

<400> SEQUENCE: 74
gttggccggg gtctcct                                                      17

<210> SEQ ID NO 75
<211> LENGTH: 18
<212> TYPE: DNA

<210> SEQ ID NO 76
<211> LENGTH: 20
<212> TYPE: DNA
<213> ORGANISM: Artificial Sequence
<220> FEATURE:
<223> OTHER INFORMATION: primer extension reaction assay primer extended
      product for coding SNP of collagen IV alpha 2
      (COL4A2) gene allele G

<400> SEQUENCE: 75
gttggccggg gtctcctc                                                  18

<210> SEQ ID NO 76
<211> LENGTH: 20
<212> TYPE: DNA
<213> ORGANISM: Artificial Sequence
<220> FEATURE:
<223> OTHER INFORMATION: primer extension reaction assay primer extended
      product for coding SNP of collagen IV alpha 2
      (COL4A2) gene allele A

<400> SEQUENCE: 76
gttggccggg gtctcctttg                                                20

<210> SEQ ID NO 77
<211> LENGTH: 11558
<212> TYPE: DNA
<213> ORGANISM: Homo sapiens
<220> FEATURE:
<221> NAME/KEY: misc_feature
<222> LOCATION: (1)...(11558)
<223> OTHER INFORMATION: genomic sequence of placenta-specific 4 (PLAC4)
      gene locus
<220> FEATURE:
<221> NAME/KEY: prim_transcript
<222> LOCATION: (1)...(10009)
<223> OTHER INFORMATION: sequence known or predicted to be transcribed
      region of placenta-specific 4 (PLAC4) gene
<220> FEATURE:
<221> NAME/KEY: mRNA
<222> LOCATION: (1634)...(3401)
<223> OTHER INFORMATION: reference sequence corresponding to
      placenta-specific 4 (PLAC4) mRNA from GenBank
      Accession No. NM_182832
<220> FEATURE:
<221> NAME/KEY: mRNA
<222> LOCATION: (8749)...(10009)
<223> OTHER INFORMATION: reference sequence corresponding to
      placenta-specific 4 (PLAC4) mRNA from GenBank
      Accession No. NM_182832
<220> FEATURE:
<221> NAME/KEY: prim_transcript
<222> LOCATION: (10798)...(11132)
<223> OTHER INFORMATION: sequence known or predicted to be transcribed
      region of placenta-specific 4 (PLAC4) gene
<220> FEATURE:
<221> NAME/KEY: prim_transcript
<222> LOCATION: (11218)...(11558)
<223> OTHER INFORMATION: sequence known or predicted to be transcribed
      region of placenta-specific 4 (PLAC4) gene

<400> SEQUENCE: 77
tgggatgttt tcagattttt attatatggc aatcatatac ctgcacctag aaatatacaa    60
cctcggcgct gccattgcag gaagacaaag agactgtcta gagagtaacg tggcgatgcc   120
ctgggcagct ccatcattcc agggtaccat aaagggaagt gggaatgcac actccatctg   180
tttcacgcta ggctgaaagt ggcaggggga gaatttacac ctggcctgca aaaggcagcc   240
ttgtgttccc acttcagagc cccaacttct ccaaagccca tgcttgggaa atggccttgt   300
tggcagcagg caggagactg gtgcagtgtg ccagctgtgc aaaccccac cagactggtg    360 cagtgtgcca gctgtgcaaa ccccaccag cagcacccc accagcagcc aaagaaaaca    420
atttctaaag cagcccccag gatttcatgc cacgggggtg gtgaggggta ggaggaggtg   480

```
gaaagcattg aatcagaaag tcttccaggt accagcaatg ccagggttaa tatggtctgg   540
cttgcttttc aggtgagcac ctgtagctgg caggaaagtg gcttcttggt ggaggtgggc   600
atgaattcca gaagccttgg agagacatcc agagcccttc ccactacatc gtgctgcctc   660
ctggggaaat tcctaagctt tttttgaatc agaaaagcca ctgacaagca gacagaattg   720
tgtggcttgc gcagtgattg gagagctagg tgctttgggt actagtccca gagctgctac   780
ttgtcgaatg ttgggtattg gagagaagtc atttgagctg tctgagcctc tgtttcctca   840
tctgtaaatc agggaatttg aacaagtgac ctcagattcc ttctagaagc ctaacagtc    900 aatgatatca tctatttcat tgagagaat ctccatagct ctaatttttt gcccccagac    960
caatctgctt cagctttgtg tgggtgcaac acctggggtc ctgttaaaat gcagaatcgg  1020
attcagtgac cgagagcaga gctgagggtg gctgctgcca gctcacaggt cacacttgga  1080
gtcgttgctt ctttccccaa accagctgcc gatggttcct ggaaagagca ggaatacctt  1140
gcagaagggc ctagaaatag agattcccat atgcagtcca gacttattgg gtgagcctgt  1200
ctgcactagg acctgagaat ctgcatttta ttatatccct tgagtcccct ttaagcagcc  1260
acgctggccc cagccattgg actctatttg gaggccactg cagaggccag atgcccctct  1320
gctcggcggt ttcctgtgca gaaaggctgt gttctttctt cttcctaaat actcttccta  1380
ggttaagtgt ttccttctct ttgcccatct agaaaatctc cacctcaagc aggtcgtgtt  1440
ccaaaaactc ctcgtgttgg gcaagtggaa aacacgcagt ttttctagg ggtctcattc   1500 tgaggcggtg ctgctgaaaa tcttggtgct gaacgtgtgt ttttgagatt ccagtctat   1560 cacagggcca aaggtgtaa atatcaagaa aaatgaatta ctagaaaggc aaagtgaaaa   1620
agacatacaa aatacaagtg tcattctttt tattcttagt ttggacagat agtccattct  1680
tctacactgg tcccacggtt ctgaagcttt cctgtaatga tcagtggtta ccttgttgcc  1740
caagtaactg caaatccctc ctctacaaag tgtgcttgct ccaaggcagt gcaaactaga  1800
agttgttaca aatggttcca gtaacaaatt tgtttggcgg ccttttccca tgaatgagac  1860
agtggttatt tttgctaaag cagaaaggaa atgtgatact attgggctgt gttttgccct  1920
ctggagtaat cctgcttggg gaaatggag gcttgttcca gaatgcagaa atccctgtta   1980
aattaggcag tcttgggctg gaggacgtgt gcctgcctcc ccagtgcctc acaactcaca  2040
tctctaaagg ccactcaggt gggacaccat caagacattg aaaatcgaca gaaggaaggc  2100
aggaagggga gaggatcgaa cctgtcaaaa tagatattca gaaaatctgt gctctaaaat  2160
aaggcagccc ttccctcaca gcacacttat tcctaatttc aacaggactc ctagtcttgc  2220
cccacagcgt cacagcctac agcaaattag aaactggggt gggggcgga tattattcca   2280 ccagtaatac ccttgggacg gggcacacaa gatgtttgcc ctcctacctc tctgtcacct  2340
tcccaagaaa gggtcaagat gaaacagtgt gcgtttatgg tattgcgaga gttaagtgag  2400
ctgcggtgta ttagaacctt agcctcgcgc agcgtcagcc gtgtggtaag tgttccataa  2460
atcttcgttt agaaaagtg gcaaattcca ggctgctagt aaacaaagga gggaagacag   2520
acaaaacgga acagcaacaa cagaaaaccc aagaactaga tgcccaacaa tctgggtctg  2580
tatcttgaag gaatgtgcat cctgtcctct gactgcaaac ccaggccttc tgtggcccca  2640
cgatgctgcc tcctagccct cctaaggtgg gaatggagct ttaccccttg gtggcaaaca  2700
gacctggctc catggatctc aacctgggt gattgtgtcc ccaccccagg ggacatctgg   2760
catcctctgg ggacattttg agttctcaca acttagaggg tgctactggc gtcctgtggg  2820
```

-continued

```
tggagactgg aagtgctgct cggcattctt tgccgtacag ggcagccccc acaacaaaga   2880
acgatctggt ccaaaatggc aaccatgcca agattgagaa atcctggtta ctcgacacag   2940
caggtcggct ggcctaggag ttgctgccca gagaggcaaa gggagaatgt ccagtggaaa   3000
cagctgccct gagcatacag ggcacgctga cacctgctga ttcccccatc cttaaggtcc   3060
tgtattgttc ctaacaccac gtggatcttc ttgccagatg cattaaagtg tgagaagagt   3120
taaaaatcac ttataactgg agtgactggg ggttaaagag gagaaaaaat ttgaacctga   3180
ctcaaaggat gagcatgttt ttctttcttt cttcggcaca ttggctgggt gtggcggctc   3240
catgcctatt atcccagcac tttggaaggc cgaggtggga ggattgcttg aggttaggag   3300
ttcaagatca gcctaggcaa catagcaagt ccctatctat ataatttttt ttttaaatta   3360
gccaagcttg gtggtgcatg cctgtagtcc cagctactca ggaggctgag gcaggaggat   3420
cacttgagct caggagttca aggctgcaat gaattacgat tgtgccactg cactccagca   3480
tgtgcaacag agcaagacct tgcctcaaaa catattaagc acctactgca tgtcaggcc    3540
ttggtctaag ccctggtatg caacagtcaa ctagacagag agtcttgg cttttacaga    3600
acctccccct ataaggaaga cagattgtca aggaagtaaa cagactttta gaggagtgct   3660
gtgagacagt gccatgtggg aagggtatt ggtgaaagaa tcctgcttta taagggcggt    3720
tatggaagac ctctctgagg aggtgcaatt tgagatgaga ttggcttgag gaggactgag   3780
ccttcagaag ttagggaaag cgtgtcccag gctgcagcca gggaggtgaa gacttgaggg   3840
tgtcagggtg aggagtgagg gtgtcagggt gactgagggt gccagggtga ggagtgaggg   3900
tgtcagggtg aggagtgagg gtgtccaggg tgaggagtga gggtgtcagg gtgaggagtg   3960
agggtgtcca ggttgagtga gggtgtccag gatgaggagt gagggtgtcc agggtgagga   4020
gtgagggagt ccagggtgag gagtgaggga gtccagggtg aggattgagg gtgtcagggt   4080
gagtgagagt gtccagggtg aggagtgagg gtatccaggg tgagtgaggg tgtccagggt   4140
gaggagtgag ggtatccagg gtgagtgagg gtgtccaggg tgagtgaggg tgtcagggtg   4200
agtgaacgtg tccagggtga gtgagggtgt ccagggtgca gagtgaggtg tccagggtga   4260
ggagtgacgg tgtctggggt gagtgagggt gtccagggtg aggagtgagg gtgtcagggt   4320
gagtgagggt gtccagggtg agtgcacatg tgtggtgagg aggtgtttgc agtgcttcag   4380
gcgcagcaac tctttcatct agtttaaaat tgtgctctga ggttagattt tagtagaaca   4440
aaggccttac aaagaatgtg aaaacattgt gcttccctgc ttacaggcaa ttaaaaagga   4500
gaatcaagct gagggtgcct ggtgtggggt ggggtggaga agaccacaga gactattgtg   4560
tgttttattc aacagtgtcc tgggctgctt ctctccagaaa tgtccctgac acatggatgt   4620
aagtgtggct agtttactgg gagatgatcc cagtgatgca ggacaggcga gccctaagat   4680
tgaagcatag cccgggaggg ttcttagctt tgcccaggaa ggaactcaag ggcaagccag   4740
tggtgttagc aactttatt gaagcggccg gctgtgcaca gcagcagcag aggcgctgct    4800
ccttgcaaag cagggctgcc ctacaggctg tgcgcccaca gtagcagctc agaggcagtt   4860
ctgcagtggt atttgtatcc actttaatt atatgcaaat gaaggggcag tttatgcaga    4920
catttccagg gtgagggtgg taacttctgg gtgctgccag agccatggtg aactgacttg   4980
acacaggtcg gtgtgtccta tggaaactag catctgccct ggacctattt tagctagtgc   5040
tcagtttggt ctgagtgcct gagccccact tccagagttg agtcccacct cctacctcat   5100
tccccttca gagattagat actcctcctt aatcttaagg gggctgcaga agggcggaga   5160
tctgtttcc gtaactactt cctgctgagt ttatggacgt aggccctgcc tggcactgga   5220
```

```
ggagtaaaaa tctctggata cctgatctaa ggagcccaga ggcaggacga tttcattctc    5280
cgtgtcagtg gacaggatgg gctggaagcc ttgtgccagc attgtctctg gaactgtggt    5340
aatctagaat acacaaactt tactaagagg ttaaagaagc aaggaccaaa catttgtaac    5400
aagacagttg tcaaaggtcc tagaagaggt gaaaaacagg tgagacttgg gaaggcactt    5460
ttgatggttg accagatata gttgggggca gtgccctggt tatatctatg taactaggta    5520
gcttgctcat agatcttttg aatgttaacc tcaacctgtc cagagttaat atatgtgcag    5580
caggttttat taataactgc acaagacccc accttgttca gctagtaaat aatccaatgc    5640
tagtctgtta tcaacaacta cattttccag agtctgggga actcttgaat tctctttaat    5700
gcctgatctc cgttggtggc taaggattct aggatttgag ccaagttctt tagcgttaac    5760
tcatggtagg caaagccacc ccagggtgct gctagtccta ttgccaccct gattcctgcc    5820
agaattagtt ttattgctta cttatttctg atattcttgg gtcctaggcg ttatagattg    5880 tgaccctgg  agggttaaga gtggccaacg ttcattcatg tcagttccaa gttttttaga    5940
tacaagggaa agctattcct taaagaagag gtgactcctt agggagttgg agtggttaca    6000
gggtgtgact tcttcccatt catagtcaca aacaaaaatg aacccaacta gggcaccaag    6060
agaagccctg cggggtgcga tgtttatact tcattgccag gttgggtcta tagagatatt    6120
ttccacctgt tctcatggtg gtggttgaac aatctttgtt ttctagaaga aggtagtact    6180
gtcaccttcc cagatcaggc agttgttttt cctttgtatg ttcccatccg ggagaaggta    6240
ccatatatgg tcttttcact cacaaatgga atctcattta cctccccgtg gtcttggaaa    6300
cttggcaact agagttggac cagagcatcg cagggaagct tccacttttg tgtcattaat    6360
gcaagagtgg atgcaaatgt tagagttatg agtgcactgg agatatagat gcccaacttc    6420
ccagattccg ataatagtgg tcagggcagg gggacagcag ggtccagggg ggatccacta    6480
agtggggaag agttccactt cacaataggg gtttgggtat tttggggtgc tatggttagt    6540
taggaggtct ggggacatgg tcctgagatt ttccagatag gtcggaagat gaaactgtct    6600
atcctggggg tgttgatgac aaatctggca gccataaaga tgattctatg atgctataat    6660
ttttgaaata tttactgtag aattttgtcc accctccctg tccacataca cactagctta    6720
ggttaattag aagagcaaac agaattaaca gtggcatcat ggtatctggt tgggtcttag    6780
agtagcttct atacccaaca agcccacagg agatgtttcc caggaggagg tggctggtta    6840 aagcccataga aaggaagtac tacagtcagg aagaagagca agatcaatgc tcctattccc    6900
atctacagca ttacattacc tcttctggct gagtgttgat tatttaaat aggtagcaga    6960 ggtcttccaa agctttactg atattggttg tggttgtagt gcccttcctt tgtgcctgtg    7020
actcataaga aacaggttta gtcctggatc tgtgtgccca gtaggtgtt  ccctgaagtt    7080 taacagcagt gggggtactt aacaataccct gataaggccc cttccatttc attgtaattg    7140
attcttgggg tatccctgtc tttaccctgt ctttaaggtt ttagcaagac taagtctcct    7200
ggttgaaccg gggagctatt ttttcctttg tggggaagga cagtatttta ttttatatt    7260 ggagggcctt ttgaacctgt cctaaattct aaaggggagg gggaaggtt catataggta    7320 attactacaa gccaagacca cagcagctca acacataaaa tccatagaca aatcagtttt    7380 acaacccat  ttcctggctt ctagttcttg gcttccatac tgctcaaaag gagttcaagg    7440
gccaatgagt gcccgcccac ctccacactc atgcactgtg cagatgactt acacagacca    7500
tctacaacat agctgaattt cctgacatgt tctatactac ctctttctta aagttatttt    7560
```

```
actctaggat agggaattta ctatacagga ttcctccaca tataaaatta ctctttcttt    7620
atatccttcc ttgcaaaaca acaaaaaat acattttcta ttcataatat tctttacatc    7680
tctcttttct actcactggt tcactcatgt tttgaacctc ccatttagta acttccggat    7740
tagacaaaaa attttttctc aataaagaat acatttcttt agcacatttt atggaaacct    7800
aggaaggaag aagtcatgaa cttcacacta gacattgtca ttctataact gagaaccatt    7860
ctaccatttt atgattttaa accacacatt aagcatatcc catttacgtg tatttaatta    7920
tttcactttt aactttatct agatcaccga gaaccaaggt accatgcaaa gctggtcacc    7980
atttaaagcc attttaacca ttttaaagcc tatgaacatc agtgacttac ctaggtaaaa    8040
atcctaaagt taaattttag aagatacaag attctcttca aactaataag ctttcagtag    8100
tcttatttgt tgaatgtatg agtgttcttt tatctataag ccagtttgac agcacgctag    8160
atgtaacaca catcacaata catgtacata tacccaaaaa catattaaat aaaatgacct    8220
atacaagaca actggattca agttatttac agaactggga cccatctacc tggccaaatt    8280
ttgtttgccc cgataggtat ggaaaacagg aaaaggcagg acagggaatc ccatagcatc    8340
aactaaaaag gggaggaagc aaactgcatt gctcaaaagg agattctgga gtccccacgc    8400
cactggagag cacactcagt ggtggaaata ccaaagaaaa atgttcaggc ggctgcttat    8460
ctgccactgt ggaaagctgt cctctgggac agtaaactta cttgagctaa gcagctcact    8520
ggggctagta ggagaaggtt agctctagta ttgatggaag ctttttgttg ttattgttct    8580
ctctcaccag agcagttagg acatttgcat tgccaggggc ccttttgcgt atagtaggcg    8640
cagtgattct ggcccagggg tcagcaagtc aggcatcaag tcttgtctag gcatcccaga    8700
tgctaatttt gtaacatttt ctcaagatga gtaatcctga ggggcaagga ggcttaaagt    8760
cactgttaac aattgtactt tttggctatt tcttttact ccctcttt gccctgtccc    8820
tgttgttgta aactttaaag gctatgttta agcgtcgttt cataggactt gaaggtccca    8880
ttgctgcttt ttgtagattc ctcctaatgt caggagaaga ttgaatgaga aaatgtatac    8940
ccaggagagc ttgcccttct ggggtgtctg ggcctgcatt agtatatttc ctgagtgctt    9000
caactaaaag accctgaaac agagcgggat tttcatcttt tccccgagtt acttctttaa    9060
ccttgtcata attgactggc ttaaccacac acttttttcct ctactttttt ttccccacag    9120
cacagcaagc ggatgacaat atttgtaaat cgtggcaatt tgaagaacat agtcaacgta    9180
acaaactctt gtataagctt ttctggttta tctgaaaact ggccaattct ttccttttat    9240
aaggtctaat tagacatgga aagtggcata tgtactcttt gagtgttccc tcatttccat    9300
caactacttt ccacagtgga cacaggcttg accttagggg ctgatatgga gccccactcc    9360
tggtgtactg gttgggctca ttttcttggg cagcagaggg tataggctag ggctagttgg    9420
ataaggggga aaggtgcctg atgatattgg ggtggaatct cattagggaa ttggcgagaa    9480
cccccactca ggactggggg actgaagaga ctctggggag gcttatgaac tttctatggg    9540
gagcagctag gtggggatcc cttatgcatg gcattctaat gcctggaagt aacgtgatcc    9600
agtatagagc cataaaagcc tgtacataag ggatctcttc ccattttcct tctcttttac    9660
aaaataagcc taatcgtaaa atatcactat agtatataga accatgttta ggccagatat    9720
attcgtcatc taacttgtat ttaacccaaa tggtgttgca atacaaaatg agtttctttt    9780
tcttttaagcc aaatttgaat ttgctccaat agcttaaaag acaccctagc ggcgagtccc    9840
ttgggatact ccttgttgtc cccatgccta tattaaggat ctctctacag aggggttttat    9900
tagcccaagt ttagcaaaag cctagttact cttccctctt aaattcccgt gttctttaaa    9960
```

```
                                                              -continued ggtgtaaata tagatagcaa ggtgttataa aaatggatta tgagctacga atgggcagtc   10020
gaatgtggag cctaaattcc atagagatct agagttgggt ggagaggggg ctaaacaaat   10080
ggaggaaggg aaagggtaa acagcgttgc ccaaggggag acctcagagg ctctgacttg    10140
ctgaagaacc tacccagtag tggagatact gaaaaaaata ttgggctggc cacttgtcta   10200
ccactgtagg tggctgactg ccaggccagg agcctgggag ctcccaattc ctttgaccaa   10260
gagcagctta ggcaagggag ttataagaca gtacacagga aggagcttgc aattggctat   10320
taggaaaata atactcctaa cttcagggtg gaaaaagaca agaccaatat tcgcctagcg   10380 aaagggtat aacccacaat cctagaggaa atgtcagtgc taaaaacccc agagcatctg    10440
gagggtggcc tataataccg atgctgagaa cccaaaatgc ctgcgtttca gccaacaagg   10500
atgccctcgc caaagcagct gtgcacagca gtgccaaaaa ccctggggta cccagtgggc   10560
ggccaacccc gtgaacccaa gaccaggtta cagaacatag aacaacgtga caacgtgact   10620
ctggtatccc agagtcaaca caacagggga cctctcacaa ccaagtgtcc tgccttaaac   10680
aattgcccaa atacaattaa cagaaagtcg aaagcaaaca taagactcca aacaagacat   10740
acatgttagg actgaaaatg aaaccaaagt ggagcaataa aatggagtca gaggagaaag   10800
aaccaggtga aggggtggca agaatgtgct tcaaggcacc taaaccgtgg ggaactgacc   10860
gcttagccaa aggcttttat ttcctagctt acctgatatt actgggggag ggtgcaaagg   10920
ggactctcac ccatccacag aagacaaaat ggcaccagcc agtcttccac gtgggacccg   10980
ggtgcaggtc tctctaggtt ccccagcttg ggggtgctca gcttctgtgt cggggctgg    11040 ctcgttagag cagtgggtcc cacacgaggc agctgtacta tggacacttg gctgtccact   11100
cagtttcacc acctgccagg gaaagatgat ggctgtgaaa agaggcactg gttagggtta   11160
gagctcggta gtgttagcag ctctttattg gtacttcctc agtgttacag atcttacatc   11220
ctcaatcaca gactgcttca ccgtctcttg ctgtcttgcc aactgctgtc tcttgtctct   11280
caccaattgc tgcctctctg tctctgctgt cttgcctctc tgccaattgc caccatctcc   11340
gctgtccttg tccctttgct ggttgccaga tgatgcagga caggcaagcc ccaagactgg   11400
ggcttagcct gggagagttc ttggatttgc ccaaagattc aagggtgagc tggtggtgtt   11460
aggcagcagc tttcatggaa gcagctgtgc acagcagcgc cagagatgcc gctccttgca   11520
gatcagggct gctccatagg ctgtgtgccc tgagtagc                          11558
```